US012606822B2

(12) United States Patent
Zangi et al.

(10) Patent No.: US 12,606,822 B2
(45) Date of Patent: Apr. 21, 2026

(54) SYNTHETIC MODIFIED RNA AND USES THEREOF

(71) Applicant: Icahn School of Medicine at Mount Sinai, New York, NY (US)

(72) Inventors: Lior Zangi, New York, NY (US); Yoav Hadas, New York, NY (US); Nishat Sultana, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 1021 days.

(21) Appl. No.: 17/774,912

(22) PCT Filed: Nov. 6, 2020

(86) PCT No.: PCT/US2020/059482
§ 371 (c)(1),
(2) Date: May 6, 2022

(87) PCT Pub. No.: WO2021/092440
PCT Pub. Date: May 14, 2021

(65) Prior Publication Data
US 2023/0008266 A1     Jan. 12, 2023

Related U.S. Application Data

(60) Provisional application No. 62/932,255, filed on Nov. 7, 2019.

(51) Int. Cl.
*C12N 9/18* (2006.01)
*A61P 1/16* (2006.01)
(Continued)

(52) U.S. Cl.
CPC ................ *C12N 15/11* (2013.01); *A61P 1/16* (2018.01); *A61P 9/00* (2018.01); *C12N 9/18* (2013.01)

(58) Field of Classification Search
None
See application file for complete search history.

(56) References Cited

U.S. PATENT DOCUMENTS

| | | |
|---|---|---|
| 8,278,036 B2 | 10/2012 | Kariko |
| 2004/0005564 A1 | 1/2004 | Mauro |

(Continued)

FOREIGN PATENT DOCUMENTS

| | | |
|---|---|---|
| WO | 2013151665 A2 | 10/2013 |
| WO | 2015105191 A1 | 7/2015 |

(Continued)

OTHER PUBLICATIONS

Elosua R, Sayols-Baixeras S. The Genetics of Ischemic Heart Disease: From Current Knowledge to Clinical Implications. Rev Esp Cardiol (Engl Ed). Sep. 2017;70(9):754-762. English, Spanish. doi: 10.1016/j.rec.2017.02.046. Epub Jun. 13, 2017. PMID: 28623161. (Year: 2017).*

(Continued)

*Primary Examiner* — Evelyn Y Pyla
*Assistant Examiner* — Jagamya Vijayaraghavan
(74) *Attorney, Agent, or Firm* — Heslin Rothenberg Farley & Mesiti P.C.

(57) ABSTRACT

The present application relates to a nucleic acid molecule comprising a first nucleic acid sequence comprising at least a portion of a 5' untranslated region (5' UTR) of a carboxylesterase gene and a second nucleic acid sequence encoding a protein of interest, where the second nucleic acid sequence is heterologous to and operatively coupled to the first nucleic acid sequence. Also disclosed are methods of expressing a protein of interest in a target cell, methods of treating subject for cardiac ischemia or hepatic ischemia, and methods of (Continued)

identifying a nucleic acid sequence capable of selectively enhancing translation of a heterologous protein of interest in a target cell.

19 Claims, 23 Drawing Sheets

Specification includes a Sequence Listing.

(51) Int. Cl.
    A61P 9/00           (2006.01)
    C12N 15/11         (2006.01)

(56)               References Cited

U.S. PATENT DOCUMENTS

| | | |
|---|---|---|
| 2004/0076954 A1 | 4/2004 | Caldwell |
| 2011/0150774 A1 | 6/2011 | Rivier |
| 2018/0353618 A1 | 12/2018 | Burkhardt |
| 2019/0117733 A1 | 4/2019 | Chien et al. |
| 2019/0203226 A1 | 7/2019 | Zangi |

FOREIGN PATENT DOCUMENTS

| | | | |
|---|---|---|---|
| WO | 2018035253 A1 | 2/2018 | |
| WO | 2019007701 A1 | 4/2019 | |
| WO | WO-2021155479 A1 * | 8/2021 | ........... A61K 31/635 |

OTHER PUBLICATIONS

Mäkinen VP, Civelek M, Meng Q, et al.; Integrative genomics reveals novel molecular pathways and gene networks for coronary arteryl; PLoS Genet. Jul. 1, 20147;10(7):e1004502. doi: 10.1371/journal.pgen.1004502. PMID: 25033284; PMCID: PMC4102418. (Year: 2014).*

Padala SK, Lavelle MP, Sidhu MS, Cabral KP, Morrone D, Boden WE, Toth PP. Antianginal Therapy for Stable Ischemic Heart Disease: A Contemporary Review. J Cardiovasc Pharmacol Ther. Nov. 2017;22(6):499-510. doi: 10.1177/1074248417698224. Epub Mar. 31, 2017. PMID: 28361599. (Year: 2017).*

Selwyn AP, Kinlay S, Libby P, Ganz P. Atherogenic lipids, vascular dysfunction, and clinical signs of ischemic heart disease. Circulation. Jan. 7, 1997;95(1):5-7. doi: 10.1161/01.cir.95.1.5. PMID: 8994406. (Year: 1997).*

Institute of Medicine (US) Committee on Social Security Cardiovascular Disability Criteria. Cardiovascular Disability: Updating the Social Security Listings. Washington (DC): National Academies Press (US); 2010. PMID: 24983036. (Year: 2010).*

Bruxel et al., "Association of a carboxylesterase 1 polymorphism with appetite reduction in children and adolescents with attention-deficit/hyperactivity disorder treated with methylphenidate," The Pharmacogenomics Journal, 2012, 13(5):476-480.

Arsani et al., "Optimization of mRNA untranslated regions for improved expression of therapeutic mRNA," RNA Biology, 2011, 15(6):756-762.

Rasmussen et al., "Carboxylesterase 1 genes; systematic review and evaluation of existing genotyping procedures," Drug Metabolism and Personalized Therapy, 2019, 33(1):3-14.

Sultana et al., "Optimization of 5' Untranslated Region of Modified mRNA for Use in Cardiac or Hepatic Ischemic Injury," Molecular Therapy—Methods & Clinical Development, 2020, 17(1):622-633.

Supplementary European Search Report issue in connection with European Patent Application 20883694.0 and mailed on Oct. 19, 2023.

Yoshimura et al., "Functional polymorphisms in carboxylesterase 1A2 (CES1A2) gene involves specific protein 1 (Sp1) binding sites," Biochemical and Biophysical Research Communications, 2008, 369(3):939-942.

* cited by examiner

| # | Gene ID | Protein fold change (MI vs Sham) | RNA fold change (MI vs Sham) | 5′ UTR length |
|---|---------|----------------------------------|------------------------------|---------------|
| 1 | Pygl | 3.36 | 0.66 | 100 |
| 2 | Serpina 1b | 5.93 | 0.57 | 97 |
| 3 | Frmd5 | 2.4 | 0.52 | 226 |

FIG. 1F

| # | Gene ID | Protein fold change (MI vs Sham) | RNA fold change (MI vs Sham) | 5′ UTR length |
|---|---------|----------------------------------|------------------------------|---------------|
| 1 | Smarca2 | 1446.68 | 0.41 | 110 |
| 2 | Vtn | 27.89 | 0.34 | 230 |
| 3 | Gsn | 10.62 | 0.48 | 84 |
| 4 | Pzp | 8.86 | 0.46 | 56 |
| 5 | Igsf10 | 6.24 | 0.29 | 568 |
| 6 | Serpina1b | 5.93 | 0.27 | 97 |
| 7 | Fbln1 | 5.53 | 0.40 | 126 |
| 8 | Flad1 | 3.66 | 0.40 | 216 |
| 9 | Ppip5k2 | 3.45 | 0.35 | 503 |
| 10 | Scrn2 | 2.96 | 0.54 | 104 |
| 11 | Etfrf1 | 2.75 | 0.48 | 386 |
| 12 | Frmd4d5 | 2.42 | 0.20 | 226 |
| 13 | Itm2b | 2.41 | 0.63 | 145 |
| 14 | Tmem201 | 2.24 | 0.47 | 121 |
| 15 | Clpx | 2.24 | 0.58 | 227 |
| 16 | Fn3k | 2.21 | 0.17 | 36 |
| 17 | Ces1d | 2.04 | 0.22 | 85 |
| 18 | Hmgn2 | 2.01 | 0.61 | 182 |

FIG. 1G

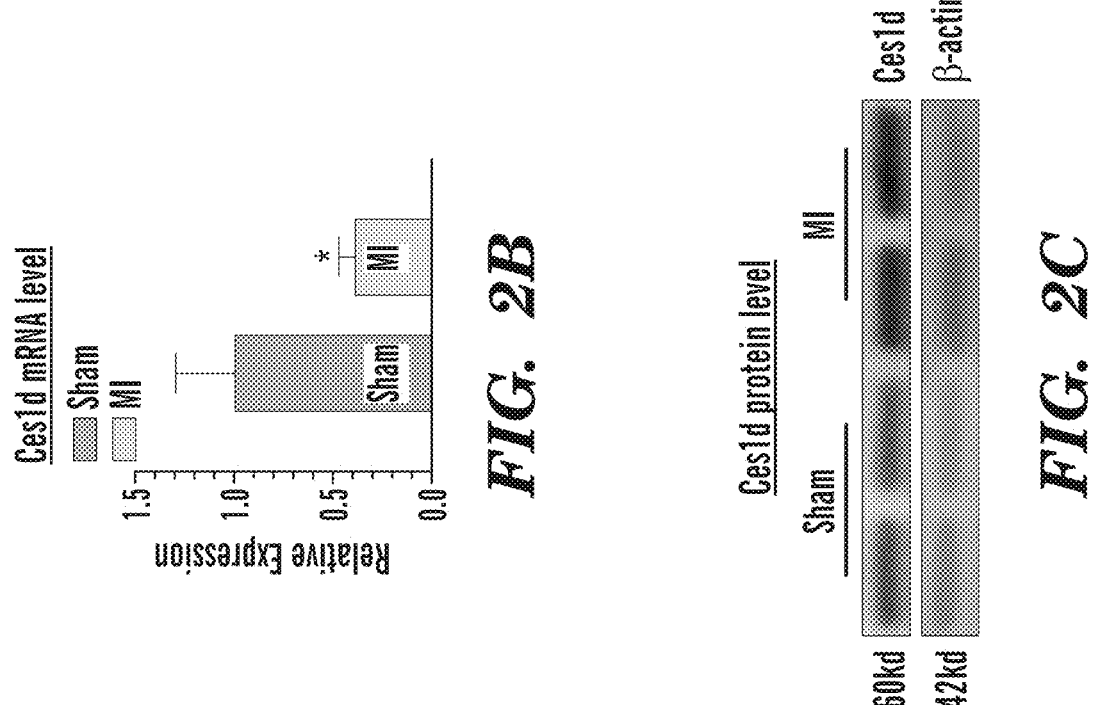
*FIG. 2B*
*FIG. 2C*
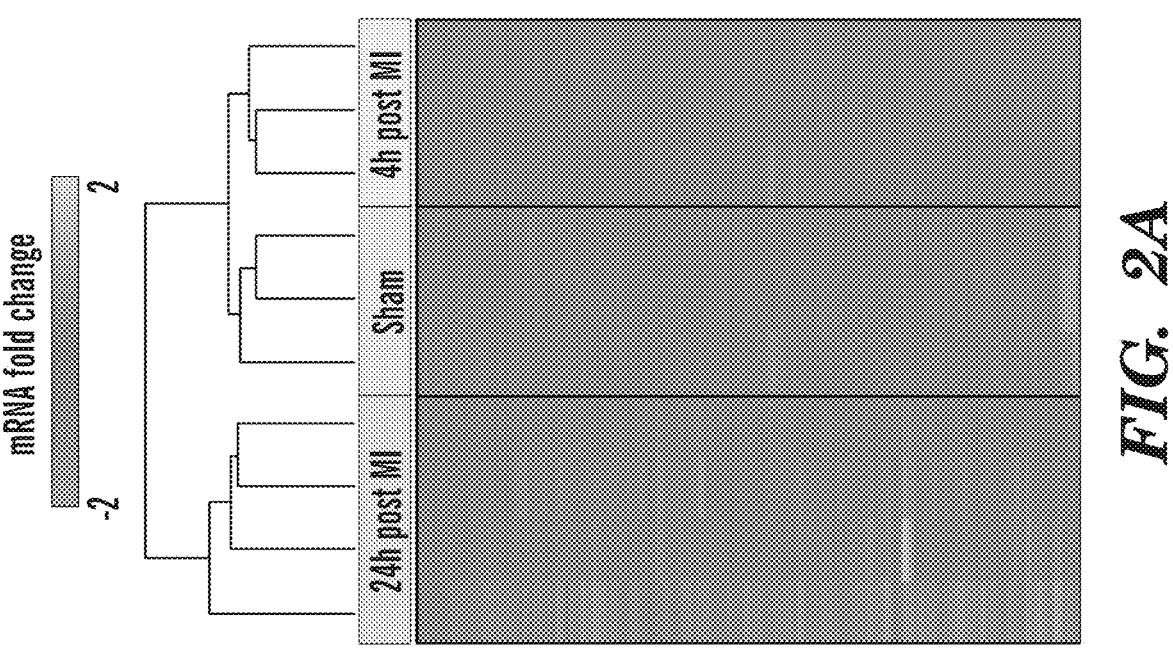
*FIG. 2A*

| W/o | eGFP - control | | | eGFP - Ces1d | | |
| | 24 hours | 48 hours | 72 hours | 24 hours | 48 hours | 72 hours |

GFP

β-actin

| 0% | 86% | 50% | 35% | 106% | 62% | 41% |

Ratio to β-actin     171%     209%

Ratio to control     100%     122%

0    24 hours   48 hours   72 hours    96 hours

LAD ligation and
25 μg Luc modRNA injection

Measuring of Luc signal
with IVIS®

*In vivo* screen
(total expression in 24, 48, 72, and 96 hours)

■ Luc- Control     ▦ Luc- Serpina 1b
▨ Luc- Pzp     ▦ Luc- Ces1d

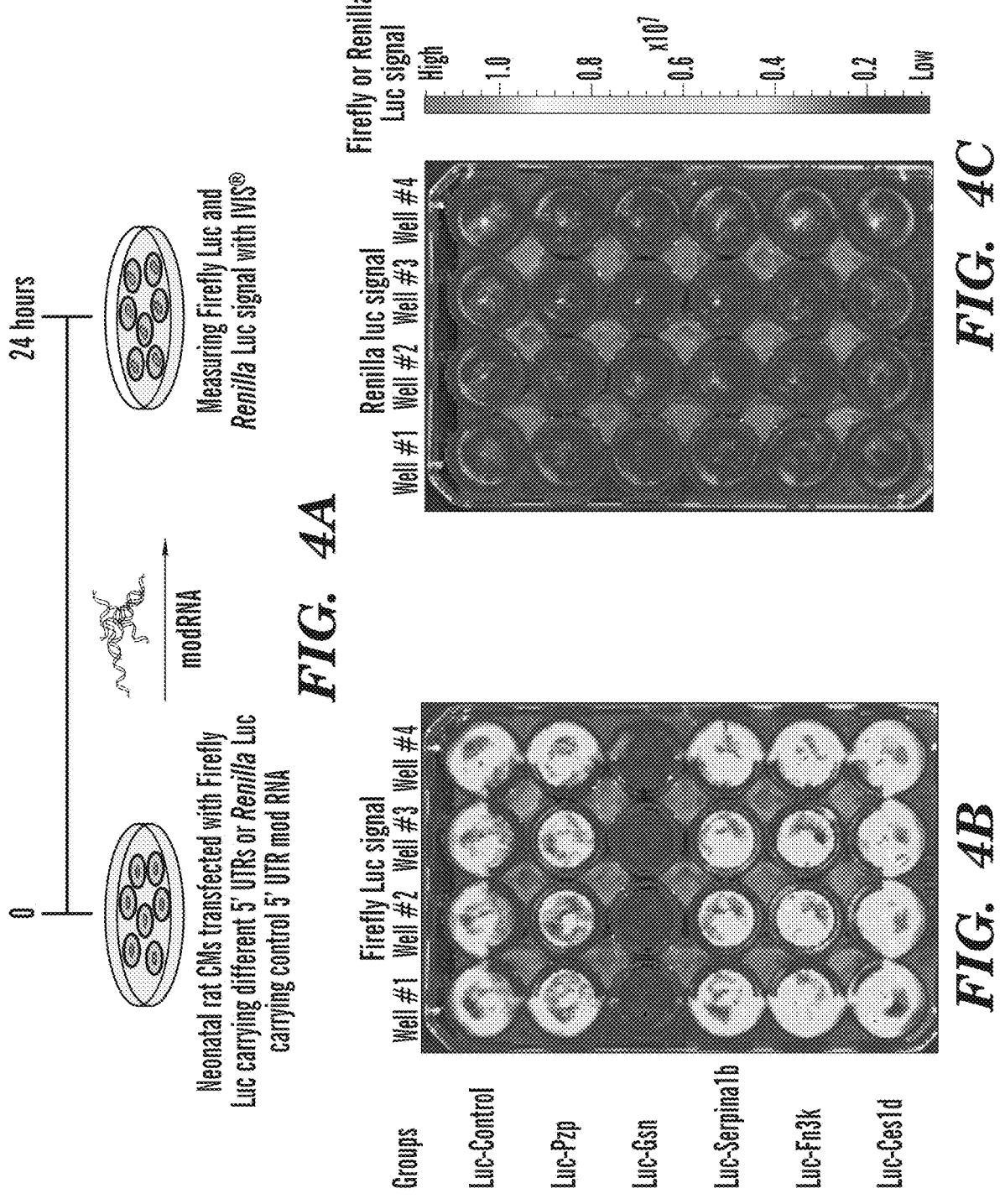

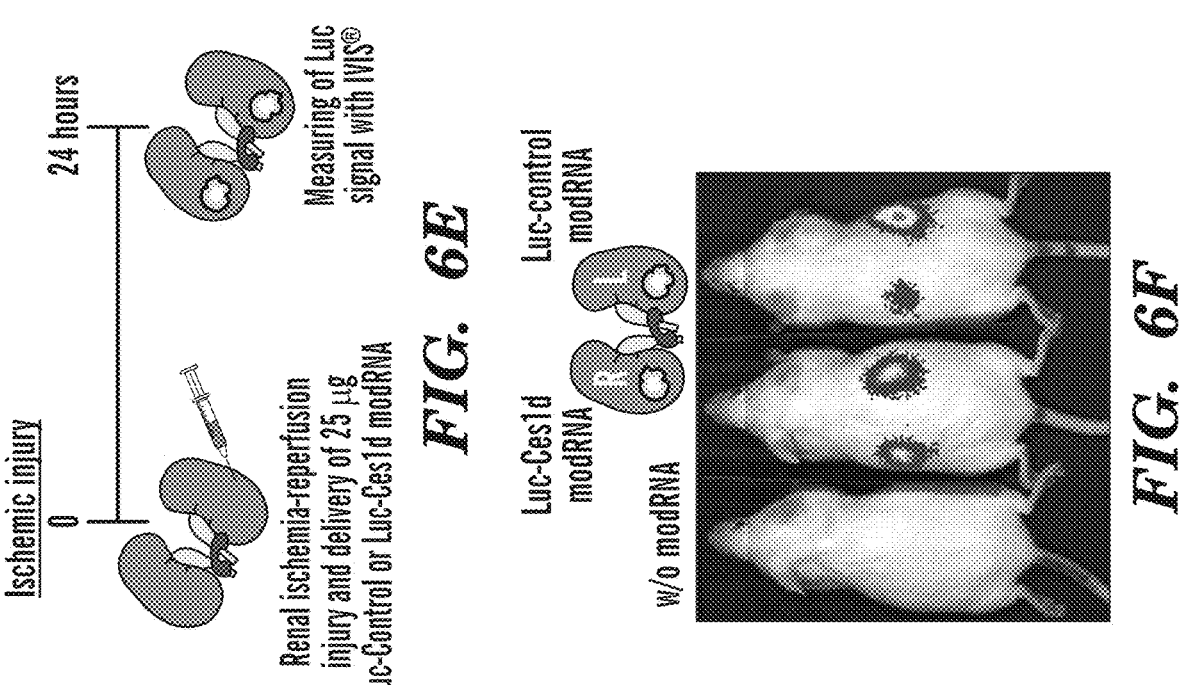
*FIG. 6E*
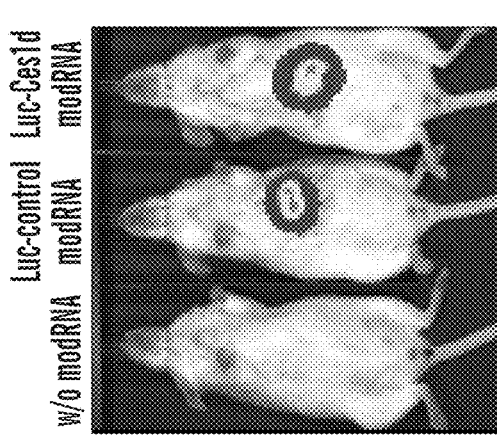
*FIG. 6F*
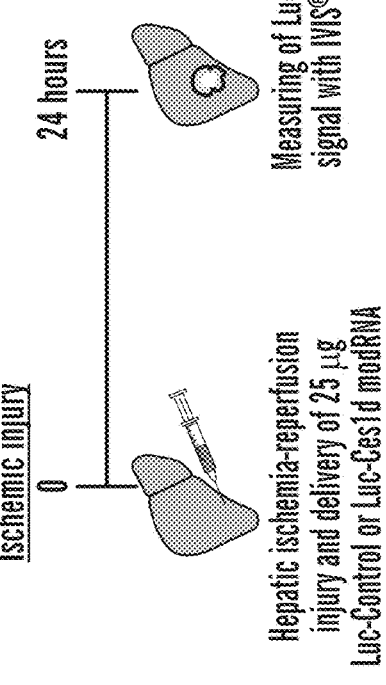
*FIG. 6C*
*FIG. 6D*

No Ischemic injury

Ischemic injury

| Species | Element A | Element B | Element C | Element D | Element E |
|---|---|---|---|---|---|
| Mouse | AGGAGGCGGGTCCCCTGGTCCA (SEQ ID NO: 7) | CAACAGAAGCATTGCTAAAGCAG (SEQ ID NO: 8) | CAGATAGC (SEQ ID NO: 9) | TCAGAGACCCACAGAGCCC (SEQ ID NO: 10) | TTGTCCTTCCACA (SEQ ID NO: 11) |
| Rat |  | TGCTAAAGGAA (SEQ ID NO: 12) | CAAATAGC (SEQ ID NO: 13) | CCACAGATCCGCAGAACCC (SEQ ID NO: 14) | TTGTCCTTCCACA (SEQ ID NO: 15) |
| Pig | GAATTCACAGGATCATATCCAGTACTGTT (SEQ ID NO: 16) | CAAGGACAAGTGCATTTCCATGAATCAGGA (SEQ ID NO: 17) | CAGAGAGC (SEQ ID NO: 18) | TCCTTGGCTCCCAACC (SEQ ID NO: 19) | TGTTGTCTTCCCATG (SEQ ID NO: 20) |
| Gerbil | CAGGACCTTGGGTCCA (SEQ ID NO: 21) | CAACAGCATTGCTAAAGC (SEQ ID NO: 22) | AGCAGATA (SEQ ID NO: 23) | TCACACAGACCCACGGAACCC (SEQ ID NO: 24) | TTGTCCTTCCACA (SEQ ID NO: 25) |
| Human | AGCGCAGGGCGGTAACTCTGGGCGGGGCTGGGCTCCA (SEQ ID NO: 26) | GGGCTGGACAGCACAGTCCCTCTGAACTGCA (SEQ ID NO: 27) | CAGAGACCTCGC (SEQ ID NO: 28) | AGGCCCCGAGAAC (SEQ ID NO: 29) | TGTCGCCCTTCCACG (SEQ ID NO: 30) |
| Consensus | GGA++++GGGGC+CATA+CCCA+ (SEQ ID NO: 31) | ACAGG+C+AGAACCCAT+GCCT+CCAT+AAT (SEQ ID NO: 32) | CAGA+A++AGA+ (SEQ ID NO: 33) | CTCCC+GGCTCC+A+CA++ (SEQ ID NO: 34) | TTGTCTTCCAT (SEQ ID NO: 35) |

*FIG. 8A*

Neonatal rat CMs transfected with
Luc-Ces1d or different Ces1d
5' UTR RNA elements modRNAs Measuring of Luc
signal with IVIS©

SYNTHETIC MODIFIED RNA AND USES THEREOF

This application is a national stage filing under 35 U.S.C. § 371 of International Application No. PCT/US2020/059482, filed on Nov. 6, 2020, and claims the priority benefit of U.S. Provisional Patent Application Ser. No. 62/932,255, filed Nov. 7, 2019, which applications are hereby incorporated by reference in their entireties.

This invention was made with government support under RO1 HL142768-01 awarded by National Institutes of Health. The government has certain rights in the invention.

FIELD

The present application relates to nucleic acid molecules and pharmaceutical compositions thereof, to methods involving the nucleic acid molecules and pharmaceutical compositions, and to methods of identifying a nucleic acid sequence capable of selectively enhancing translation of a heterologous protein of interest in a target cell.

BACKGROUND

Ischemic heart disease is the leading cause of death for both men and women in the U.S., killing about 610,000 people each year. Thus, it is desirable to devise novel treatments that improve cardiac function post-ischemic injury. One avenue of research into treating a failing heart post-myocardial infarction ("MI") is genetic medicine (Tilemann et al., "Gene Therapy for Heart Failure," Circ. Res. 110:777-793 (2012)), by which scientists aim to adjust gene expression in the heart using viral vectors, small molecules, or RNA-based approaches to promote cardiac protection as well as cardiovascular or cardiac regeneration in ischemic cardiac disease. Synthetic modified messenger RNA ("modRNA") is a novel gene therapy platform that can be used to alter protein levels in mammalian cells and tissues (Sultana et al., "Optimizing Cardiac Delivery of Modified mRNA," Mol. Ther. 25(6):1306-1315 (2017) and Hadas et al., "Optimizing Modified mRNA In Vitro Synthesis Protocol for Heart Gene Therapy," Mol. Ther. Methods Clin. Dev. 14(13):300-305 (2019)) and to treat cardiac disease (Zangi et al., "Modified mRNA Directs the Fate of Heart Progenitor Cells and Induces Vascular Regeneration after Myocardial Infarction," Nat. Biotechnol. 31:898-907 (2013); Magadum & Zangi, "mRNA-Based Protein Replacement Therapy for the Heart," Mol. Ther. 27:785-793 (20189); and Hadas et al., "Modified mRNA as a Therapeutic Tool to Induce Cardiac Regeneration in Ischemic Heart Disease," Wiley Interdiscip. Rev. Syst. Biol. Med. 9(1):e1367 (2017)). The concept of therapeutically altering mRNA expression has great potential to treat human diseases (Weissman & Kariko, "mRNA: Fulfilling the Promise of Gene Therapy," Mol. Ther. 23:1416-1417 (2015)). To date, several therapeutic approaches using siRNA and antisense oligonucleotides have been shown to reduce mRNA levels in cells (Bobbin & Rossi, "RNA Interference (RNAi)-Based Therapeutics: Delivering on the Promise?," Annu. Rev. Pharmacol. Toxicol. 56:103-122 (2016) and Stein & Castanotto, "FDA-Approved Oligonucleotide Therapies in 2017," Mol. Ther. 25(5):1069-1075 (2017)). Yet, protein upregulation in tissues is challenging, mostly due to the high amount of mRNA needed to treat human tissue. Supplying a large amount of mRNA in vivo can elicit undesirable immune responses to the administered mRNA. Preclinical studies have suggested that due to the transient expression of modRNA (target gene expression returns to baseline within 48-72 hours of administration), both directly and intravenously delivered modRNA will need to be administered multiple times to achieve desired levels of target gene expression (Zangi et al., "Modified mRNA Directs the Fate of Heart Progenitor Cells and Induces Vascular Regeneration after Myocardial Infarction," Nat. Biotechnol. 31:898-907 (2013); Pardi et al., "Expression Kinetics of Nucleoside-Modified mRNA Delivered in Lipid Nanoparticles to Mice by Various Routes," J. Control Release 217:345-351 (2015); Mahiny et al., "In Vivo Genome Editing Using Nuclease-Encoding mRNA Corrects SP-B Deficiency," Nat. Biotechnol. 33:584-586 (2015); Kormann et al., "Expression of Therapeutic Proteins after Delivery of Chemically Modified mRNA in Mice," Nat. Biotechnol. 29:154-157 (2011); and Zimmermann et al., "Successful Use of mRNA-Nucleofection for Overexpression of Interleukin-10 in Murine Monocytes/Macrophages for Anti-Inflammatory Therapy in a Murine Model of Autoimmune Myocarditis," J. Am. Heart Assoc. 1:e003293 (2012)). Thus, one obstacle in using modRNA for the treatment of cardiac ischemic disease is achieving high levels of target protein expression by direct administration of modRNA to the heart. It is also desirable to achieve high levels of target protein expression following a single administration of modRNA.

Gene expression is controlled intricately at the post-transcriptional level (Mignone et al., "Untranslated Regions of mRNAs," Genome Biol. 3(3):REVIEWS0004.1 (2002)). The level of any individual mRNA type inside a cell does not ensure that comparable amounts of respective proteins will be expressed (Vogel et al., "Sequence Signatures and mRNA Concentration Can Explain Two-Thirds of Protein Abundance Variation in a Human Cell Line," Mol. Syst. Biol. 6:400 (2010)). Both positive and negative modulators influence translation and maintain certain protein levels. Within the untranslated regions (UTRs) of the mRNA are multiple regulatory elements, which are critical for mRNA stability and translation into protein (Pfeiffer et al., "Using Translational Enhancers to Increase Transgene Expression in Drosophila," Proc. Natl. Acad. Sci. USA 109:6626-6631 (2012) and Wilkie et al., "Regulation of mRNA Translation by 5'- and 3'-UTR-Binding Factors," Trends Biochem. Sci. 28(4):182-188 (2003)). Eukaryotic gene translation is regulated at the translation level by several components, including the 5' untranslated region ("5' UTR") (Ong et al., "The Role of 5' Untranslated Region in Translational Suppression of OKL38 mRNA in Hepatocellular Carcinoma," Oncogene 26(8):1155-65 (2007); Leppek et al., "Functional 5' UTR mRNA Structures in Eukaryotic Translation Regulation and How to Find Them," Nat. Rev. Mol. Cell Biol. 19(3):158-174 (2018); and van der Velden & Thomas, "The Role of the 5' Untranslated Region of an mRNA in Translation Regulation During Development," Int. J. Biochem. Cell Biol. 31(1):87-106 (1999)), the 3' untranslated region ("3' UTR") (van Oers et al., "Role of the 3' Untranslated Region of Baculovirus p10 mRNA in High-Level Expression of Foreign Genes," J. Gen. Virol. 80(Pt 8):2253-2262 (1999); Thekkumkara et al., "Functional Role for the Angiotensin II Receptor (AT1A) 3'-Untranslated Region in Determining Cellular Responses to Agonist: Evidence for Recognition by RNA Binding Proteins," Biochem. J. 329(Pt 2):255-264 (1998); and Chen et al., "The Functional Role of the 3' Untranslated Region and Poly(A) Tail of Duck Hepatitis A Virus Type 1 in Viral Replication and Regulation of IRES-Mediated Translation," Front. Microbiol. 9:2250 (2018)), poly A tail (Chartier et al., "Mitochondrial Dysfunction Reveals the Role of mRNA Poly(A) Tail Regulation in Oculopharyngeal Muscular Dystrophy Pathogenesis," *PLoS Genet.* 11(3):e1005092 (2015); Crawford et al., "The Role of 3' Poly(A) Tail Metabolism in Tumor Necrosis Factor-Alpha Regulation," *J. Biol. Chem.* 272(34):21120-21127 (1997); Nie et al., "Sarcoplasmic Reticulum Ca2+ pump mRNA Stability in Cardiac and Smooth Muscle: Role of Poly A+ Tail Length," *Cell Calcium* 35(5):479-84 (2004); and Peng et al., "Characterization of the Role of Hexamer AGUAAA and Poly(A) Tail in Coronavirus Polyadenylation," *PLoS One* 11(10):e0165077 (2016)), and cap structure (Galloway & Cowling, "mRNA Cap Regulation in Mammalian Cell Function and Fate," *Biochim. Biophys. Acta* Gene Regul. Mech. 1862(3):270-279 (2019); Grudzien-Nogalska et al., "Synthesis of Anti-Reverse Cap Analogs (ARCAs) and Their Applications in mRNA Translation and Stability," *Methods Enzymol.* 431: 203-227 (2007); Meaux & Van Hoof, "Yeast Transcripts Cleaved by an Internal Ribozyme Provide New Insight Into the Role of the Cap and Poly(A) Tail in Translation and mRNA Decay," *RNA* 12(7):1323-1337 (2006); and Mukherjee et al., "Identification of Cytoplasmic Capping Targets Reveals a Role for Cap Homeostasis in Translation and mRNA Stability," *Cell Rep.* 2(3):674-684 (2012)).

Moreover, the length and secondary structure of the 5' UTR, as well as any mutations it contains, have been reported to be associated with certain human diseases (Chatterjee & Pal, "Role of 5'- and 3'-Untranslated Regions of mRNAs in Human Diseases," *Biol. Cell* 101(5):251-262 (2009)). The 5' UTR plays a significant role in regulating translation efficiency by helping the ribosome bind the messenger RNA ("mRNA") proximal to the start codon and thus is a main contributor to the cellular proteome (Hinnebusch et al., "Translational Control by 5'-Untranslated Regions of Eukaryotic mRNAs," *Science* 352(6292):1413-1416 (2016)). Additionally, certain RNA elements within the 5' UTR may change its secondary structure (e.g., internal ribosome entry sites (IRES), upstream AUGs, or open reading frames (uORFs)) and can be important contributors to the entire translation rate (Araujo et al., "Before It Gets Started: Regulating Translation at the 5' UTR," *Comp. Funct. Genomics* 2012:475731 (2012) and Dvir et al., "Deciphering the Rules by which 5'-UTR Sequences Affect Protein Expression in Yeast," *Proc. Natl. Acad. Sci. USA* 110(30):E2792-2801 (2013)). 5' UTRs can also contain sequence elements that can function as binding sites for regulatory proteins (Wilkie et al., "Regulation of mRNA Translation by 5'- and 3'-UTR-Binding Factors," *Trends Biochem. Sci.* 28(4):182-188 (2003)).

To date, the modRNA used in pre-clinical cardiac research has employed an artificial 5' UTR (36 nucleotides) that was first described by Warren et al., "Highly Efficient Reprogramming to Pluripotency and Directed Differentiation of Human Cells with Synthetic Modified mRNA," *Cell Stem Cell* 7(5):618-630 (2010). In vitro screening has been used to optimize mRNA 5' UTR and improve Arginase 1 (ARG1) expression (Asrani et al., "Optimization of mRNA Untranslated Regions for Improved Expression of Therapeutic mRNA," *RNA Biol.* 15(6):756-762 (2018)). However, plasmid-based screening methods do not necessarily correlate with protein expression driven by exogenously expressed mRNA (Asrani et al., "Optimization of mRNA Untranslated Regions for Improved Expression of Therapeutic mRNA," *RNA Biol.* 15(6):756-762 (2018)). Moreover, improved 5' UTR, but not 3' UTR, appears to be the key driver in protein expression for exogenously delivered mRNA (Asrani et al., "Optimization of mRNA Untranslated Regions for Improved Expression of Therapeutic mRNA," *RNA Biol.* 15(6):756-762 (2018)).

To this end, no screening approaches have been carried out to identify alternative 5' UTRs to improve mRNA translatability of in vitro synthesized modRNA constructs of therapeutic interest.

The present application is directed to overcoming these and other deficiencies in the art.

SUMMARY

One aspect of the present application relates to a nucleic acid molecule comprising a first nucleic acid sequence comprising at least a portion of a 5' untranslated region (5' UTR) of a carboxylesterase gene and a second nucleic acid sequence encoding a protein of interest, where the second nucleic acid sequence is heterologous to and operatively coupled to the first nucleic acid sequence.

Another aspect of the present application relates to a pharmaceutical composition comprising the nucleic acid molecule described herein.

A further aspect of the present application relates to a method of expressing a protein of interest in a target cell. This method involves providing a nucleic acid molecule or the pharmaceutical composition described herein and contacting a target cell with the nucleic acid molecule or pharmaceutical composition, where the nucleic acid molecule is translated to express the protein of interest in the target cell.

Another aspect of the present application relates to a method of treating a subject for cardiac ischemia or hepatic ischemia. This method involves providing the nucleic acid molecule or the pharmaceutical composition described herein and contacting the subject with the nucleic acid molecule or the pharmaceutical composition described herein, where the nucleic acid molecule is translated to express a protein of interest in the subject's heart or liver to treat the subject for cardiac ischemia or hepatic ischemia.

A further aspect of the present application relates to a method of identifying a 5' untranslated region (5' UTR) for selectively enhancing translation of a heterologous protein of interest in a target cell or tissue. This method involves obtaining a first sample of living tissue comprising a target cell under disease conditions and a second sample of living tissue comprising a target cell under non-disease conditions; quantifying genes that are transcribed and translated in the first and second samples; identifying a gene which is (i) transcribed at similar or lower levels in the first sample relative to the second sample and (ii) translated at higher levels in the first sample relative to the second sample; and identifying the 5' UTR of the identified gene, where the identified 5' UTR is capable of selectively enhancing translation of a heterologous protein of interest in a target cell or tissue.

Modified mRNA (modRNA) is a gene delivery platform for transiently introducing a single or several genes of interest to different cell types and tissues. modRNA is considered a safe vector for gene transfer as it negligibly activates the innate immune system and does not compromise genome integrity. Due to its clinical potential, modRNA use in basic and translational science is rising. It is desirable to use modRNA to induce cardiac regeneration post-ischemic injury. However, major obstacles in using modRNA for cardiac ischemic disease include the need to directly, singly administer modRNA to the heart and the inefficient translation of modRNA due to its short half-life. Modulating 5' untranslated regions (5' UTR) to enhance translation efficiency in ischemic cardiac disease can reduce the amount of modRNA needed per delivery by achieving higher and longer protein production post single delivery. Described herein is the identification of the 5' UTR from the fatty acid metabolism gene carboxylesterase 1D as capable of increasing modRNA-mediated translation in the heart post-myocardial infarction. The results presented herein specifically identify the Ces1d RNA element (Element D) as responsible for the enhanced modRNA translation post-ischemic injury in the heart. Importantly, the 5' UTR of Ces1d was found to enhance modRNA translation in the heart and liver, but not in the kidney, post-ischemic injury. These results suggest that the 5' UTR of Ces1d and Element D of Ces1d play a wider role in protein translation under ischemic conditions in different organs. These results also form the foundation for the nucleic acid molecules and pharmaceutical compositions described herein, methods involving the nucleic acid molecules and pharmaceutical compositions disclosed herein, and the methods of identifying a nucleic acid sequence capable of selectively enhancing translation of a heterologous protein of interest in a target cell described herein.

BRIEF DESCRIPTION OF THE DRAWINGS

FIGS. 1A-1G demonstrate the characterization of the ischemic heart transcriptome and proteome. FIG. 1A is a schematic diagram illustrating the experimental protocol used to prepare samples for RNAseq and proteomic analysis. Sham-operated or LAD-ligated hearts were collected 4-hours or 24-hours post-myocardial infarction (MI) and the ischemic area tissue (or equivalent area in sham-operated hearts) was divided into two equal pieces. One-half of the ischemic heart was sequenced for transcriptomic analysis (n=10 total, Sham n=3, 4-hours post-MI n=3, 24-hours post-MI n=4), while the other half of the ischemic heart was evaluated for protein level using mass spectrometry (n=12 total, Sham n=4, 4-hours post-MI n=4, 24-hours post-MI n=4). FIGS. 1B-1C are hierarchical clustering dendrograms of 2,272 genes with corresponding mRNA level (FIG. 1B) or 2,397 protein intensities (FIG. 1C) in Sham, 4-hours post-MI, or 24-hours post-MI hearts. FIGS. 1D-1E are graphs showing correlation analysis between changes in levels of proteins and mRNA in the LV 4-hours (FIG. 1D) or 24-hours (FIG. 1E) post-MI. The bottom right shaded rectangles in FIG. 1D and FIG. 1E include genes that show static or reduced mRNA levels post-MI while their encoded proteins level increased in comparison to Sham. FIGS. 1F-1G are tables showing a list of genes that encode for proteins with elevated protein levels (fold change>2), but lowered mRNA (fold change<0.64) 4-hours (FIG. 1F) or 24-hours (FIG. 1G) post-MI. Genes in the light shaded boxes have a 5' UTR that is shorter than 100 base pairs.

FIGS. 2A-2D show that RNAseq experimental groups are clustered together in a hierarchical clustering dendrogram and Ces1d western blot confirms RNAseq and proteomic expression results. FIG. 2A is a hierarchical clustering dendrogram of 14,000 genes that were sequenced for transcriptomic analysis from ischemic or non-ischemic heart tissues (n=10 total, Sham n=3, 4 hours post MI n=3 or 24 hours post MU n=4). FIG. 2B is a graph showing the results of a qPCR experiment used to evaluate Ces1d expression performed on samples taken 24 hours from hearts that have undergone Sham or MU surgery (n–3). FIG. 2C is a representative image of western blot analysis performed with anti-Ces1d antibody to evaluate protein samples taken 24 hours from hearts that have undergone Sham or MI surgery. FIG. 2D is a graph showing the quantification of the experiment shown in FIG. 2C (n=2). Unpaired two-tailed t-test for FIG. 2B and FIG. 2D. *, P<0.05.

FIG. 3A is a schematic illustration of the modRNA constructs evaluated in FIGS. 3B-3F. The illustration shows the replacement of a commonly used artificial 5' UTR (i.e., a control 5' UTR) with the 5' UTR of Gsn, Pzp, Serpina 1b, Fnk3, or Ces1d in a Luc modRNA reporter construct. FIG. 3B is a schematic diagram illustrating the experimental plan to evaluate the translation efficiency of Luc modRNA or GFP modRNA comprising the 5' UTRs from FIG. 3A in neonatal rat cardiomyocytes (CMs) using Interactive IVIS® or western blot analysis, respectively. FIGS. 3C-3D show the quantification of the IVIS® (FIG. 3C, n=4) and western blot (FIG. 3D) results described in FIG. 3B. FIG. 3E is a schematic diagram illustrating the experimental plan to use IVIS® analysis to evaluate the translation efficiency of Luc modRNA constructs comprising the 5' UTRs from FIG. 3A in mouse hearts 24-hours post-MI using IVIS® analysis. FIG. 3F is a graph showing the quantification of the IVIS® experiment described in FIG. 3E (n=4). One-way ANOVA, Tukey's Multiple Comparison Test for FIG. 3C and FIG. 3F. ***, P<0.001, *, P<0.05, N.S., Not Significant.

FIGS. 4A-4E demonstrate in vitro IVIS® analysis of Luc modRNA in neonatal rat CMs. FIG. 4A is a schematic diagram illustrating the experimental protocol for evaluating translation efficiency in neonatal rat CMs using Luc modRNA constructs (Luc-Control, Luc-Pzp, Luc-Gsn, Luc-Fn3k, Luc-Serpina 1b, Luc-Ces1d, and Renilla-Control) and IVIS® analysis. FIGS. 4B-4C show representative IVIS® analysis images of the luciferase (Luc) signal (FIG. 4B) and Renilla signal (FIG. 4C) from the experiment described in FIG. 4A. FIGS. 4D-4E are graphs showing the quantification of the experimental results shown in FIGS. 4B-4C, respectively.

FIG. 5A is a schematic diagram illustrating the experimental protocol used to evaluate the translation efficiency of Luc modRNA comprising the 5' UTR of Ces1d (Luc-Ces1d) or an artificial control 5' UTR (Luc-Control) in a non-ischemic heart model. FIG. 5B is a graph quantifying the Luc signal observed 24 hours, 48 hours, and 72 hours following injection with Luc-Ces1d modRNA and Luc-Control modRNA following the protocol of FIG. 5A (n=15). FIG. 5C is a schematic diagram illustrating the experimental protocol used to evaluate the translation efficiency of Luc modRNA comprising the 5' UTR of Ces1d (Luc-Ces1d) or an artificial control 5' UTR (Luc-Control) in an ischemic heart model. FIG. 5D is a graph showing quantification of the Luc signal observed 24 hours, 48 hours, and 72 hours following LED ligation and modRNA injection with Luc-Ces1d modRNA and Luc-Control modRNA following the protocol of FIG. 5C (n=15). Two-way ANOVA, Tukey's Multiple Comparison Test for FIG. 5B & FIG. 5D. *, P<0.05, N.S., Not Significant.

FIGS. 6A-6F demonstrate the translation efficiency of Luc-modRNA constructs comprising the 5' UTR of Ces1d (Luc-Ces1d) and an artificial control 5' UTR (Luc-Control) in ischemic heart, kidney, and liver mouse models. FIG. 6A is a schematic diagram illustrating the experimental protocol used to evaluate the translation efficiency of Luc modRNA comprising the 5' UTR of Ces1d (Luc-Ces1d) or an artificial control 5' UTR (Luc-Control) in an ischemic heart mouse model. FIG. 6B shows representative IVIS® imaging results of the experiment described in FIG. 6A. FIG. 6C is a schematic diagram illustrating the experimental protocol used to evaluate the translation efficiency of Luc modRNA comprising the 5' UTR of Ces1d (Luc-Ces1d) or an artificial control 5' UTR (Luc-Control) in an ischemic liver mouse model. FIG. 6D shows a representative IVIS® image from the experiment described in FIG. 6C. FIG. 6E is a schematic diagram illustrating the experimental protocol used to evaluate the translation efficiency of Luc modRNA comprising the 5' UTR of Ces1d (Luc-Ces1d) or an artificial control 5' UTR (Luc-Control) in an ischemic kidney mouse model. FIG. 6F shows a representative IVIS® image of the experiment described in FIG. 6E.

FIG. 7A is a schematic diagram illustrating the experimental protocol used to evaluate the translation efficiency of Luc modRNA comprising the 5' UTR of Ces1d (Luc-Ces1d) or an artificial control 5' UTR (Luc-Control) in a non-ischemic liver model. FIG. 7B is a graph showing quantification of the experiment described in FIG. 7A (n=6). FIG. 7C is a schematic diagram illustrating the experimental protocol used to evaluate the translation efficiency of Luc modRNA comprising the 5' UTR of Ces1d (Luc-Ces1d) or an artificial control 5' UTR (Luc-Control) in an ischemic liver model. FIG. 7D is a graph showing quantification of the experiment described in FIG. 7C (n=6). FIG. 7E is a schematic diagram illustrating the experimental plan to evaluate the translation efficiency of Luc modRNA comprising the 5' UTR of Ces1d (Luc-Ces1d) or an artificial control 5' UTR (Luc-Control) in a non-ischemic kidney model. FIG. 7F is a graph showing quantification of the experiment described in FIG. 7E (n=6). FIG. 7G is a schematic diagram illustrating the experimental protocol used to evaluate the translation efficiency of Luc modRNA comprising the 5' UTR of Ces1d (Luc-Ces1d) or an artificial control 5' UTR (Luc-Control) in an ischemic kidney model. FIG. 7H is a graph showing quantification of the experiment described in FIG. 7G (n=6). Two-way ANOVA, Tukey's Multiple Comparison Test for FIGS. 7B, 7D, 7F, and 7H. *, $P < 0.05$, N.S., Not Significant.

FIGS. 8A-8E demonstrate that a specific RNA element in the 5' UTR of Ces1d significantly enhances Luc modRNA translation in an ischemic heart mouse model. FIG. 8A is a table listing elements of the 5' UTR of Ces1d that have been conserved among various species (Elements A-E). FIG. 8B is a schematic diagram illustrating the experimental protocol used to evaluate the translation efficiency of Luc modRNA constructs comprising the RNA elements identified in FIG. 8A (i.e., Luc-Element A, Luc-Element B, Luc-Element C, Luc-Element D, and Luc-Element E) as well as a Luc modRNA construct comprising the 5' UTR of Ces1d (Luc-Ces1d) in neonatal rat CMs using IVIS® analysis. FIG. 8C is a graph showing quantification of the experiment described in FIG. 8B (n=4). FIG. 8D is a schematic diagram illustrating the experimental protocol used to evaluate the translation efficiency of Luc-modRNA constructs comprising an artificial control 5' UTR (Luc-Control), the full-length 5' UTR of Ces1d (Luc-Ces1d), or Element D of the 5' UTR of Ces1d (Luc-Element D) in an ischemic heart model. FIG. 8E is a graph showing quantification of the experiment described in FIG. 8D (n=5). One-way ANOVA, Tukey's Multiple Comparison Test for FIG. 8C. Two-way ANOVA, Tukey's Multiple Comparison Test for FIG. 8E. *, $P < 0.001$, , $P < 0.01$, *, $P < 0.05$, N.S., Not Significant.

FIG. 9A is a schematic diagram illustrating the experimental protocol used to evaluate the translation efficiency of Luc modRNA comprising the full-length 5' UTR of Ces1d or Element D of the 5' UTR of Ces1d in an ischemic liver mouse model. FIG. 9B is a graph showing quantification of the experiments described in FIG. 9A (n=4). Two-way ANOVA, Tukey's Multiple Comparison Test. N.S., Not Significant.

FIG. 10A is a schematic diagram illustrating the experimental protocol used to evaluate the translation efficiency of Luc modRNA carrying the full length 5' UTR of Ces1d or the control 5' UTR insert in a heart non-ischemic mouse model. FIG. 10B is a graph showing quantification of the experiment described in FIG. 10A using IVIS® analysis. Two-way ANOVA, Turkey's Multiple Comparison Test. N.S., not significant.

DETAILED DESCRIPTION

Figure 1A:
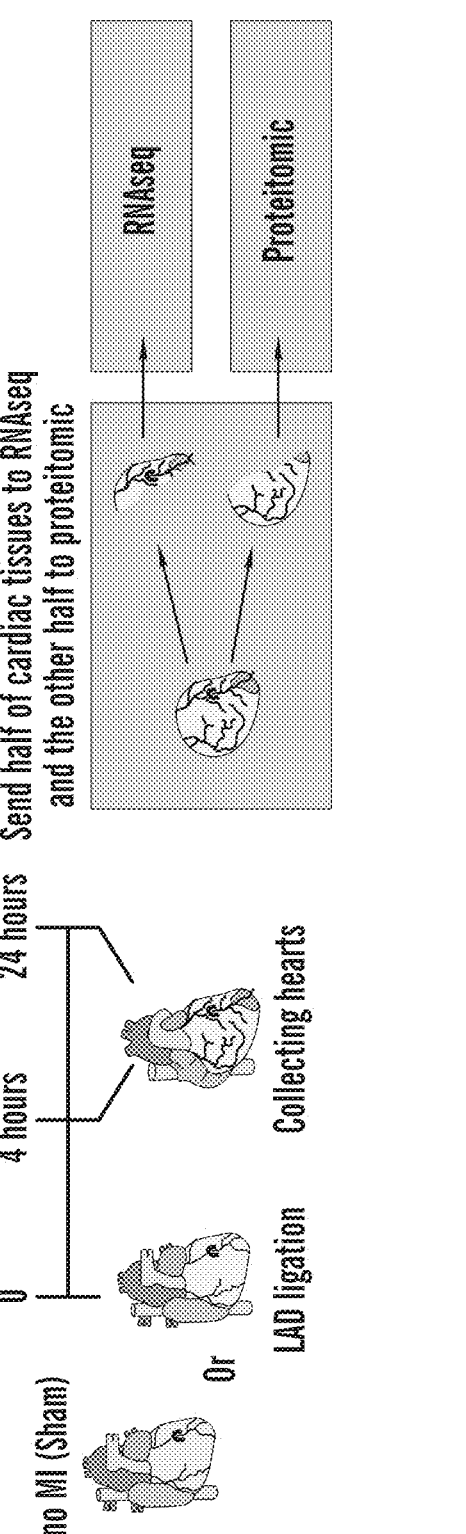

The present application relates to the identification of nucleic acid regions that enhance the translation efficiency of a target protein. Disclosed herein are nucleic acid molecules comprising at least a portion of a 5' untranslated region (5' UTR) of an identified gene and pharmaceutical compositions comprising the same.

As used herein, the singular forms "a", "an", and "the" include plural reference unless the context clearly dictates otherwise.

Unless defined otherwise, all technical and scientific terms used herein have the same meaning as commonly understood to one of ordinary skill in the art to which this disclosure belongs.

A first aspect of the present application relates to a nucleic acid molecule comprising a first nucleic acid sequence comprising at least a portion of a 5' untranslated region (5' UTR) of a carboxylesterase gene and a second nucleic acid sequence encoding a protein of interest, where the second nucleic acid sequence is heterologous to and operatively coupled to the first nucleic acid sequence.

As used herein, the term "operably coupled" refers to the sequential and function arrangement between a 5' UTR and a nucleic acid encoding a protein of interest, where the 5' UTR modulates translation of a nucleic acid sequence encoding a protein of interest.

As used herein, the term "nucleoside" refers to a molecule comprising a nitrogenous base (i.e., a nucleobase) linked to a pentose (e.g., deoxyribose or ribose) sugar. Typical nitrogenous bases which form nucleosides include adenine, guanine, cytosine, 5-methyl cytosine, uracil, and thymine. Suitable ribonucleosides (which comprise ribose as the pentose sugar) include, e.g., adenosine (A), guanosine (G), 5-methyluridine (m⁵U), uridine (U), and cytidine (C).

As used herein, the term "nucleotide" refers to a molecule comprising a nucleoside (e.g., a ribonucleoside) and a phosphate group. Ribonucleotides include, e.g., adenosine monophosphate, adenosine diphosphate, adenosine triphosphate, guanosine monophosphate, guanosine diphosphate, guanosine triphosphate, cytidine monophosphate, cytidine diphosphate, cytidine triphosphate, uridine monophosphate, uridine diphosphate, uridine triphosphate, and derivatives thereof.

As used herein, the term "messenger RNA" (also, mRNA) refers to a ribonucleotide sequence that encodes a protein of interest and can be translated to produce the encoded protein of interest in vitro, in vivo, in situ, or ex vivo.

As used herein, the term "modified" or "mod" in reference to RNA refers to an alteration of a ribonucleotide that can be, for example, incorporated into an mRNA molecule. Modifications to an mRNA molecule can include, for example and without limitation, physical or chemical modifications to a base, such as, for example and without limitation, the depletion of a base or a chemical modification of a base (see, e.g., U.S. Pat. No. 8,278,036 to Kariko et al.; U.S. Pat. No. 10,086,043 to Chien et al.; and U.S. Patent Application Publication No. 2019/0203226 to Zangi et al., which are hereby incorporated by reference in their entirety).

In some embodiments, the first and second nucleic acids are ribonucleic acids. In certain embodiments, the first and second nucleic acids are mRNAs. In certain other embodiments, the first and second nucleic acids are modified mRNAs (modRNAs).

modRNAs can be prepared as described in, for example, U.S. Pat. No. 8,278,036 to Kariko et al.; Sultana et al., "Optimizing Cardiac Delivery of Modified mRNA," *Mol. Ther.* 25(6):1306-1315 (2017); and Hadas et al., "Optimizing Modified mRNA In Vitro Synthesis Protocol for Heart Gene Therapy," *Mol. Ther. Methods Clin. Dev.* 14(13):300-305 (2019), which are hereby incorporated by reference in their entirety. In some embodiments, modRNA is generated by in vitro transcription. The modRNA may be in vitro transcribed, e.g., from a linear DNA template using one or more reagents selected from the group consisting of a cap analog, guanosine triphosphate, adenosine triphosphate, cytidine triphosphate, uridine triphosphate, and derivatives thereof (Hadas et al., "Optimizing Modified mRNA In Vitro Synthesis Protocol for Heart Gene Therapy," *Mol. Ther. Methods Clin. Dev.* 14(13):300-305 (2019), which is hereby incorporated by reference in its entirety).

The cap analog may be selected from Anti-Reverse Cap Analog (ARCA) 3'-O-Me-m⁷G(5')ppp(5')G (Hadas et al., "Optimizing Modified mRNA In Vitro Synthesis Protocol for Heart Gene Therapy," *Mol. Ther. Methods Clin. Dev.* 14(13):300-305 (2019), which is hereby incorporated by reference in its entirety), standard cap analog m⁷G(5')ppp(5')G, unmethylated cap analog G(5')ppp(5')G, methylated cap analog for A+1 sites m⁷G(5')ppp(5')A, and unmethylated cap analog for A+1 sites G(5')ppp(5')A. In certain embodiments, the cap analog is Anti-Reverse Cap Analog (ARCA) 3'-O-Me-m⁷G(5')ppp(5')G.

Suitable derivatives of guanosine triphosphate, adenosine triphosphate, cytidine triphosphate, and uridine triphosphate are well known in the art and include, e.g., modifications to the ribonucleoside. Ribonucleosides can, for example, be modified to produce modRNAs having, e.g., increased stability and/or clearance in tissues, improved receptor uptake and/or kinetics, improved cellular access by the nucleic acid molecules, improved engagement with translational machinery, improved mRNA half-life, increased translation efficiency, improved immune evasion, improved protein production capacity, improved secretion efficiency, improved accessibility to circulation, improved protein half-life and/or modulation of a cell's status, improved function, improved activity, or for any other reason.

According to some embodiments, modRNA is in vitro transcribed from a plasmid template using one or more reagents selected from the group consisting of 3'-O-Me-m7G(5')ppp(5')G, guanosine triphosphate, adenosine triphosphate, cytidine triphosphate, and N1-methylpseudouridine-5-triphosphate. Thus, in certain embodiments of the invention disclosed herein, the modRNAs comprise N1-methylpseudouridine. In other embodiments, the modRNAs comprise pseudouridine or methylpseudouridine.

Additional suitable modifications to a modRNA or mRNA molecule are well known in the art (see, e.g., U U.S. Pat. No. 8,278,036 to Kariko et al.; U.S. Pat. No. 10,086,043 to Chien et al.; U.S. Patent Application Publication No. 2019/0203226 to Zangi et al.; and U.S. Patent Application Publication No. 2018/0353618 to Burkhardt et al., which are hereby incorporated by reference in their entirety). In some embodiments, the nucleoside that is modified in the modRNA is a uridine (U), a cytidine (C), an adenine (A), or guanine (G). The modified nucleoside can be, for example, m⁵C (5-methylcytidine), m⁶A (N⁶-methyladenosine), s²U (2-thiouridien), ψ (pseudouridine), or Um (2-O-methyluridine). Some exemplary chemical modifications of nucleosides in the modRNA molecule may further include, for example and without limitation, pyridine-4-one ribonucleoside, 5-aza-uridine, 2-thio-5-aza uridine, 2-thiouridine, 4-thio pseudouridine, 2-thio pseudouridine, 5-hydroxyuridine, 3-methyluridine, 5-carboxymethyl uridine, 1-carboxymethyl pseudouridine, 5-propynyl uridine, 1-propynyl pseudouridine, 5-taurinomethyluridine, 1-taurinomethyl pseudouridine, 5-taurinomethyl-2-thio uridine, 1-taurinomethyl-4-thio uridine, 5-methyl uridine, 1-methyl pseudouridine, 4-thio-1-methyl pseudouridine, 2-thio-1-methyl pseudouridine, 1-methyl-1-deaza pseudouridine, 2-thio-1-methyl-1-deaza pseudouridine, dihydrouridine, dihydropseudouridine, 2-thio dihydrouridine, 2-thio dihydropseudouridine, 2-methoxyuridine, 2-methoxy-4-thio uridine, 4-methoxy pseudouridine, 4-methoxy-2-thio pseudouridine, 5-aza cytidine, pseudoisocytidine, 3-methyl cytidine, N4-acetylcytidine, 5-formylcytidine, N4-methylcytidine, 5-hydroxymethylcytidine, 1-methyl pseudoisocytidine, pyrrolo-cytidine, pyrrolo-pseudoisocytidine, 2-thio cytidine, 2-thio-5-methyl cytidine, 4-thio pseudoisocytidine, 4-thio-1-methyl pseudoisocytidine, 4-thio-1-methyl-1-deaza pseudoisocytidine, 1-methyl-1-deaza pseudoisocytidine, zebularine, 5-aza zebularine, 5-methyl zebularine, 5-aza-2-thio zebularine, 2-thio zebularine, 2-methoxy cytidine, 2-methoxy-5-methyl cytidine, 4-methoxy pseudoisocytidine, 4-methoxy-1-methyl pseudoisocytidine, 2-aminopurine, 2,6-diaminopurine, 7-deaza adenine, 7-deaza-8-aza adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, $N^6$-methyladenosine, $N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, $N^6$-threonyl-carb amoyladenosine, 2-methylthio-$N^6$-threonyl carbamoy-ladenosine, $N^6$,$N^6$-dimethyladenosine, 7-methyladenine, 2-methylthio adenine, 2-methoxy adenine, inosine, 1-methyl inosine, wyosine, wybutosine, 7-deaza guanosine, 7-deaza-8-aza guanosine, 6-thio guanosine, 6-thio-7-deaza guanos-ine, 6-thio-7-deaza-8-aza guanosine, 7-methyl guanosine, 6-thio-7-methyl guanosine, 7-methylinosine, 6-methoxy guanosine, 1-methylguanosine, $N^2$-methylguanosine, $N^2$,$N^2$-dimethylguanosine, 8-oxo guanosine, 7-methyl-8-oxo guanosine, 1-methyl-6-thio guanosine, $N^2$-methyl-6-thio guanosine, or $N^2$,$N^2$-dimethyl-6-thio guanosine.

In one embodiment, the modifications made to the modRNA are independently selected from the group con-sisting of 5-methylcytosine, pseudouridine, and 1-methylp-seudouridine.

In some embodiments, the modRNA comprises a modi-fied uracil selected from the group consisting of pseudou-ridine (w), pyridine-4-one ribonucleoside, 5-aza uridine, 6-aza uridine, 2-thio-5-aza uridine, 2-thio uridine (s2U), 4-thio uridine (s4U), 4-thio pseudouridine, 2-thio pseudou-ridine, 5-hydroxy uridine (ho$^5$U), 5-aminoallyl uridine, 5-halo uridine (e.g., 5-iodom uridine or 5-bromo uridine), 3-methyl uridine (m$^3$U), 5-methoxy uridine (mo$^5$U), uridine 5-oxyacetic acid (cmo$^5$U), uridine 5-oxyacetic acid methyl ester (mcmo$^5$U), 5-carboxymethyl uridine (cm$^5$U), 1-car-boxymethyl pseudouridine, 5-carboxyhydroxymethyl uri-dine (chm$^5$U), 5-carboxyhydroxym ethyl uridine methyl ester (mchm$^5$U), 5-methoxycarbonylmethyl uridine (mcm$^5$U), 5-methoxycarbonylmethyl-2-thio uridine (mcm$^5$s2U), 5-aminomethyl-2-thio uridine (nm$^5$s2U), 5-methylaminomethyl uridine (mnm$^5$U), 5-methylaminom-ethyl-2-thio uridine (mnm$^5$s2U), 5-methylaminomethyl-2-seleno uridine (mnm$^5$se$^2$U), 5-carbamoylmethyl uridine (ncm$^5$U), 5-carboxymethylaminomethyl uridine (cmnm$^5$U), 5-carboxymethylaminomethyl-2-thio uridine (cmnm$^5$s2U), 5-propynyl uridine, 1-propynyl pseudouridine, 5-taurinom-ethyl uridine (Tcm$^5$U), 1-taurinomethyl pseudouridine, 5-taurinomethyl-2-thio uridine ($^{TM5}$s2U), 1-taurinomethyl-4-thio pseudouridine, 5-methyl uridine (m$^5$U, e.g., having the nucleobase deoxythymine), 1-methyl pseudouridine (m$^1$ψ), 5-methyl-2-thio uridine (m$^5$s2U), 1-methyl-4-thio pseudouridine (m$_1$s$^4$ψ), 4-thio-1-methyl pseudouridine, 3-methyl pseudouridine (m$^3$ψ), 2-thio-1-methyl pseudouri-dine, 1-methyl-1-deaza pseudouridine, 2-thio-1-methyl-1-deaza pseudouridine, dihydrouridine (D), dihydropseudou-ridine, 5,6-dihydrouridine, 5-methyl dihydrouridine (m$^5$D), 2-thio dihydrouridine, 2-thio dihydropseudouridine, 2-methoxy uridine, 2-methoxy-4-thio uridine, 4-methoxy pseudouridine, 4-methoxy-2-thio pseudouridine, N$^1$-methyl pseudouridine, 3-(3-amino-3-carboxypropyl) uridine (acp$^3$U), 1-methyl-3-(3-amino-3-carboxypropyl) pseudouri-dine (acp$^3$ψ), 5-(isopentenylaminomethyl) uridine (inm$^5$U), 5-(isopentenylaminomethyl)-2-thio uridine (inm$^5$s2U), α-thio uridine, 2'-O-methyl uridine (Um), 5,2'-O-dimethyl uridine (m$^5$Um), 2'-O-methyl pseudouridine (vm), 2-thio-2'-O-methyl uridine (s2Um), 5-methoxycarbonylmethyl-2'-O-methyl uridine (mcm$^5$Um), 5-carbamoylmethyl-2'-O-methyl uridine (ncm$^5$Um), 5-carboxymethylaminomethyl-2'-O-methyl uridine (cmnm$^5$Um), 3,2'-O-dimethyl uridine (m$^3$Um), 5-(isopentenylaminomethyl)-2'-O-methyl uridine (inm$^5$Um), 1-thio uridine, deoxythymidine, 2'-F-ara uridine, 2'-F uridine, 2'-OH-ara uridine, 5-(2-carbomethoxyvinyl) uridine, and 5-3-(1-E-propenylamino) uridine.

In some embodiments, the modRNA comprises a modi-fied cytosine selected from the group consisting of 5-aza cytidine, 6-aza cytidine, pseudoisocytidine, 3-methyl cyti-dine (m$^3$C), $N^4$-acetyl cytidine (act), 5-formyl cytidine (f$^5$C), $N^4$-methyl cytidine (m$^4$C), 5-methyl cytidine (m$^5$C), 5-halo cytidine (e.g., 5-iodo cytidine), 5-hydroxymethyl cytidine (hm$^5$C), 1-methyl pseudoisocytidine, pyrrolo-cyti-dine, pyrrolo-pseudoisocytidine, 2-thio cytidine (s2C), 2-thio-5-methyl cytidine, 4-thio pseudoisocytidine, 4-thio-1-methyl pseudoisocytidine, 4-thio-1-methyl-1-deaza pseu-doisocytidine, 1-methyl-1-deaza pseudoisocytidine, zebu-larine, 5-aza zebularine, 5-methyl zebularine, 5-aza-2-thio zebularine, 2-thio zebularine, 2-methoxy cytidine, 2-methoxy-5-methyl cytidine, 4-methoxy pseudoisocyti-dine, 4-methoxy-1-methyl pseudoisocytidine, lysidine (k$^2$C), alpha-thio cytidine, 2'-O-methyl cytidine (Cm), 5,2'-O-dimethyl cytidine (m$^5$Cm), $N^4$-acetyl-2'-O-methyl cyti-dine (ac$^4$Cm), $N^4$,2'-O-dimethyl cytidine (m$^4$Cm), 5-formyl-2'-O-methyl cytidine (f$^5$Cm), $N^4$,$N^4$,2'-O-trimethyl cytidine (m$^4_2$Cm), 1-thio cytidine, 2'-F-ara cytidine, 2'-F cytidine, and 2'-OH-ara cytidine.

In some embodiments, the modRNA comprises a modi-fied adenine selected from the group consisting of 2-amino purine, 2,6-diamino purine, 2-amino-6-halo purine (e.g., 2-amino-6-chloro purine), 6-halo purine (e.g., 6-chloro purine), 2-amino-6-methyl purine, 8-azido adenosine, 7-deaza adenine, 7-deaza-8-aza adenine, 7-deaza-2-amino purine, 7-deaza-8-aza-2-amino purine, 7-deaza-2,6-diamino purine, 7-deaza-8-aza-2,6-diamino purine, 1-methyl adenos-ine (m'A), 2-methyl adenine (m$^2$A), $N^6$-methyl adenosine (m$^6$A), 2-methylthio-$N^6$-methyl adenosine (ms$^2$ m$^6$A), $N^6$-isopentenyl adenosine (i$^6$A), 2-methylthio-$N^6$-isopente-nyl adenosine (ms$^2$i$^6$A), $N^6$-(cis-hydroxyisopentenyl) adenosine (io$^6$A), 2-methylthio-$N^6$-(cis-hydroxyisopente-nyl) adenosine (ms$^2$io$^6$A), $N^6$ glycinylcarbamoyl adenosine (g$^6$A), $N^6$-threonylcarbamoyl adenosine (t$^6$A), $N^6$-methyl-$N^6$-threonylcarbamoyl adenosine (m$^6_2$A), 2-methylthio-$N^6$-threonylcarbamoyl adenosine (ms$^2$g$^6$A), $N^6$,$N^6$-dimethyl adenosine (m$^6_2$A), $N^6$-hydroxynorvalylcarbamoyl adenos-ine (hn$^6$A), 2-methylthio-$N^6$-hydroxynorvalylcarbamoyl adenosine (ms$^2$hn$^6$A), $N^6$-acetyl adenosine (ac$^6$A), 7-methyl adenine, 2-methylthio adenine, 2-methoxy adenine, alpha-thio adenosine, 2'-O-methyl adenosine (Am), $N^6$,2'-O-dim-ethyl adenosine (m$^6$Am) $N^6$,$N^6$,2'-O-trimethyl adenosine (m$^6_2$Am), 1,2'-O-dimethyl adenosine (m$^1$Am), 2'-O-ribosyl adenosine (phosphate) (Ar(p)), 2-amino-$N^6$-methyl purine, 1-thio adenosine, 8-azido adenosine, 2'-F-ara adenosine, 2'-F adenosine, 2'-OH-ara adenosine, and $N^6$-(19-amino-pentaoxananonadecyl) adenosine.

In some embodiments, the modRNA comprises a modi-fied guanine selected from the group consisting of inosine (I), 1-methyl inosine (m'I), wyosine (imG), methylwyosine (mimG), 4-demethyl wyosine (imG-14), isowyosine (imG2), wybutosine (yW), peroxywybutosine (o$_2$yW), hydroxywybutosine (OHyW), undermodified hydroxywy-butosine (OHyWy), 7-deaza guanosine, queuosine (Q), epoxyqueuosine (oQ), galactosyl queuosine (galQ), manno-syl queuosine (manQ), 7-cyano-7-deaza guanosine (preQ$_0$), 7-aminomethyl-7-deaza guanosine (preQ$_1$), archaeosine (G$^+$), 7-deaza-8-aza guanosine, 6-thio guanosine, 6-thio-7-deaza guanosine, 6-thio-7-deaza-8-aza guanosine, 7-methyl guanosine (m$^7$G), 6-thio-7-methyl guanosine, 7-methyl inosine, 6-methoxy guanosine, 1-methyl guanosine (m$^1$G), $N^2$-methyl-guanosine (m$^2$G), $N^2$,$N^2$-dimethyl guanosine (m$^2_2$G), $N^{2,7}$-dimethyl guanosine (m$^{2,7}$G), $N^2$,$N^{2,7}$-dimethyl guanosine (m$^{2,2,7}$G), 8-oxo guanosine, 7-methyl-8-oxo guanosine, 1-methio guanosine, $N^2$-methyl-6-thio guanosine, $N^2,N^2$-dimethyl-6-thio guanosine, alpha-thio guanosine, 2'-O-methyl guanosine (Gm), $N^2$-methyl-2'-O-methyl guanosine ($m^2$Gm), $N^2,N^2$-dimethyl-2'-O-methyl guanosine ($m^2_2$Gm), 1-methyl-2'-O-methyl guanosine ($m^1$Gm), $N^{2,7}$-dimethyl-2'-O-methyl guanosine ($m^{2,7}$Gm), 2'-O-methyl inosine (1m), 1,2'-O-dimethyl inosine ($m^1$Gm), 2'-O-ribosyl guanosine (phosphate) (Gr(p)), 1-thio guanosine, $O^6$-methyl guanosine, 2'-F-ara guanosine, and 2'-F guanosine.

modRNA may include, for example, a non-natural or modified nucleotide. The non-natural or modified nucleotide may include, for example, a backbone modification, sugar modification, or base modification. The non-natural or modified nucleotide may include, for example, a base modification. In some embodiments, the base modification is selected from the group consisting of 2-amino-6-chloropurine riboside 5' triphosphate, 2-aminoadenosine 5' triphosphate, 2-thiocytidine 5' triphosphate, 2-thiouridine 5' triphosphate, 4-thiouridine 5' triphosphate, 5-aminoallylcytidine 5' triphosphate, 5-aminoallyluridine 5' triphosphate, 5-bromocytidine 5' triphosphate, 5-bromouridine 5' triphosphate, 5-iodocytidine 5' triphosphate, 5-iodouridine 5' triphosphate, 5-methylcytidine 5' triphosphate, 5-methyluridine 5' triphosphate, 6-azacytidine 5' triphosphate, 6-azauridine 5' triphosphate, 6-chloropurine riboside 5'-triphosphate, 7-deazaadenosine 5' triphosphate, 7-deazaguanosine 5' triphosphate, 8-azaadenosine 5' triphosphate, 8-azidoadenosine 5' triphosphate, benzimidazole riboside 5' triphosphate, $N^1$-methyladenosine 5' triphosphate, $N^1$-methylguanosine 5' triphosphate, $N^6$-methyladenosine 5' triphosphate, $O^6$-methylguanosine 5' triphosphate, $N^1$-methyl-pseudouridine 5' triphosphate, puromycin 5'-triphosphate, and xanthosine 5' triphosphate. Thus, according to some embodiments, the modRNA comprises $N^1$-methyl-pseudouridine 5' triphosphate.

Other modifications include, for example, those described in Tavernier et al., "mRNA as Gene Therapeutic: How to Control Protein Expression," *J. Control. Release* 150(3):238-247 (2011); Anderson et al., "Nucleoside Modifications in RNA Limit Activation of 2'-5'-Oligoadenylate Synthetase and Increase Resistance to Cleavage by RNase L," *Nucleic Acids Res.* 39(21):9329-9338 (2011); Kormann et al., "Expression of Therapeutic Proteins After Delivery of Chemically Modified mRNA in Mice," *Nat. Biotechnol.* 29(2):154-157 (2011); Kariko et al., "Incorporation of Pseudouridine into mRNA Yields Superior Nonimmunogenic Vector with Increased Translational Capacity and Biological Stability," *Mol. Ther.* 16(11):1833-1840 (2008); Kariko et al., "Suppression of RNA Recognition by Toll-Like Receptors: The Impact of Nucleoside Modification and the Evolutionary Origin of RNA," *Immunity* 23(2):165-175 (2005); and Warren et al., "Highly Efficient Reprogramming to Pluripotency and Directed Differentiation of Human Cells with Synthetic Modified mRNA," *Cell Stem Cell* 7(5):618-630 (2010), which are hereby incorporated by reference in their entirety.

In some embodiments, the modRNA comprises a modified nucleoside selected from the group consisting of $m^5$C, $m^5$U, $m^6$A, $s^2$U, Ψ, or 2'-O-methyl-U.

As used herein, the term "untranslated region" or "UTR" refers to a transcribed but untranslated region of a mRNA molecule. The 5' UTR starts at the transcription start site and continues to the start codon but does not include the start codon; whereas, the 3' UTR starts immediately following the stop codon and continues until the transcriptional termination signal. Natural 5' UTRs help translation initiation (Ong et al., "The Role of 5' Untranslated Region in Translational Suppression of OKL38 mRNA in Hepatocellular Carcinoma," *Oncogene* 26(8):1155-65 (2007); Leppek et al., "Functional 5' UTR mRNA Structures in Eukaryotic Translation Regulation and How to Find Them," *Nat. Rev. Mol. Cell Biol.* 19(3):158-174 (2018); and van der Velden & Thomas, "The Role of the 5' Untranslated Region of an mRNA in Translation Regulation During Development," *Int. J. Biochem. Cell Biol.* 31(1):87-106 (1999), which are hereby incorporated by reference in their entirety), and may comprise features such as, e.g., Kozak sequences, which facilitate translation initiation by the ribosome for many genes.

As demonstrated by the Examples below, modRNA constructs comprising the 5' UTR of, e.g., a mammalian carboxylesterase gene enhances the translation efficiency of a protein of interest as compared to modRNA constructs comprising a reference (i.e., an artificial control) 5' UTR sequence. Hence, in a first aspect, the present application relates to a nucleic acid molecule comprising a first nucleic acid sequence comprising at least a portion of a 5' UTR of a carboxylesterase gene and a second nucleic acid sequence encoding a protein of interest, where the second nucleic acid sequence is heterologous to and operatively coupled to the first nucleic acid sequence.

According to some embodiments, the carboxylesterase gene is a mammalian carboxylesterase gene. Suitable mammalian carboxylesterase genes and their corresponding 5' UTR sequences (i.e., SEQ ID NO:1 (mouse), SEQ ID NO:2 (rat), SEQ ID NO:3 (pig), SEQ ID NO:4 (gerbil), SEQ ID NO:5 (human), and SEQ ID NO:6 (monkey)) are shown in Table 1 below.

TABLE 1

| Mammalian Carboxylesterase Genes | | | |
|---|---|---|---|
| Name | Species | 5' UTR Sequence† | SEQ ID NO: |
| carboxyl-esterase 1D (Ces1d) | *Mus musculus* (Mouse) | AGGAGGCGGGTCCCCTGGTCCACAACAGAAGCATT GCTAAAGCAGCAGATAGCTCAGAGACCCACAGAGC CCTTGTCCTTCCACA (GenBank Accession No. NM_053200.2, positions 1-85) | 1 |
| | *Rattus norvegicus* (Rat) | TGCTAAAGGAACAAATAGCCCACAGATCCACAGAA CCCTTGTCCTTCCACA (GenBank Accession No. NM_133295.3, positions 1-51) | 2 |

TABLE 1-continued

| | | | SEQ ID |
|---|---|---|---|
| Name | Species | 5' UTR Sequence[†] | NO: |

Mammalian Carboxylesterase Genes

| Name | Species | 5' UTR Sequence[†] | SEQ ID NO: |
|---|---|---|---|
| | *Cavia porcellus* (Pig) | GAATTCACAGGATCATATCCAGTACTGTTCAAGGA CAAGTGCATTTCCATGAATCAGGACAGAGAGCTCC TTGGCTCCAACCTGTTGTCTTCCCATG (GenBank Accession No. NM_001173109.1, positions 1-98) | 3 |
| | *Meriones unguiculatus* (Gerbil) | CAGGACCTTGGGTCCACAACAGCATTGCTAAAGCA GCAGATATCACACAGACCCACGGAACCCTTGTCCT TCCACA (GenBank Accession No. XM_021659724.1, positions 1-76) | 4 |
| Carboxyl- esterase 1(Ces1) | *Homo sapiens* (Human) | AGCGCAGGGCGGTAACTCTGGGCGGGGCTGGGCTC CAGGGCTGGACAGCACAGTCCCTCTGAACTGCACA GAGACCTCGCAGGCCCCGGAGAACTGTCGCCCTTCC ACG (GenBank Accession No. NG_012057.1, positions 5001-5108) | 5 |
| | *Macaca mulatto* (Rhesus monkey) | GGCTTTACTGCTATCTCCCAATTAGAGGATTAGGC AATTGGCAGCTCAGGGTGGTAACTCAGGGCCTGG (GenBank Accession No. XM_015126191.2, positions 1-69) | 6 |

[†]RNA Element D of the carboxylesterase 5' UTR sequences are shown in bold underline in the above Table 1.

In some embodiments, the carboxylesterase gene is a carboxylesterase 1D (Ces1d) gene. The Ces1d gene may be a murine Ces1d gene. In accordance with such embodiments, the first nucleic acid sequence comprises at least a portion of the nucleic acid sequence of SEQ ID NO:1. Additional suitable Ces1d gene sequences are shown in Table 1 supra.

In other embodiments, the carboxylase gene is a carboxylesterase 1 (CES1) gene. The CES1 gene may be a human CES1 gene. In accordance with such embodiments, the first nucleic acid sequence comprises at least a portion of the nucleic acid sequence of SEQ ID NO:5. Additional suitable CES1 gene sequences are shown in Table 1 supra.

The Examples below demonstrate the ability of modRNA constructs comprising RNA Element D of the 5' UTR of a mammalian carboxylesterase gene to enhance the translation efficiency of a protein of interest as compared to modRNA constructs comprising an artificial control 5' UTR sequence. In some embodiments, the RNA Element D corresponds to positions 54-72 of SEQ ID NO:1. Thus, in certain embodiments, the first nucleic acid sequence comprises SEQ ID NO:10 (i.e., RNA Element D of the 5' UTR of Mouse Ces1d). In select embodiments, the first nucleic acid sequence comprises SEQ ID NO:14, SEQ ID NO:19, or SEQ ID NO:24.

In other embodiments, the carboxylesterase gene is human CES1 and the first nucleic acid sequence comprises nucleotides 81-93 of SEQ ID NO:5 (i.e., RNA Element D of the 5' UTR of Human CES1). Thus, in certain embodiments, the RNA Element D corresponds to SEQ ID NO:29 (i.e., RNA Element D of the 5' UTR of Human Ces1d).

According to some embodiments, the second nucleic acid sequence encodes a protein of interest. Suitable proteins of interest, which are encoded by the second nucleic acid sequence include, for example and without limitation, a therapeutic protein or a reporter protein.

When the second nucleic acid sequence encodes a therapeutic protein, the therapeutic protein may be, according to one embodiment, a cell cycle inducer. Suitable cell cycle inducers include, without limitation, Lin28, Pyruvate Kinase Muscle Isozyme M2 (Pkm2), β-catenin, caERBB2, Yes Associated Protein 1 (YAP), Cyclin D1, and c-Myc.

Lin28 is a known suppressor of Let7 that tightly controls cell cycle regulators (D'Uva et al., "ERBB2 Triggers Mammalian Heart Regeneration by Promoting Cardiomyocyte Dedifferentiation and Proliferation," *Nat. Cell Biol.* 17(5): 627-638 (2015); Engel et al., "p38 MAP Kinase Inhibition Enables Proliferation of Adult Mammalian Cardiomyocytes," *Genes Dev.* 19(10):1175-1187 (2005); Lee et al., "Cell Cycle Re-Entry and Mitochondrial Defects in Myc-Mediated Hypertrophic Cardiomyopathy and Heart Failure," *PloS One* 4(9):e7172 (2009); Liao et al., "Cardiac-Specific Overexpression of Cyclin-Dependent Kinase 2 Increases Smaller Mononuclear Cardiomyocytes," *Circ. Res.* 88(4):443-450 (2001); Ozhan & Weidinger, "Wnt/β-Catenin Signaling in Heart Regeneration," *Cell Regen.* 4(1):3 (2015), which are hereby incorporated by reference in their entirety). Treatment of cardiomyocytes post-myocardial infarction using modRNA constructs encoding Lin28 has been shown to induce cardiomyocyte proliferation, reduce apoptosis, and increase capillary density (see, e.g., U.S. Patent Application Publication No. 2019/0203226 to Zangi et al., which is hereby incorporated by reference in its entirety). In some embodiments, the cell cycle inducer is Lin28.

Pyruvate Kinase Muscle Isozyme M2 (Pkm2) is a pro-proliferative factor, highly expressed in regenerative fetal and early neonatal cardiomyocytes, but not in adult cardiomyocytes (see, e.g., U.S. Patent Application Publication No. 2019/0203226 to Zangi et al., which is hereby incorporated by reference in its entirety). In the cytoplasm, Pkm2 shifts the metabolic fate from glycolysis to pentose phosphate pathway ("PPP") by reducing the conversion of phosphoenolpyruvate to pyruvate (Dong et al., "PKM2 and Cancer: The Function of PKM2 Beyond Glycolysis," *Oncol. Lett.* 11(3):1980-1986 (2016) and Riganti et al., "The Pentose Phosphate Pathway: An Antioxidant Defense and a Crossroad in Tumor Cell Fate," *Free Rad. Biol. Med.* 53(3):421-

436 (2012), which are hereby incorporated by reference in their entirety), which leads to the accumulation of galactose, a glycolysis intermediate, and activation of PPP via Glucose-6-phosphate dehydrogenase (G6pd) (Kumar et al., "Moderate DNA Damage Promotes Metabolic Flux into PPP via PKM2 Y-105 Phosphorylation: A feature that Favours Cancer Cells," *Mol. Biol. Rep.* 42(8):1317-1321 (2015); Salani et al., "IGF1 Regulates PKM2 Function Through Akt Phosphorylation," Cell Cycle 14(10):1559-1567 (2015); and Wong et al., "PKM2, a Central Point of Regulation in Cancer Metabolism," *Int. J. Cell Biol.* 2013: 242513 (2013), which are hereby incorporated by reference in their entirety). The PPP pathway activation leads to the synthesis of nucleotides, amino acids, and lipids and the production of reduced NADPH, increase nitric oxide synthase and DNA repair (Luo & Semenza, "Pyruvate Kinase M2 Regulates Glucose Metabolism by Functioning as a Coactivator for Hypoxia-Inducible Factor 1 in Cancer Cells," *Oncotarget* 2(7):551-556 (2011); Mazurek, "Pyruvate Kinase Type M2: A Key Regulator of the Metabolic Budget System in Tumor Cells," *Int. J. Biochem. Cell Biol.* 43(7):969-980 (2011); Vander Heiden et al., "Understanding the Warburg Effect: The Metabolic Requirements of Cell Proliferation," *Science* 324(5930):1029-1033 (2009); Luo et al., "Induction of Apoptosis in Human Leukemic Cell Lines by Diallyl Disulfide via Modulation of EGFR/ERK/PKM2 Signaling Pathways," *Asian Pac. J. Cancer Prev.* 16(8): 3509-3515 (2015); Zhang et al., "Nuclear Translocation of PKM2 Modulates Astrocyte Proliferation via p27 and β-Catenin Pathway After Spinal Cord Injury," *Cell Cycle* 14(16):2609-2618 (2015); and David et al., "HnRNP Proteins Controlled by c-Myc Deregulate Pyruvate Kinase mRNA Splicing in Cancer," *Nature* 463(7279):364-368 (2010), which are hereby incorporated by reference in their entirety). In the nucleus, Pkm2 directly interacts with the transcription factors μ-catenin and Hif1α. This interaction promotes the expression of genes such as in Ccdn1, c-Myc and Vegfa, and Bc12 (Luo et al., "Pyruvate Kinase M2 is a PHD3-Stimulated Coactivator for Hypoxia-Inducible Factor 1," *Cell* 145(5):732-744 (2011) and Azoitei et al., "PKM2 Promotes Tumor Angiogenesis by Regulating HIF-1alpha Through NF-kappaB Activation," *Mol. Cancer* 15:3 (2016), which are hereby incorporated by reference in their entirety). Restoration of Pkm2 levels using modRNA into adult cardiomyocytes post-myocardial infarction has been shown to significantly and exclusively induce cardiomyocyte proliferation; associate with improved cardiac function, reduced scar size, and increased heart to body weight ratio; reduce cardiomyocyte size; reduce apoptosis; and increase capillary density (see, e.g., U.S. Patent Application Publication No. 2019/0203226 to Zangi et al., which is hereby incorporated by reference in its entirety). In some embodiments, the cell cycle inducer is Pyruvate Kinase Muscle Isozyme M2 (Pkm2).

β-catenin is a subunit of the cadherin protein complex and acts as an intracellular signal transducer in the Wnt signaling pathway. In cardiac muscle, β-catenin localizes to adherens junctions in intercalated disc structures, which are critical for electrical and mechanical coupling between adjacent cardiomyocytes. Loss of β-catenin during early heart formation results in multiple heart defects and lethality demonstrating its crucial function for embryonic heart development (Lickert et al., "Formation of Multiple Hearts in Mice Following Deletion of Beta-Catenin in the Embryonic Endoderm," *Dev. Cell* 3:171-181 (2002), which is hereby incorporated by reference in its entirety). In adults, β-catenin signaling plays an important role in normal and stress-induced cardiac hypertrophic remodeling (Chen et al., "The Beta-Catenin/T-cell Factor/Lymphocyte Enhancer Factor Signaling Pathway is Required for Normal and Stress-Induced Cardiac Hypertrophy," *Mol. Cell Biol.* 26:4462-4473 (2006), which is hereby incorporated by reference in its entirety). Wnt/β-catenin signaling may function in a stage-specific biphasic manner, either promoting or inhibiting cardiogenesis (Stubenvoll et al., "Attenuation of Wnt/β-catenin Activity Reverses Enhanced Generation of Cardiomyocytes and Cardiac Defects Caused by the loss of Emerin," *Human Mol. Gen.* 24(3):802-813 (2015) and Grigoryan et al., "Deciphering the Function of Canonical Wnt Signals in Development and Disease: Conditional Loss- and Gain-of-Function Mutations of Beta-Catenin in Mice," *Genes Dev.* 22:2308-2341 (2008), which is hereby incorporated by reference in its entirety).

ERBB2 (erb-b2 receptor tyrosine kinase 2) forms a heterodimer with other epidermal growth factor receptor tyrosine kinase family members. ERBB2 is required for cardiomyocyte proliferation at embryonic/neonatal stages (D'Uva et al., "ERBB2 Triggers Mammalian Heart Regeneration by Promoting Cardiomyocyte Dedifferentiation and Proliferation," *Nat. Cell Biol.* 17(5):627-638 (2015), which is hereby incorporated by reference in its entirety). Transient induction of a constitutively active ERBB2 (caERBB2) for 10-20 days after ischemic injury, either in juvenile or adult hearts, has been shown to trigger a series of events starting with cardiomyocyte dedifferentiation, proliferation, neovascularization and, after ERBB2-signaling termination, proceeding to cardiomyocyte re-differentiation that together lead to anatomical and functional heart regeneration (D'Uva et al., "ERBB2 Triggers Mammalian Heart Regeneration by Promoting Cardiomyocyte Dedifferentiation and Proliferation," *Nat. Cell Biol.* 17(5):627-638 (2015) and D'Uva & Tzahor, "The Key Roles of ERBB2 in Cardiac Regeneration," *Cell Cylce* 14(15):2383-2384 (2015), which are hereby incorporated by reference in their entirety).

Yes Associated Protein 1 (YAP) is a transcriptional coactivator, whose activation in adult cardiomyocytes has been shown to increases cardiomyocyte proliferation and improve cardiac function after myocardial infarction in mice (Lin et al., "Cardiac-Specific YAP Activation Improves Cardiac Function and Survival in an Experimental Murine MI Model," *Circ. Res.* 115(3):354-363 (2014), which is hereby incorporated by reference in its entirety).

Cyclin D1 is a regulatory subunit of CDK4 and CDK6, whose activity is required for cell cycle G1/S transition. Overexpression of cyclin D1 results in an increase in CDK4 levels in the adult myocardium, as well as modest increases in proliferating cell nuclear antigen and CDK2 levels (Soonpaa et al., "Cyclin D1 Overexpression Promotes Cardiomyocyte DNA Synthesis and Multinucleation in Transgenic Mice," *J. Clin. Invest.* 99(11):2644-2654 (1997), which is hereby incorporated by reference in its entirety). Expression of cyclin D1 has been shown to promote cell cycle reentry of cardiomyocytes in adult hearts (Lee et al., "Critical Role of Cyclin D1 Nuclear Import in Cardiomyocyte Proliferation," *Circ. Res.* 92(1):e12-19 (2009), which is hereby incorporated by reference in its entirety).

cMYC is highly expressed in fetal, proliferating cardiac myocytes. Although expressed at low levels in the adult heart under normal physiological conditions, c-Myc expression is rapidly upregulated in response to hypertrophic stimuli (Lee et al., "Cell Cycle Re-Entry and Mitochondrial Defects in Myc-Mediated Hypertrophic Cardiomyopathy and Heart Failure," *PLoS One* 4(9):e7172 (2009), which is hereby incorporated by reference in its entirety). Activation of cMyc in adult myocardium has been shown to provoke cell cycle reentry in post-mitotic mycotyes (Xiao et al., "Inducible Activation of c-Myc in Adult Myocardium In Vivo Provokes Cardiac Myocyte Hypertrophy and Reactivation of DNA Synthesis," *Circ. Res.* 89(12):1122-1129 (2001), which is hereby incorporated by reference in its entirety).

Exemplary nucleotide sequences encoding suitable cell cycle inducer are shown in Table 2 below.

TABLE 2

Suitable Cell Cycle Inducer Sequences

| Cell Cycle Inducer | Nucleotide Sequence | SEQ ID NO: |
|---|---|---|
| Lin28 (Mouse) | ATGGGCTCGGTGTCCAACCAGCAGTTTGCAGGTGGCTGCGCCAAGGCAGCGGAGAAGGC<br>GCCAGAGGAGGCGCCGCCTGACGCGGCCCGAGCGGCAGACGAGCCGCAGCTGCTGCACG<br>GGGCCGGCATCTGTAAGTGGTTCAACGTGCGCATGGGGTTCGGCTTCCTGTCTATGACC<br>GCCCGCGCTGGGGTCGCGCTCGACCCCCCGGTGGACGTCTTTGTGCACCAGAGCAAGCT<br>GCACATGGAAGGGTTCCGAAGCCTCAAGGAGGGTGAGGCGGTGGAGTTCACCTTTAAGA<br>AGTCTGCCAAGGGTCTGGAATCCATCCGTGTCACTGGCCCTGGTGGTGTGTTCTGTATT<br>GGGAGTGAGCGGCGGCCAAAAGGGAAGAACATGCAGAAGCGAAGATCCAAAGGAGACAG<br>GTGCTACAACTGCGGTGGGCTAGACCATCATGCCAAGGAATGCAAGCTGCCACCCCAGC<br>CCAAGAAGTGCCACTTTTGCCAAAGCATCAACCATATGGTGGCCTCGTGTCCACTGAAG<br>GCCCAGCAGGGCCCCAGTTCTCAGGGAAAGCCTGCCTACTTCCGGGAGGAAGAGGAAGA<br>GATCCACAGCCCTGCCCTGCTCCCAGAAGCCCAGAATTGA | 36 |
| Pkm2 (Mouse) | ATGCCGAAGCCACACAGTGAAGCAGGGACTGCCTTCATTCAGACCCAGCAGCTCCATGC<br>AGCCATGGCTGACACCTTCCTGGAACACATGTGCCGCCTGGACATTGACTCTGCCCCCA<br>TCACGGCCCGCAACACTGGCATCATTTGTACCATTGGGCCTGCTTCCCGATCTGTGGAG<br>ATGCTGAAGGAGATGATTAAGTCTGGAATGAATGTGGCTCGGCTGAATTTCTCTCATGG<br>AACCCATGAGTACCATGCAGAGACCATCAAGAATGTCCGTGAAGCCACAGAAAGCTTTG<br>CATCTGATCCCATTCTCTACCGTCCTGTTGCGGTGGCTCTGGATACAAAGGGACCTGAG<br>ATCCGGACTGGACTCATCAAGGGCAGCGGCACCGCTGAGGTGGAGCTGAAGAAGGGAGC<br>CACTCTGAAGATCACCCTGGACAACGCTTACATGGAGAAGTGTGACGAGAACATCCTGT<br>GGCTGGACTACAAGAACATCTGCAAGGTGGTGGAGGTGGGCAGCAAGATCTACGTGGAC<br>GATGGGCTCATCTCACTGCAGGTGAAGGAGAAAGGCGCTGACTTCCTGGTGACGGAGGT<br>GGAGAATGGTGGCTCCTTGGGCAGCAAGAAGGGCGTGAACCTGCCGGGCGCTGCTGTGG<br>ATCTCCCCGCTGTGTCGGAAAAGGACATCCAGGACCTGAAGTTTGGGGTGGAGCAGGAT<br>GTGGACATGGTGTTTGCATCTTTCATCCGCAAGGCAGCCGACGTGCATGAAGTCAGGAA<br>GGTGCTGGGAGAGAAGGGCAAGAACATCAAGATCATCAGCAAAATCGAGAACCATGAAG<br>GCGTCCGCAGGTTTGATGAGATCTTGGAGGCCAGTGATGGGATCATGGTGGCTCGTGGT<br>GACCTGGGCATTGAGATTCCTGCAGAGAAGGTCTTCCTGGCTCAGAAGATGATGATCGG<br>GCGATGCAACCGAGCTGGGAAGCCTGTCATCTGTGCCACACAGATGCTGGAGAGCATGA<br>TCAAGAAGCCACGCCCCACCCGTGCTGAAGGCAGTGATGTGGCCAATGCAGTCCTGGAT<br>GGAGCAGACTGCATCATGCTGTCTGGAGAAACAGCCAAGGGGGACTACCCTCTGGAGGC<br>TGTTCGCATGCAGCACCTGATTGCCCGAGAGGCAGAGGCTGCCATCTACCACTTGCAGC<br>TATTCGAGGAACTCCGCCGCCTGGCGCCCATTACCAGCGACCCCACAGAAGCTGCCGCC<br>GTGGGTGCCGTGGAGGCCTCCTTCAAGTGCTGCAGTGGGGCCATTATCGTGCTCACCAA<br>GTCTGGCAGGAGTGCTCACCAAGTGGCCAGGTACCGCCCTCGGGCTCCTATCATTGCCG<br>TGACTCGAAATCCCCAGACTGCTCGCCAGGCCCATCTGTACCGTGGCATCTTCCCTGTG<br>CTGTGTAAGGATGCCGTGCTGAATGCCTGGGCTGAGGATGTCGACCTTCGTGTAAACTT<br>GGCCATGGATGTTGGCAAGGCCCGAGGCTTCTTCAAGAAGGGAGATGTGGTCATTGTGC<br>TGACCGGGTGGCGCCCTGGCTCGGATTCACCAACACCATGCGTGTAGTGCCTGTACCT<br>TGA | 37 |
| β-catenin (Mouse) | ATGGCTACTCAAGCTGACCTGATGGAGTTGGACATGGCCATGGAGCCGGACAGAAAAGC<br>TGCTGTCAGCCACTGGCAGCAGCAGTCTTACTTGGATTCTGGAATCCATTCTGGTGCCA<br>CCACCACAGCTCCTTCCCTGAGTGGCAAGGGCAACCCTGAGGAAGAAGATGTTGACACC<br>TCCCAAGTCCTTTATGAATGGGAGCAAGGCTTTTCCCAGTCCTTCACGCAAGAGCAAGT<br>AGCTGATATTGACGGGCAGTATGCAATGACTAGGGCTCAGAGGGTCCGAGCTGCCATGT<br>TCCCTGAGACGCTAGATGAGGGCATGCAGATCCCATCCACGCAGTTTGACGCTGCTCAT<br>CCCACTAATGTCCAGCGCTTGGCTGAACCATCACAGATGTTGAAACATGCAGTTGTCAA<br>TTTGATTAACTATCAGGATGACGCGGAACTTGCCACACGTGCAATTCCTGAGCTGACAA<br>AACTGCTAAACGATGAGGACCAGGTGGTAGTTAATAAAGCTGCTGTTATGGTCCATCAG<br>CTTTCCAAAAAGGAAGCTTCCAGACATGCCATCATGCGCTCCCCTCAGATGGTGTCTGC<br>CATTGTACGCACCATGCAGAATACAAATGATGTAGAGACAGCTCGTTGTACTGCTGGGA<br>CTCTGCACAACCTTTCTCACCACCGCGAGGGCTTGCTGGCCATCTTTAAGTCTGGTGGC<br>ATCCCAGCGCTGGTGAAAATGCTTGGGTCACCAGTGGATTCTGTACTGTTCTACGCCAT<br>CACGACACTGCATAATCTCCTGCTCCATCAGGAAGGAGCTAAAATGGCAGTGCGCCTAG<br>CTGGTGGACTGCAGAAAATGGTTGCTTTGCTCAACAAAACAAACGTGAAATTCTTGGCT<br>ATTACAACAGACTGCCTTCAGATCTTAGCTTATGGCAATCAAGAGAGCAAGCTCATCAT<br>TCTGGCCAGTGGTGGACCCCAAGCCTTAGTAAACATAATGAGGACCTACACTTATGAGA<br>AGCTTCTGTGGACCACAAGCAGAGTGCTGAAGGTGCTGTCTGTCTGCTCTAGCAACAAG<br>CCGGCCATTGTAGAAGCTGGTGGGATGCAGGCACTGGGGCTTCATCTGACAGACCCAAG<br>TCAGCGACTTGTTCAAAACTGTCTTTGGACTCTCAGAAACCTTTCAGATGCAGCGACTA<br>AGCAGGAAGGGATGGAAGGCCTCCTTGGGACTCTAGTGCAGCTTCTGGGTTCCGATGAT<br>ATAAATGTGGTCACCTGTGCAGCTGGAATTCTCTCTAACCTCACTTGCAATAATTACAA<br>AAACAAGATGATGGTGTGCCAAGTGGGTGGCATAGAGGCTCTTGTACGCACCGTCCTTC<br>GTGCTGGTGACAGGGAAGACATCACTGAGCCTGCCATCTGTGCTCTTCGTCATCTGACC<br>AGCCGGCATCAGGAAGCCGAGATGGCCCAGAATGCCGTTCGCCTTCATTATGGACTGCC<br>TGTTGTGGTTAAACTCCTGCACCCACCATCCCACTGGCCTCTGATAAAGGCAACTGTTG | 38 |

TABLE 2-continued

Suitable Cell Cycle Inducer Sequences

| Cell Cycle Inducer | Nucleotide Sequence | SEQ ID NO: |
|---|---|---|
| | GATTGATTCGAAACCTTGCCCTTTGCCCAGCAAATCATGCGCCTTTGCGGGAACAGGGT<br>GCTATTCCACGACTAGTTCAGCTGCTTGTACGAGCACATCAGGACACCCAACGGCGCAC<br>CTCCATGGGTGGAACGCAGCAGCAGTTTGTGGAGGGCGTGCGCATGGAGGAGATAGTAG<br>AAGGGTGTACTGGAGCTCTCCACATCCTTGCTCGGGACGTTCACAACCGGATTGTAATC<br>CGAGGACTCAATACCATTCCATTGTTTGTGCAGTTGCTTTATTCTCCCATTGAAAATAT<br>CCAAAGAGTAGCTGCAGGGGTCCTCTGTGAACTTGCTCAGGACAAGGAGGCTGCAGAGG<br>CCATTGAAGCTGAGGGAGCCACAGCTCCCCTGACAGAGTTACTCCACTCCAGGAATGAA<br>GGCGTGGCAACATACGCAGCTGCTGTCCTATTCCGAATGTCTGAGGACAAGCCACAGGA<br>TTACAAGAAGCGGCTTTCAGTCGAGCTGACCAGTTCCCTCTTCAGGACAGAGCCAATGG<br>CTTGGAATGAGACTGCAGATCTTGGACTGGACATTGGTGCCCAGGGAGAAGCCCTTGGA<br>TATCGCCAGGATGATCCCAGCTACCGTTCTTTTCACTCTGGTGGATACGGCCAGGATGC<br>CTTGGGGATGGACCCTATGATGGAGCATGAGATGGGTGGCCACCACCCTGGTGCTGACT<br>ATCCAGTTGATGGGCTGCCTGATCTGGGACACGCCCAGGACCTCATGGATGGGCTGCCC<br>CCAGGTGATAGCAATCAGCTGGCCTGGTTTGATACTGACCTGTAA | |
| caERBB2<br>(Mouse and<br>human) | ATGAAGCTGCGGCTGCCCGCCTCTCCTGAGACACACCTGGACATGCTGCGGCACCTGTA<br>CCAGGGCTGTCAGGTGGTGCAGGGCAACCTGGAACTGACCTACCTGCCCACCAACGCCA<br>GCCTGAGCTTTCTGCAGGACATCCAGGAAGTGCAGGGCTACGTCCTGATCGCCCACAAC<br>CAGGTCCGACAGGTGCCCCTGCAGAGACTGAGAATCGTGCGGGGCACCCAGCTGTTCGA<br>GGACAATTATGCCCTGGCCGTGCTGGACAACGGCGACCCCCTGAACAATACCACCCCTG<br>TGACAGGCGCCAGCCCTGGCGGACTGAGAGAACTGCAGCTGCGGAGCCTGACCGAGATC<br>CTGAAGGGCGGCGTGCTGATCCAGAGAAACCCCCAGCTGTGCTACCAGGACACCATCCT<br>GTGGAAGGACATCTTCCACAAGAACAACCAGCTGGCCCTGACCCTGATCGACACCAACA<br>GAAGCAGAGCCTGCCACCCCTGCAGCCCCATGTGCAAGGGCTCTAGATGTTGGGGCGAG<br>AGCAGCGAGGACTGCCAGTCCCTGACCAGAACAGTGTGTGCCGGCGGATGCGCCAGATG<br>CAAGGGCCCTCTGCCTACCGATTGCTGCCACGAGCAGTGTGCCGCTGGCTGTACAGGCC<br>CCAAGCACAGCGATTGCCTGGCCTGCCTGCACTTTAACCACAGCGGCATCTGCGAGCTG<br>CACTGCCCTGCCCTGGTCACCTACAACACCGACACCTTCGAGAGCATGCCCAACCCCGA<br>GGGCAGATACACCTTCGGCGCCAGCTGTGTGACCGCCTGCCCCTACAACTACCTGAGCA<br>CCGATGTGGGCAGCTGCACCCTCGTGTGCCCCCTGCACAATCAGGAAGTGACCGCCGAG<br>GACGGCACCCAGAGATGCGAGAAGTGCAGCAAGCCCTGCGCCAGAGTGTGCTACGGCCT<br>GGGCATGGAACACCTGAGAGAAGTGCGGGCCGTGACCAGCGCCAATATCCAGGAATTCG<br>CCGGCTGCAAGAAGATCTTTGGCTCCCTGGCCTTTCTGCCCGAGAGCTTCGATGGCGAC<br>CCTGCCTCTAATACCGCCCCTCTGCAGCCAGAGCAGCTCCAGGTGTTCGAGACACTGGA<br>AGAGATCACCGGCTACCTGTACATCAGCGCCTGGCCCGACAGCCTGCCCGATCTGAGCG<br>TGTTCCAGAATCTGCAGGTCATCAGAGGCCGGATCCTGCACAACGGCGCCTACAGCCTG<br>ACACTGCAGGGGCTGGGAATCAGCTGGCTGGGCCTGAGATCTCTGAGAGAGCTGGGCAG<br>CGGCCTGGCTCTGATCCACCACAACACCCACCTGTGCTTCGTGCACACCGTGCCCTGGG<br>ACCAGCTGTTTAGAAACCCTCACCAGGCACTGCTGCACACCGCCAACAGACCCGAGGAT<br>GAGTGTGTGGGCGAAGGCCTGGCTTGCCATCAGCTGTGCGCTAGAGGCCACTGTTGGGG<br>CCCTGGACCTACCCAGTGCGTGAACTGCTCCCAGTTCCTGCGGGGCCAGGAATGCGTGG<br>AAGAGTGCAGAGTGCTGCAGGGACTGCCCCGCGAGTACGTGAACGCCAGACACTGCCTG<br>CCTTGCCACCCTGAGTGCCAGCCTCAGAATGGCAGCGTGACCTGCTTCGGCCCTGAGGC<br>CGATCAGTGTGTGGCCTGCGCCCACTACAAGGACCCCCCATTCTGCGTGGCCAGATGCC<br>CTAGCGGCGTGAAGCCCGACCTGAGCTACATGCCCATCTGGAAGTTCCCCGACGAGGAA<br>GGCGCCTGCCAGCCTTGTCCCATCAACTGCACCCACAGCTGCGTGGACCTGGACGACAA<br>GGGCTGTCCTGCCGAGCAGAGAGCCAGCCCCTGACCTCTATCATCTCCGCCGTGGAAG<br>GCATCCTGCTGGTGGTGGTGCTGGGCGTGGTGTTCGGCATCCTGATCAAGCGGCGGCAG<br>CAGAAGATCCGGAAGTACACCATGCGGCGGCTGCTGCAGGAAACCGAGCTGGTCGAGCC<br>TCTGACACCAAGCGGCGCCATGCCTAACCAGGCCCAGATGCGGATCCTGAAAGAGACAG<br>AGCTGCGGAAAGTGAAGGTGCTGGGATCCGGCGCCTTCGGCACAGTGTACAAGGGAATC<br>TGGATCCCCGACGGCGAGAACGTGAAGATCCCCGTGGCCATCAAGGTGCTGAGAGAGAA<br>CACCAGCCCCAAGGCCAACAAAGAGATCCTGGACGAGGCCTACGTGATGGCCGGCGTGG<br>GCAGCCCTTATGTGTCCAGACTGCTGGGCATCTGCCTGACCAGCACCGTGCAGCTGGTC<br>ACTCAGCTGATGCCTTACGGCTGCCTGCTGGACCACGTGCGCGAGAATAGAGGCAGACT<br>GGGCAGCCAGGACCTGCTGAACTGGTGCATGCAGATCGCCAAGGGCATGAGCTACCTCG<br>AGGACGTGCGGCTGGTGCACAGAGATCTGGCCGCCAGAAACGTGCTCGTGAAGTCCCCC<br>AACCACGTGAAAATCACCGACTTCGGACTGGCCCGGCTGCTGGACATCGACGAGACAGA<br>GTATCACGCCGACGGCGGCAAGGTGCCCATCAAGTGGATGGCCCTGGAATCCATCCTGC<br>GGCGGAGGTTCACCCACCAGAGCGACGTGTGGTCTTACGGCGTGACCGTGTGGGAGCTG<br>ATGACATTCGGAGCCAAGCCCTACGACGGCATCCCCGCCAGAGAGATCCCCGATCTGCT<br>GGAAAAGGGCGAGAGACTGCCCCAGCCCCCCATCTGCACCATCGACGTGTACATGATTA<br>TGGTCAAGTGCTGGATGATCGACAGCGAGTGCCGGCCCAGATTCCGCGAGCTGGTGTCC<br>GAGTTCTCCAGAATGGCCCGGGACCCCCAGAGATTCGTGGTCATCCAGAACGAGGACCT<br>GGGCCCTGCCTCCCCCCTGGACTCCACCTTTTACCGGTCCCTGCTGGAAGATGACGACA<br>TGGGCGACCTGGTGGACGCCGAGGAATACCTGGTGCCCCAGCAGGGCTTCTTCTGCCCT<br>GATCCTGCTCCTGGCGCTGGCGGCATGGTGCATCACAGACACAGAAGCTCCAGCACCAG<br>AAGCGGAGGCGGCGATCTGACCCTGGGACTGGAACCTTCTGAGGAAGAGGCCCCTAGAA<br>GCCCCCTGGCCCCTAGTGAAGGGGCAGGATCTGATGTGTTCGACGGGGACCTGGGAATG<br>GGCGCTGCCAAAGGACTGCAGAGTCTGCCCACCCACGACCCCAGCCCACTGCAGAGGTA<br>CAGCGAGGATCCTACCGTGCCTCTGCCCAGCGAGACAGATGGCTACGTGGCCCCTCTGA<br>CCTGTAGCCCCCAGCCCGAGTATGTGAACCAGCCCGATGTGCGGCCTCAGCCTCCTAGC<br>CCTAGAGAAGGACCTCTGCCTGCCGCTAGACCTGCCGGCGCTACCCTGGAAAGACCCAA<br>GACACTGAGCCCCGGCAAGAACGGCGTGGTCAAGGACGTGTTCGCCTTTGGCGGAGCCG<br>TGGAAAACCCCGAGTACCTGACACCTCAGGGCGGAGCAGCACCTCAGCCACACCCTCCA | 39 |

TABLE 2-continued

| | Suitable Cell Cycle Inducer Sequences | |
|---|---|---|
| Cell Cycle Inducer | Nucleotide Sequence | SEQ ID NO: |
| | CCAGCCTTCAGCCCCGCCTTCGACAACCTGTACTACTGGGATCAGGACCCTCCCGAGAG AGGCGCCCCACCTAGCACCTTTAAGGGCACCCCTACCGCCGAGAATCCTGAGTACCTGG GGCTGGACGTGCCCGTCTAA | |
| YAP (Mouse) | ATGGACTACAAAGACGATGACGACAAGCTTGCGGCCGCGAATTCAAGCTTAGCCACCAT GGACTACAAAGACGATGACGATAAAGCAAGGCTCGAATCGGTACCTAAGGATCCCGGGC AGCAGCCGCCGCCTCAACCGGCCCCCCAGGGCCAAGGGCAGCCGCCTTCGCAGCCCCCG CAGGGGCAGGGCCCGCCGTCCGGGACCCGGGCAACCGGCACCCGCGGCGACCCAGGCGGC GCCGCAGGCACCCCCGCCGGGCATCAGATCGTGCACGTCCGCGGGGACTCGGAGACCG ACCTGGAGGCGCTCTTCAACGCCGTCATGAACCCCAAGACGGCCAACGTGCCCCAGACC GTGCCCATGAGGCTCCGGAAGCTGCCCGACTCCTTCTTCAAGCCGCCGGAGCCCAAATC CCACTCCCGACAGGCCAGTACTGATGCAGGCACTGCAGGAGCCCTGACTCCACAGCATG TTCGAGCTCATGCCTCTCCAGCTTCTCTGCAGTTGGGAGCTGTTTCTCCTGGGACACTG ACCCCCACTGGAGTAGTCTCTGGCCCAGCAGCTACACCCACAGCTCAGCATCTTCGACA GTCTTCTTTTGAGATACCTGATGATGTACCTCTGCCAGCAGGTTGGGAGATGGCAAAGA CATCTTCTGGTCAGAGATACTTCTTAAATCACATCGATCAGACAACAACATGGCAGGAC CCCAGGAAGGCCATGCTGTCCCAGATGAACGTCACAGCCCCCACCAGTCCACCAGTGCA GCAGAATATGATGAACTCGGCTTCAGGTCCTCTTCCTGATGGATGGGAACAAGCCATGA CTCAGGATGGAGAAATTTACTATATAAACCATAAGAACAAGACCACCTCTTGGCTAGAC CCAAGGCTTGACCCTCGTTTTGCCATGAACCAGAGAATCAGTCAGATGTGCTCCAGTGAA ACAGCCACCACCCCTGGCTCCCCAGAGCCCACAGGGAGGCGTCATGGGTGGCAGCAACT CCAACCAGCAGCAACAGATGCGACTGCAGCAACTGCAGATGGAGAAGGAGAGGCTGCGG CTGAAACAGCAAGAACTGCTTCGGCAGGAGTTAGCCCTGCGTAGCCAGTTACCAACACT GGAGCAGGATGGTGGGACTCAAAATCCAGTGTCTTCTCCCGGGATGTCTCAGGAATTGA GAACAATGACGACCAATAGCTCAGATCCTTTCCTTAACAGTGGCACCTATCACTCTCGA GATGAGAGTACAGACAGTGGACTAAGCATGAGCAGCTACAGTGTCCCTCGAACCCCCAGA TGACTTCCTGAACAGTGTGGATGAGATGGATACAGGTGATACTATCAACCAAAGCACCC TGCCCTCACAGCAGAACCGTTTCCCAGACTACCTTGAAGCCATTCCTGGGACAAATGTG GACCTTGGAACACTGGAAGGAGATGGAATGAACATAGAAGGAGAGGAGCTGATGCCAAG TCTGCAGGAAGCTTTGAGTTCTGACATCCTTAATGACATGGAGTCTGTTTTGGCTGCCA CCAAGCTAGATAAAGAAAGCTTTCTTACATGGTTATAG | 40 |
| Cyclin D1 (Mouse) | ATGGAACACCAGCTCCTGTGCTGCGAAGTGGAGACCATCCGCCGCGCGTACCCTGACAC CAATCTCCTCAACGACCGGGTGCTGCGAGCCATGCTCAAGACGGAGGAGACCTGTGCGC CCTCCGTATCTTACTTCAAGTGCGTGCAGAAGGAGATTGTGCCATCCATGCGGAAAATC GTGGCCACCTGGATGCTGGAGGTCTGTGAGGAGCAGAAGTGCGAAGAGGAGGTCTTCCC GCTGGCCATGAACTACCTGGACCGCTTCCTGTCCCTGGAGCCCTTGAAGAAGAGCCGCC TGCAGCTGCTGGGGGCCACCTGCATGTTCGTGGCCTCTAAGATGAAGGAGACCATTCCC TTGACTGCCGAGAAGTTGTGCATCTACACTGACAACTCTATCCGGCCCGAGGAGCTGCT GCAAATGGAACTGCTTCTGGTGAACAAGCTCAAGTGGAACCTGGCCGCCATGACTCCCC ACGATTTCATCGAACACTTCCTCTCCAAAATGCCAGAGGCGGATGAGAACAAGCAGACC ATCCGCAAGCATGCACAGACCTTTGTGGCCCTCTGTGCCACAGATGTGAAGTTCATTTC CAACCCACCCTCCATGGTAGCTGCTGGGAGCGTGGTGGCTGCGATGCAAGGCCTGAACC TGGGCAGCCCCAACAACTTCCTCTCCTGCTACCGCACAACGCACTTTCTTTCCAGAGTC ATCAAGTGTGACCCGGACTGCCTCCGTGCCTGCCAGGAACAGATTGAAGCCCTTCTGGA GTCAAGCCTGCGCCAGGCCCAGCAGAACGTCGACCCCAAGGCCACTGAGGAGGAGGGGG AAGTGGAGGAAGAGGCTGGTCTGGCCTGCACGCCCACCGACGTGCGAGATGTGGACATC TGA | 41 |
| C-Myc (Mouse) | ATGCCGCTGAACGTGAGCTTTACCAACCGCAACTATGATCTGGATTATGATAGCGTGCA GCCGTATTTTTATTGCGATGAAGAAGAAAACTTTTATCAGCAGCAGCAGCAGAGCGCGAAC TGCAGCCGCCGGCGCCGAGCGAAGATATTTTGGAAAAAATTTGAACTGCTGCCGACCCCG CCGCTGAGCCCGAGCGCCGCAGCGGCCTGTGCAGCCCGAGCTATGTGGCCGGTGACCCC GTTTAGCCTGCGCGGCGATAACGATGGCGGCGGCGGCAGCTTTAGCACCGCGGATCAGC TGGAAATGGTGACCGAACTGCTGGGCGGCGATATGGTGAACCAGAGCTTTATTTGCGAT CCGGATGATGAAACCTTTATTAAAAACATTATTATTCAGGATTGCATGTGGAGCGGCTT TAGCGCGGCGGCGAAACTGGTGAGCGAAAAACTGGCGAGCTATCAGGCGGCGCGCAAAG ATAGCGGCAGCCCGAACCCGGCGCGCGGCCATAGCGTGTGCAGCACCAGCAGCCTGTAT CTGCAGGATCTGAGCGCGGCGGCGAGCGAATGCATTGATCCGAGCGTGGTGTTTCCGTA TCCGCTGAACGATAGCAGCAGCCCGAAAAGCTGCGCGAGCCAGGATAGCAGCGCGTTTA GCCCGAGCAGCGATAGCCTGCTGAGCAGCACCGAAAGCAGCCCGCAGGGCAGCCCGGAA CCGCTGGTGCTGCATGAAGAAACCCCGCCGACCACCAGCAGCGATAGCGAAGAAGAACA GGAAGATGAAGAAGAAATTGATGTGGTGAGCGTGGAAAAACGCCAGGCGCCGGGCAAAC GCAGCGAAAGCGGCAGCCCGAGCGCGGGCGGCCATAGCAAACCGCCGCATAGCCCGCTG GTGCTGAAACGCTGCCATGTGAGCACCCATCAGCATAACTATGCGGCGCCGCCGAGCAC CCGCAAAGATTATCCGGCGGCGAAACGCGTGAAACTGGATAGCGTGCGCGTGCTGCGCC AGATTAGCAACAACCGCAAATGCACCAGCCCGCGCAGCAGCGATACCGAAGAAAACGTG AAACGCCGCACCCATAACGTGCTGGAACGCCAGCGCCGCAACGAACTGAAACGCAGCTT TTTTGCGCTGCGCGATCAGATTCCGGAACTGGAAAACAACGAAAAAGCGCCGAAAGTGG TGATTCTGAAAAAAGCGACCGCGTATATTCTGAGCGTGCAGGCGGAAGAACAGAAACTG ATTAGCGAAGAAGATCTGCTGCGCAAACGCCGCGAACAGCTGAAACATAAACTGGAACA GCTGCGCAACAGCTGCGCGTAA | 42 |

TABLE 2-continued

Suitable Cell Cycle Inducer Sequences

| Cell Cycle Inducer | Nucleotide Sequence | SEQ ID NO: |
|---|---|---|
| Lin28 (Human) | ATGGGCTCCGTGTCCAACCAGCAGTTTGCAGGTGGCTGCGCCAAGGCGGCAGAAGAGGC GCCCGAGGAGGCGCCGGAGGACGCGGCCCGGGCGGCGGACGAGCCTCAGCTGCTGCACG GTGCGGGCATCTGTAAGTGGTTCAACGTGCGCATGGGGTTCGGCTTCCTGTCCATGACC GCCCGCGCCGGGGTCGCGCTCGACCCCCCAGTGGATGTCTTTGTGCACCAGAGTAAGCT GCACATGGAAGGGTTCCGGAGCTTGAAGGAGGGTGAGGCAGTGGAGTTCACCTTTAAGA AGTCAGCCAAGGGTCTGGAATCCATCCGTGTCACCGGACCTGGTGGAGTATTCTGTATT GGGAGTGAGAGGCGGCCAAAAGGAAAGAGCATGCAGAAGCGCAGATCAAAAGGAGACAG GTGCTACAACTGTGGAGGTCTAGATCATCATGCCAAGGAATGCAAGCTGCCACCCCAGC CCAAGAAGTGCCACTTCTGCCAGAGCATCAGCCATATGGTAGCCTCATGTCCGCTGAAG GCCCAGCAGGGCCCTAGTGCACAGGGAAAGCCAACCTACTTTCGAGAGGAAGAAGAAGA AATCCACAGCCCTACCCTGCTCCCGGAGGCACAGAATTGA | 43 |
| Pkm2 (Human) | ATGCAGTGGAGCTCAGAGAGAGGAGAACGGCTCCTCACGCCTGGGGCCTGCTCTTCAGA AGTCCCCAGCGCCGTTCCTTCCAGATCAGGCGGCTCTCCAGGGCACACCGTATTCAGCT CTGAGCGGTCTTTGCTAGTGAGGCCAAGGAGCCACCCTGAGCCAAAAGGGGAGCATTAT GTCACCGGAAGCCCAACCCCAGAGAACCAAAGGACCTCAGCCAGCCATGTCGAAGCCCCA TAGTGAAGCCGGGACTGCCTTCATTCAGACCCAGCAGCTGCACGCAGCCATGGCTGACA CATTCCTGGAGCACATGTGCCGCCTGGACATTGATTCACCACCCATCACAGCCCGGAAC ACTGGCATCATCTGTACCATTGGCCCAGCTTCCCGATCAGTGGAGACGTTGAAGGAGAT GATTAAGTCTGGAATGAATGTGGCTCGTCTGAACTTGTCTCATGGAACTCATGAGTACC ATGCGGAGACCATCAAGAATGTGCGCACAGCCACGGAAAGCTTTGCTTCTGACCCCATC CTCTACCGGCCCGTTGCTGTGGCTCTAGACACTAAAGGACCTGAGATCCGAACTGGGCT CATCAAGGGCAGCGGCACTGCAGAGGTGGAGCTGAAGAAGGGAGCCACTCTCAAAATCA CGCTGGATAACGCCTACATGGAAAAGTGTGACGAGAACATCCTGTGGCTGGACTACAAG AACATCTGCAAGGTGGTGGAAGTGGGCAGCAAGATCTACGTGGATGATGGGCTTATTTC TCTCCAGGTGAAGCAGAAAGGTGCCGACTTCCTGGTGACGGAGGTGGAAAATGGTGGCT CCTTGGGCAGCAAGAAGGGTGTGAACCTTCCTGGGGCTGCTGTGGACTTGCCTGCTGTG TCGGAGAAGGACATCCAGGATCTGAAGTTTGGGGTCGAGCAGGATGTTGATATGGTGTT TGCGTCATTCATCCGCAAGGCATCTGATGTCCATGAAGTTAGGAAGGTCCTGGGAGAGA AGGGAAAGAACATCAAGATTATCAGCAAAATCGAGAATCATGAGGGGGTTCGGAGGTTT GATGAAATCCTGGAGGCCAGTGATGGGATCATGGTGGCTCGTGGTGATCTAGGCATTGA GATTCCTGCAGAGAAGGTCTTCCTTGCTCAGAAGATGATGATTGGACGGTGCAACCGAG CTGGGAAGCCTGTCATCTGTGCTACTCAGATGCTGGAGAGCATGATCAAGAAGCCCCGC CCCACTCGGGCTGAAGGCAGTGATGTGGCCAATGCAGTCCTGGATGGAGCCGACTGCAT CATGCTGTCTGGAGAAACAGCCAAAGGGGACTATCCTCTGGAGGCGTGTGCGCATGCAGC ACCTGATAGCTCGTGAGGCTGAGGCAGCCATGTTCCACCGCAAGCTGTTTGAAGAACTT GTGCGAGCCTCAAGTCACTCCACAGACCTCATGGAAGCCATGGCCATGGGCAGCGTGGA GGCTTCTTATAAGTGTTTAGCAGCAGCTTTGATAGTTCTGACGGAGTCTGGCAGGTCTG CTCACCAGGTGGCCAGATACCGCCCACGTGCCCCCATCATTGCTGTGACCCGGAATCCC CAGACAGCTCGTCAGGCCCACCTGTACCGTGGCATCTTCCCTGTGCTGTGCAAGGACCC AGTCCAGGAGGCCTGGGCTGAGGACGTGGACCTCCGGGTGAACTTTGCCATGAATGTTG GCAAGGCCCGAGGCTTCTTCAAGAAGGGAGATGTGGTCATTGTGCTGACCGGATGGCGC CCTGGCTCCGGCTTCACCAACACCATGCGTGTTGTTCCTGTGCCGTGA | 44 |
| β-catenin (Human) | ATGGCTACTCAAGCTGATTTGATGGAGTTGGACATGGCCATGGAACCAGACAGAAAAGC GGCTGTTAGTCACTGGCAGCAACAGTCTTACCTGGACTCTGGAATCCATTCTGGTGCCA CTACCACAGCTCCTTCTCTGAGTGGTAAAGGCAATCCTGAGGAAGAGGATGTGGATACC TCCCAAGTCCTGTATGAGTGGGAACAGGGATTTTCTCAGTCCTTCACTCAAGAACAAGT AGCTGATATTGATGGACAGTATGCAATGACTCGAGCTCAGAGGGTACGAGCTGCTATGT TCCCTGAGACATTAGATGAGGGCATGCAGATCCCATCTACACAGTTTGATGCTGCTCAT CCCACTAATGTCCAGCGTTTGGCTGAACCATCACAGATGCTGAAACATGCAGTTGTAAA CTTGATTAACTATCAAGATGATGCAGAACTTGCCACACGTGCAATCCCTGAACTGACAA AACTGCTAAATGACGAGGACCAGGTGGTGGTTAATAAGGCTGCAGTTATGGTCCATCAG CTTTCTAAAAAGGAAGCTTCCAGACACGCTATCATGCGTTCTCCTCAGATGGTGTCTGC TATTGTACGTACCATGCAGAATACAAATGATGTAGAAACAGCTCGTTGTACCGCTGGGA CCTTGCATAACCTTTCCCATCATCGTGAGGGCTTACTGGCCATCTTTAAGTCTGGAGGC ATTCCTGCCCTGGTGAAAATGCTTGGTTCACCAGTGGATTCTGTGTTGTTTTATGCCAT TACAACTCTCCACAACCTTTTATTACATCAAGAAGGAGCTAAAATGGCAGTGCGTTTAG CTGGTGGGCTGCAGAAAATGGTTGCCTTGCTCAACAAACAAATGTTAAATTCTTGGCT ATTACGACAGACTGCCTTCAAATTTTAGCTTATGGCAACCAAGAAAGCAAGCTCATCAT ACTGGCTAGTGGTGGACCCCAAGCTTTAGTAAATATAATGAGGACCTATACTTACGAAA AACTACTGTGGACCACAAGCAGAGTGCTGAAGGTGCTATCTGTCTGCTCTAGTAATAAG CCGGCTATTGTAGAAGCTGGTGGAATGCAAGCTTTAGGACTTCACCTGACAGATCCAAG TCAACGTCTTGTTCAGAACTGTCTTTGGACTCTCAGGAATCTTTCAGATGCTGCAACTA AACAGGAAGGGATGGAAGGTCTCCTTGGGACTCTTGTTCAGCTTCTGGGTTCAGATGAT ATAAATGTGGTCACCTGTGCAGCTGGAATTCTTTCTAACCTCACTTGCAATAATTATAA GAACAAGATGATGGTCTGCCAAGTGGGTGGTATAGAGGCTCTTGTGCGTACTGTCCTTC GGGCTGGTGACAGGGAAGACATCACTGAGCCTGCCATCTGTGCTCTTCGTCATCTGACC AGCCGACACCAAGAAGCAGAGATGGCCCAGAATGCAGTTCGCCTTCACTATGGACTACC AGTTGTGGTTAAGCTCTTACACCCACCATCCCACTGGCCTCTGATAAAGGCTACTGTTG GATTGATTCGAAATCTTGCCCTTTGTCCCGCAAATCATGCACCTTTGCGTGAGCAGGGT GCCATTCCACGACTAGTTCAGTTGCTTGTTCGTGCACATCAGGATACCCAGCGCCGTAC GTCCATGGGTGGACACAGCAGCAATTTGTGGAGGGGGTCCGCATGGAAGAAATAGTTG AAGGTTGTACCGGAGCCCTTCACATCCTAGCTCGGGGATGTTCACAACCGAATTGTTATC | 45 |

TABLE 2-continued

Suitable Cell Cycle Inducer Sequences

| Cell Cycle Inducer | Nucleotide Sequence | SEQ ID NO: |
|---|---|---|
| | AGAGGACTAAATACCATTCCATTGTTTGTGCAGCTGCTTTATTCTCCCATTGAAAACAT CCAAAGAGTAGCTGCAGGGGTCCTCTGTGAACTTGCTCAGGACAAGGAAGCTGCAGAAG CTATTGAAGCTGAGGGAGCCACAGCTCCTCTGACAGAGTTACTTCACTCTAGGAATGAA GGTGTGGCGACATATGCAGCTGCTGTTTTGTTCCGAATGTCTGAGGACAAGCCACAAGA TTACAAGAAACGGCTTTCAGTTGAGCTGACCAGCTCTCTCTTCAGAACAGAGCCAATGG CTTGGAATGAGACTGCTGATCTTGGACTTGATATTGGTGCCCAGGGAGAACCCCTTGGA TATCGCCAGGATGATCCTAGCTATCGTTCTTTTCACTCTGGTGGATATGGCCAGGATGC CTTGGGTATGGACCCCATGATGGAACATGAGATGGGTGGCCACCACCCTGGTGCTGACT ATCCAGTTGATGGGCTGCCAGATCTGGGGCATGCCCAGGACCTCATGGATGGGCTGCCT CCAGGTGACAGCAATCAGCTGGCCTGGTTTGATACTGACCTGTAA | |
| YAP (Human) | ATGGATCCCGGGCAGCAGCCGCCGCCTCAACCGGCCCCCCAGGGCCAAGGGCAGCCGCC TTCGCAGCCCCCGCAGGGGCAGGGCCCGCCGTCCGGACCCGGGCAACCGGCACCCGCGG CGACCCAGGCGGCGCCGCAGGCACCCCCCGCCGGGCATCAGATCGTGCACGTCCGCGGG GACTCGGAGACCGACCTGGAGGCGCTCTTCAACGCCGTCATGAACCCCAAGACGGCCAA CGTGCCCCAGACCGTGCCCATGAGGCTCCGGAAGCTGCCCGACTCCTTCTTCAAGCCGC CGGAGCCCAAATCCCACTCCCGACAGGCCAGTACTGATGCAGGCACTGCAGGAGCCCTG ACTCCACAGCATGTTCGAGCTCATTCCTCTCCAGCTTCTCTGCAGTTGGGAGCTGTTTC TCCTGGGACACTGACCCCCACTGGAGTAGTCTCTGGCCCAGCAGCTACACCCACAGCTC AGCATCTTCGACAGTCTTCTTTTGAGATACCTGATGATGTACCTCTGCCAGCAGGTTGG GAGATGGCAAAGACATCTTCTGGTCAGAGATACTTCTTAAATCACATCGATCAGACAAC AACATGGCAGGACCCCAGGAAGGCCATGCTGTCCCAGATGAACGTCACAGCCCCCACCA GTCCACCAGTGCAGCAGAATATGATGAACTCGGCTTCAGCCATGAACCAGAGAATCAGT CAGAGTGCTCCAGTGAAACAGCCACCACCCCTGGCTCCCCAGAGCCCACAGGGAGGCGT CATGGGTGGCAGCAACTCCAACCAGCAGCAACAGATGCGACTGCAGCAACTGCAGATGG AGAAGGAGAGGCTGCGGCTGAAACAGCAAGAACTGCTTCGGCAGGCAATGCGGAATATC AATCCCAGCACAGCAAATTCTCCAAAATGTCAGGAGTTAGCCCTGCGTAGCCAGTTACC AACACTGGAGCAGGATGGTGGGACTCAAAATCCAGTGTCTTCTCCCGGGATGTCTCAGG AATTGAGAACAATGACGACCAATAGCTCAGATCCTTTCCTTAACAGTGGCACCTATCAC TCTCGAGATGAGAGTACAGACAGTGGACTAAGCATGAGCAGCTACAGTGTCCCTCGAAC CCCAGATGACTTCCTGAACAGTGTGGATGAGATGGATACAGGTGATACTATCAACCAAA GCACCCTGCCCTCACAGCAGAACCGTTTCCCAGACTACCTTGAAGCCATTCCTGGGACA AATGTGGACCTTGGAACACTGGAAGGAGATGGAATGAACATCAAGAAGGAGAGGAGCTGAT GCCAAGTCTGCAGGAAGCTTTGAGTTCTGACATCCTTAATGACATGGAGTCTGTTTTGG CTGCCACCAAGCTAGATAAAGAAAGCTTTCTTACATGGTTATAG | 46 |
| Cyclin D1 (Human) | ATGGAACACCAGCTCCTGTGCTGCGAAGTGGAAACCATCCGCCGCGCGTACCCCGATGC CAACCTCCTCAACGACCGGGTGCTGCGGGCCATGCTGAAGGCGGAGGAGACCTGCGCGC CCTCGGTGTCCTACTTCAAATGTGTGCAGAAGGAGGTCCTGCCGTCCATGCGGAAGATC GTCGCCACCTGGATGCTGGAGGTCTGCGAGGAACAGAAGTGCGAGGAGGAGGTCTTCCC GCTGGCCATGAACTACCTGGACCGCTTCCTGTCGCTGGAGCCCGTGAAAAAGAGCCGCC TGCAGCTGCTGGGGGCCACTTGCATGTTCGTGGCCTCTAAGATGAAGGAGACCATCCCC CTGACGGCCGAGAAGCTGTGCATCTACACCGACAACTCCATCCGGCCCGAGGAGCTGCT GCAAATGGAGCTGCTCCTGGTGAACAAGCTCAAGTGGAACCTGGCCGCAATGACCCCGC ACGATTTCATTGAACACTTCCTCTCCAAAATGCCAGAGGCGGAGGAGAACACAGATC ATCCGCAAACACGCGCAGACCTTCGTTGCCCTCTGTGCCACAGATGTGAAGTTCATTTC CAATCCGCCCTCCATGGTGGCAGCGGGGAGCGTGGTGGCCGCAGTGCAAGGCCTGAACC TGAGGAGCCCCAACAACTTCCTGTCCTACTACCGCCTCACACGCTTCCTCTCCAGAGTG ATCAAGTGTGACCCAGACTGCCTCCGGGCCTGCCAGGAGCAGATCGAAGCCCTGCTGGA GTCAAGCCTGCGCCAGGCCCAGCAGAACATGGACCCCAAGGCCGCCGAGGAGGAGGAAG AGGAGGAGGAGGAGGTGGACCTGGCTTGCACACCCACCGACGTGCGGGACGTGGACATC TGA | 47 |
| c-Myc (Human) | CTGGATTTTTTTCGGGTAGTGGAAAACCAGCCTCCCGCGACGATGCCCCTCAACGTTAG CTTCACCAACAGGAACTATGACCTCGACTACGACTCGGTGCAGCCGTATTTCTACTGCG ACGAGGAGGAGAACTTCTACCAGCAGCAGCAGCAGAGCGAGCTGCAGCCCCCGGCGCCC AGCGAGGATATCTGGAAGAAATTCGAGCTGCTGCCCACCCCGCCCCTGTCCCCTAGCCG CCGCTCCGGGCTCTGCTCGCCCTCCTACGTTGCGGTCACACCCTTCTCCCTTCGGGGAG ACAACGACGGCGGTGGCGGGAGCTTCTCCACGGCCGACCAGCTGGAGATGGTGACCGAG CTGCTGGGAGGAGACATGGTGAACCAGAGTTTCATCTGCGACCCGGACGACGAGACCTT CATCAAAAACATCATCATCCAGGACTGTATGTGGAGCGGCTTCTCGGCCGCCGCCAAGC TCGTCTCAGAGAAGCTGGCCTCCTACCAGGCTGCGCGCAAAGACAGCGGCAGCCCGAAC CCCGCCCGCGGCCACAGCGTCTGCTCCACCTCCAGCTTGTACCTGCAGGATCTGAGCGC CGCCGCCTCAGAGTGCATCGACCCCTCGGTGGTCTTCCCCTACCCTCTCAACGACAGCA GCTCGCCCAAGTCCTGCGCCTCGCAAGACTCCAGCGCCTTCTCTCCGTCCTCGGATTCT CTGCTCTCCTCGACGGAGTCCTCCCCGCAGGGCAGCCCCGAGCCCCTGGTGCTCCATGA GGAGACACCGCCCACCACCAGCAGCGACTCTGAGGAGGAACAAGAAGATGAGGAAGAAA TCGATGTTGTTTCTGTGGAAAAGAGGCAGGCTCCTGGCAAAAGGTCAGAGTCTGGATCA CCTTCTGCTGGAGGCCACAGCAAACCTCCTCACAGCCCACTGGTCCTCAAGAGGTGCCA CGTCTCCACACATCAGCACAACTACGCAGCGCCTCCCTCCACTCGGAAGGACTATCCTG CTGCCAAGAGGGTCAAGTTGGACAGTGTCAGAGTCCTGAGACAGATCAGCAACAACCGA AAATGCACCAGCCCCAGGTCCTCGGACACCGAGGAGAATGTCAAGAGGCGAACACACAA CGTCTTGGAGCGCCAGAGGAGGAACGAGCTAAAACGGAGCTTTTTTGCCCTGCGTGACC AGATCCCGGAGTTGGAAAACAATGAAAAGGCCCCCAAGGTAGTTATCCTTAAAAAAGCC | 48 |

TABLE 2-continued

Suitable Cell Cycle Inducer Sequences

| Cell Cycle Inducer | Nucleotide Sequence | SEQ ID NO: |
|---|---|---|
| | ACAGCATACATCCTGTCCGTCCAAGCAGAGGAGCAAAAGCTCATTTCTGAAGAGGACTT GTTGCGGAAACGACGAGAACAGTTGAAACACAAACTTGAACAGCTACGGAACTCTTGTG CGTAA | |

In some embodiments, the protein of interest is a reporter protein. The reporter protein may be a fluorescent protein. Suitable fluorescent proteins include, without limitation, green fluorescent proteins (e.g., GFP, GFP-2, tagGFP, turboGFP, EGFP, Emerald, Azami Green, Monomeric Azami Green, CopGFP, AceGFP, ZsGreenl), yellow fluorescent proteins (e.g., YFP, EYFP, Citrine, Venus, YPet, PhiYFP, ZsYellowl), blue fluorescent proteins (e.g., EBFP, EBFP2, Azurite, mKalamal, GFPuv, Sapphire, T-sapphire), cyan fluorescent proteins (e.g., ECFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedl, AsRed2, mRasberry, mStrawberry, Jred), and orange fluorescent proteins (mOrange, mKO, Kusabira-Orange, Monomeric Kusabira-Orange, mTangerine, tdTomato), or any other suitable fluorescent protein. In certain embodiments, the reporter protein is a fluorescent protein selected from the group consisting of green fluorescent protein (GFP), enhanced green fluorescent protein (EGFP), and yellow fluorescent protein (YFP).

In some embodiments, the reporter protein is luciferase. As used herein, the term "luciferase" refers to members of a class of enzymes that catalyze reactions that result in production of light. Luciferases have been identified in and cloned from a variety of organisms including fireflies, click beetles, sea pansy (*Renilla*), marine copepods, and bacteria among others. Examples of luciferases that may be used as reporter proteins include, e.g., *Renilla* (e.g., *Renilla reniformis*) luciferase, *Gaussia* (e.g., *Gaussia princeps*) luciferase), *Metridia luciferase*, firefly (e.g., *Photinus pyrahs* luciferase), click beetle (e.g., *Pyrearinus termitilluminans*) luciferase, deep sea shrimp (e.g., *Oplophorus gracihrostris*) luciferase). Luciferase reporter proteins include both naturally occurring proteins and engineered variants designed to have one or more altered properties relative to the naturally occurring protein, such as increased photostability, increased pH stability, increased fluorescence or light output, reduced tendency to dimerize, oligomerize, aggregate or be toxic to cells, an altered emission spectrum, and/or altered substrate utilization.

Exemplary nucleotide sequences encoding suitable reporter proteins are shown in Table 3 below.

TABLE 3

Suitable Reporter Protein Sequences

| Marker Domain Name | Nucleotide Sequence | SEQ ID NO: |
|---|---|---|
| CopGFP | AGAGCGACGAGAGCGGCCTGCCCGCCATGGAGATCGAGTGCCGCATCACCGGCACCCTG AACGGCGTGGAGTTCGAGCTGGTGGGCGGCGGAGAGGGCACCCCCAAGCAGGGCCGCAT GACCAACAAGATGAAGAGCACCAAAGGCGCCCTGACCTTCAGCCCCTACCTGCTGAGCC ACGTGATGGGCTACGGCTTCTACCACTTCGGCACCTACCCCAGCGGCTACGAGAACCCC TTCCTGCACGCCATCAACAACGGCGGCTACACCAACACCCGCATCGAGAAGTACGAGGA CGGCGGCGTGCTGCACGTGAGCTTCAGCTACCGCTACGAGGCCGGCCGCGTGATCGGCG ACTTCAAGGTGGTGGGCACCGGCTTCCCCGAGGACAGCGTGATCTTCACCGACAAGATC ATCCGCAGCAACGCCACCGTGGAGCACCTGCACCCCATGGGCGATAACGTGCTGGTGGG CAGCTTCGCCCGCACCTTCAGCCTGCGCGACGGCGGCTACTACAGCTTCGTGGTGGACA GCCACATGCACTTCAAGAGCGCCATCCACCCCAGCATCCTGCAGAACGGGGGCCCCATG TTCGCCTTCCGCCGCGTGGAGGAGCTGCACAGCAACACCGAGCTGGGGCATCGTGGAGTA CCAGCACGCCTTCAAGACCCCCATCGCCTTCGCCAGATCCCGCGCTCAGTCGTCCAATT CTGCCGTGGACGGCACCGCCGGACCCGGCTCCACCGGATCTCGC | 49 |
| eGFP | ATGGTGAGCAAGGGCGAGGAGCTGTTCACCGGGGTGGTGCCCATCCTGGTCGAGCTGGA CGGCGACGTAAACGGCCACAAGTTCAGCGTGTCCGGCGAGGGCGAGGGCGATGCCACCT ACGGCAAGCTGACCCTGAAGTTCATCTGCACCACCGGCAAGCTGCCCGTGCCCTGGCCC ACCCTCGTGACCACCCTGACCTACGGCGTGCAGTGCTTCAGCCGCTACCCCGACCACAT GAAGCAGCACGACTTCTTCAAGTCCGCCATGCCCGAAGGCTACGTCCAGGAGCGCACCA TCTTCTTCAAGGACGACGGCAACTACAAGACCCGCGCCGAGGTGAAGTTCGAGGGCGAC ACCCTGGTGAACCGCATCGAGCTGAAGGGCATCGACTTCAAGGAGGACGGCAACATCCT GGGGCACAAGCTGGAGTACAACTACAACAGCCACAACGTCTATATCATGGCCGACAAGC AGAAGAACGGCATCAAGGTGAACTTCAAGATCCGCCACAACATCGAGGACGGCAGCGTG CAGCTCGCCGACCACTACCAGCAGAACACCCCCATCGGCGACGGCCCCGTGCTGCTGCC CGACAACCACTACCTGAGCACCCAGTCCGCCCTGAGCAAAGACCCCAACGAGAAGCGCG ATCACATGGTCCTGCTGGAGTTCGTGACCGCCGCCGGGATCACTCTCGGCATGGACGAG CTGTACAAG | 50 |
| YFP | ATGGTGAGCAAGGGCGAGGAGCTGTTCACCGGGGTGGTGCCCATCCTGGTCGAGCTGGA CGGCGACGTAAACGGCCACAAGTTCAGCGTGTCCGGCGAGGGCGAGGGCGATGCCACCT ACGGCAAGCTGACCCTGAAGTTCATCTGCACCACCGGCAAGCTGCCCGTGCCCTGGCCC ACCCTCGTGACCACCTTCGGCTACGGCCTGCAGTGCTTCGCCCGCTACCCCGACCACAT GAAGCAGCACGACTTCTTCAAGTCCGCCATGCCCGAAGGCTACGTCCAGGAGCGCACCA | 51 |

TABLE 3-continued

Suitable Reporter Protein Sequences

| Marker Domain Name | Nucleotide Sequence | SEQ ID NO: |
|---|---|---|
| | TCTTCTTCAAGGACGACGGCAACTACAAGACCCGCGCCGAGGTGAAGTTCGAGGGCGAC ACCCTGGTGAACCGCATCGAGCTGAAGGGCATCGACTTCAAGGAGGACGGCAACATCCT GGGGCACAAGCTGGAGTACAACTACAACAGCCACAACGTCTATATCATGGCCGACAAGC AGAAGAACGGCATCAAGGTGAACTTCAAGATCCGCCACAACATCGAGGACGGCAGCGTG CAGCTCGCCGACCACTACCAGCAGAACACCCCCATCGGCGACGGCCCCGTGCTGCTGCC CGACAACCACTACCTGAGCTACCAGTCCGCCCTGAGCAAAGACCCCAACGAGAAGCGCG ATCACATGGTCCTGCTGGAGTTCGTGACCGCCGCCGGGATCACTCTCGGCATGGACGAG CTGTACAAGTAA | |
| mCherry | ATGGTGAGCAAGGGCGAGGAGGATAACATGGCCATCATCAAGGAGTTCATGCGCTTCAA GGTGCACATGGAGGGCTCCGTGAACGGCCACGAGTTCGAGATCGAGGGCGAGGGCGAGG GCCGCCCCTACGAGGGCACCCAGACCGCCAAGCTGAAGGTGACCAAGGGTGGCCCCCTG CCCTTCGCCTGGGACATCCTGTCCCCTCAGTTCATGTACGGCTCCAAGGCCTACGTGAA GCACCCCGCCGACATCCCCGACTACTTGAAGCTGTCCTTCCCCGAGGGCTTCAAGTGGG AGCGCGTGATGAACTTCGAGGACGGCGGCGTGGTGACCGTGACCCAGGACTCCTCCCTG CAGGACGGCGAGTTCATCTACAAGGTGAAGCTGCGCGGCACCAACTTCCCCTCCGACGG CCCCGTAATGCAGAAGAAGACCATGGGCTGGGAGGCCTCCTCCGAGCGGATGTACCCCG AGGACGGCGCCCTGAAGGGCGAGATCAAGCAGAGGCTGAAGCTGAAGGACGGCGGCCAC TACGACGCTGAGGTCAAGACCACCTACAAGGCCAAGAAGCCCGTGCAGCTGCCCGGCGC CTACAACGTCAACATCAAGTTGGACATCACCTCCCACAACGAGGACTACACCATCGTGG AACAGTACGAACGCGCCGAGGGCCGCCACTCCACCGGCGGCATGGACGAGCTGTACAAG TAA | 52 |
| Luci-ferase | ATGGCCGATGCTAAGAACATTAAGAAGGGCCCTGCTCCCTTCTACCCTCTGGAGGATGG CACCGCTGGCGAGCAGCTGCACAAGGCCATGAAGAGGTATGCCCTGGTGCCTGGCACCA TTGCCTTCACCGATGCCCACATTGAGGTGGACATCACCTATGCCGAGTACTTCGAGATG TCTGTGCGCCTGGCCGAGGCCATGAAGAGGTACGGCCTGAACACCAACCACCGCATCGT GGTGTGCTCTGAGAACTCTCTGCAGTTCTTCATGCCAGTGCTGGGCGCCCTGTTCATCG GAGTGGCCGTGGCCCCTGCTAACGACATTTACAACGAGCGCGAGCTGCTGAACAGCATG GGCATTTCTCAGCCTACCGTGGTGTTCGTGTCTAAGAAGGGCCTGCAGAAGATCCTGAA CGTGCAGAAGAAGCTGCCTATCATCCAGAAGATCATCATCATGGACTCTAAGACCGACT ACCAGGGCTTCCAGAGCATGTACACATTCGTGACATCTCATCTGCCTCCTGGCTTCAAC GAGTACGACTTCGTGCCAGAGTCTTTCGACAGGGACAAAACCATTGCCCTGATCATGAA CAGCTCTGGGTCTACCGGCCTGCCTAAGGGCGTGGCCCTGCCTCATCGCACCGCCTGTG TGCGCTTCTCTCACGCCCGCGACCCTATTTTCGGCAACCAGATCATCCCCGACACCGCT ATTCTGAGCGTGGTGCCATTCCACCACGGCTTCGGCATGTTCACCACCCTGGGCTACCT GATTTGCGGCTTTCGGGTGGTGCTGATGTACCGCTTCGAGGAGGAGCTGTTCCTGCGCA GCCTGCAAGACTACAAAATTCAGTCTGCCCTGCTGGTGCCAACCCTGTTCAGCTTCTTC GCTAAGAGCACCCTGATCGACAAGTACGACCTGTCTAACCTGCACGAGATTGCCTCTGG CGGCGCCCCACTGTCTAAGGAGGTGGGCGAAGCCGTGGCCAAGCGCTTTCATCTGCCAG GCATCCGCCAGGGCTACGGCCTGACCGAGACAACCAGCGCCATTCTGATTACCCCAGAG GGCGACGACAAGCCTGGCGCCGTGGGCAAGGTGGTGCCATTCTTCGAGGCCAAGGTGGT GGACCTGGACACCGGCAAGACCCTGGGAGTGAACCAGCGCGGCGAGCTGTGTGTGCGCG GCCCTATGATTATGTCCGGCTACGTGAATAACCCTGAGGCCACAAACGCCCTGATCGAC AAGGACGGCTGGCTGCACTCTGGCGACATTGCCTACTGGGACGAGGACGAGCACTTCTT CATCGTGGACCGCCTGAAGTCTCTGATCAAGTACAAGGGCTACCAGGTGGCCCCAGCCG AGCTGGAGTCTATCCTGCTGCAGCACCCTAACATTTTCGACGCCGGAGTGGCCGGCCTG CCCGACGACGATGCCGGCGAGCTGCCTGCCGCCGTCGTCGTGCTGGAACACGGCAAGAC CATGACCGAGAAGGAGATCGTGGACTATGTGGCCAGCCAGGTGACAACCGCCAAGAAGC TGCGCGGCGGAGTGGTGTTCGTGGACGAGGTGCCCAAGGGCCTGACCGGCAAGCTGGAC GCCCGCAAGATCCGCGAGATCCTGATCAAGGCTAAGAAAGGCGGCAAGATCGCCGTGTA A | 53 |

As used herein, the term "transfection" refers to the process by which a nucleic acid is introduced into a cell such that they are located inside the cell. Transfection may refer to the uptake of an exogenous nucleic acid, such as modRNA, mRNA, or a plasmid, by a host cell. For example, modRNA can be used to transfect various cell types (e.g., cardiomyocytes) with high efficiency, leading to immediate and high levels of protein expression in a transient, pulse like kinetic (duration of 3-5 days in vitro and 7-10 days in vivo) (see, e.g., Sultana et al., "Optimizing Cardiac Delivery of Modified mRNA," *Mol. Ther.* 25(6):1306-1315 (2017) and Gam et al, "VEGF-A in Patients with Type 2 Diabetes," *Nat. Comm.* 10:871 (2019), which are hereby incorporated by reference in their entirety).

It has recently been shown that modified mRNA (modRNA) can drive a transient, safe gene expression in the heart with high transfection levels without eliciting immune response or compromising the genome (Major & Poss, "Zebrafish Heart Regeneration as a Model for Cardiac Tissue Repair," *Drug Discov. Today Dis. Models* 4(4):219-225 (2007) and Heo & Lee, "β-Catenin Mediates Cyclic Strain-Stimulated Cardiomyogenesis in Mouse Embryonic Stem Cells Through ROS-Dependent and Integrin-Mediated PI3K/Akt Pathways," *J. Cell. Biochem.* 112(7):1880-1889 (2011), which are hereby incorporated by reference in their entirety). As described in more detail above, modRNA is synthesized by substituting ribonucleotides with modified ribonucleotides. The use of these modified ribonucleotides results in changing the secondary structure of the synthe-sized mRNA, which prevents the Toll-like receptors from recognizing the modRNA and permits its translation to a functional protein by the ribosomal machinery within the cell, without eliciting immune response or compromising the genome (Major & Poss, "Zebrafish Heart Regeneration as a Model for Cardiac Tissue Repair," *Drug Discov. Today Dis. Models* 4(4):219-225 (2007) and Heo & Lee, "β-Catenin Mediates Cyclic Strain-Stimulated Cardiomyo-genesis in Mouse Embryonic Stem Cells Through ROS-Dependent and Integrin-Mediated PI3K/Akt Pathways," *J. Cell. Biochem.* 112(7):1880-1889 (2011), which are hereby incorporated by reference in their entirety).

According to some embodiments, the first nucleic acid sequence is capable of increasing translation of a protein of interest in a target cell relative to when the second nucleic acid sequence encoding the protein of interest is operatively coupled to a homologous 5' UTR. In some embodiments, translation of a protein of interest in the target cell is increased by at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more.

As described herein, a target cell may be a mammalian cell. For example, the target cell may be a rodent cell (i.e., mouse or rat cell), rabbit cell, guinea pig cell, feline cell, canine cell, porcine cell, equine cell, bovine cell, ovine cell, monkey cell, or human cell. In certain embodiments, the target cell is a human cell.

Suitable target cells include primary or immortalized cells, at any stage of their lineage, e.g., differentiated cells. Suitable differentiated cells include, without limitation, adipocytes, chondrocytes, endothelial cells, epithelial cells (keratinocytes, melanocytes), bone cells (osteoblasts, osteoclasts), liver cells (cholangiocytes, hepatocytes), muscle cells (cardiomyocytes, skeletal muscle cells, smooth muscle cells), retinal cells (ganglion cells, muller cells, photoreceptor cells), retinal pigment epithelial cells, renal cells (podocytes, proximal tubule cells, collecting duct cells, distal tubule cells), adrenal cells (cortical adrenal cells, medullary adrenal cells), pancreatic cells (alpha cells, beta cells, delta cells, epsilon cells, pancreatic polypeptide producing cells, exocrine cells), lung cells, bone marrow cells (early B-cell development, early T-cell development, macrophages, monocytes), urothelial cells, fibroblasts, parathyroid cells, thyroid cells, hypothalamic cells, pituitary cells, salivary gland cells, ovarian cells, and testicular cells. In some embodiments, the target cell is a cardiomyocyte or hepatocyte.

Another aspect of the disclosure relates to a pharmaceutical composition comprising the nucleic acid molecules described herein.

The pharmaceutical composition may further include a transfection reagent. In some embodiments, the transfection reagent is a positively charged transfection reagent. Suitable transfection reagents are well known in the art and include, e.g., Lipofectamine® RNAiMAX (Invitrogen™), Lipofectamine® 2000 (Invitrogen™), Lipofectamine® 3000 (Invitrogen™), Invivofectamine™ 3.0 (Invitrogen™), Lipofectamine™ MessengerMAX™ (Invitrogen™), Lipofectin™ (Invitrogen™), siLentFet™ (Bio-Rad), DharmaFECT™ (Dharmacon), HiPerFect (Qiagen), TransIT-X2® (Mirus), jetMESSENGER® (Polyplus), Trans-Hi™, JetPEI® (Polyplus), and ViaFect™ (Promega).

The pharmaceutical composition may further comprise a pharmaceutically acceptable carrier. The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients, or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the nucleic acid molecule described herein.

The nucleic acid molecule(s) and/or pharmaceutical composition(s) disclosed herein can be formulated according to any available conventional method. Examples of preferred dosage forms include a tablet, a powder, a subtle granule, a granule, a coated tablet, a capsule, a syrup, a troche, an inhalant, a suppository, an injectable, an ointment, an ophthalmic ointment, an eye drop, a nasal drop, an ear drop, a cataplasm, a lotion and the like. In the formulation, generally used additives such as a diluent, a binder, a disintegrant, a lubricant, a colorant, a flavoring agent, and if necessary, a stabilizer, an emulsifier, an absorption enhancer, a surfactant, a pH adjuster, an antiseptic, an antioxidant, and the like can be used.

In addition, formulating a pharmaceutical composition can be carried out by combining compositions that are generally used as a raw material for pharmaceutical formulation, according to conventional methods. Examples of these compositions include, for example, (1) an oil such as a soybean oil, a beef tallow and synthetic glyceride; (2) hydrocarbon such as liquid paraffin, squalane and solid paraffin; (3) ester oil such as octyldodecyl myristic acid and isopropyl myristic acid; (4) higher alcohol such as cetostearyl alcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, a solid polyoxyethylene castor oil and polyoxyethylene polyoxypropylene block co-polymer; (8) water soluble macromolecule such as hydroxyethyl cellulose, polyacrylic acid, carboxyvinyl polymer, polyethyleneglycol, polyvinylpyrrolidone and methylcellulose; (9) lower alcohol such as ethanol and isopropanol; (10) multivalent alcohol such as glycerin, propyleneglycol, dipropyleneglycol and sorbitol; (11) a sugar such as glucose and cane sugar; (12) an inorganic powder such as anhydrous silicic acid, aluminum magnesium silicicate, and aluminum silicate; (13) purified water, and the like.

Additives for use in the above formulations may include, for example, (1) lactose, corn starch, sucrose, glucose, mannitol, sorbitol, crystalline cellulose, and silicon dioxide as the diluent; (2) polyvinyl alcohol, polyvinyl ether, methyl cellulose, ethyl cellulose, gum arabic, tragacanth, gelatine, shellac, hydroxypropyl cellulose, hydroxypropylmethyl cellulose, polyvinylpyrrolidone, polypropylene glycol-polyoxyethylene-block co-polymer, meglumine, calcium citrate, dextrin, pectin, and the like as the binder; (3) starch, agar, gelatine powder, crystalline cellulose, calcium carbonate, sodium bicarbonate, calcium citrate, dextrin, pectic, carboxymethylcellulose/calcium, and the like as the disintegrant; (4) magnesium stearate, talc, polyethyleneglycol, silica, condensed plant oil, and the like as the lubricant; (5) any colorant whose addition is pharmaceutically acceptable is adequate as the colorant; (6) cocoa powder, menthol, aromatizer, peppermint oil, cinnamon powder as the flavoring agent; (7) antioxidants whose addition is pharmaceutically accepted such as ascorbic acid or alpha-tophenol.

Another aspect of the present application relates to a method of expressing a protein of interest in a target cell. This method involves providing the nucleic acid molecule or a pharmaceutical composition described herein and contacting a target cell with the nucleic acid molecule or pharmaceutical composition. The nucleic acid molecule is translated to express the protein of interest in the target cell.

As described above, the target cell may be a mammalian cell. For example, the target cell may be a rodent cell (i.e., mouse or rat cell), rabbit cell, guinea pig cell, feline cell, canine cell, porcine cell, equine cell, bovine cell, ovine cell, monkey cell, or human cell. In certain embodiments, the target cell is a human cell.

Suitable target cells are described in detail above and include, without limitation, adipocytes, chondrocytes, endothelial cells, epithelial cells (keratinocytes, melanocytes), bone cells (osteoblasts, osteoclasts), liver cells (cholangiocytes, hepatocytes), muscle cells (cardiomyocytes, skeletal muscle cells, smooth muscle cells), retinal cells (ganglion cells, muller cells, photoreceptor cells), retinal pigment epithelial cells, renal cells (podocytes, proximal tubule cells, collecting duct cells, distal tubule cells), adrenal cells (cortical adrenal cells, medullary adrenal cells), pancreatic cells (alpha cells, beta cells, delta cells, epsilon cells, pancreatic polypeptide producing cells, exocrine cells); lung cells, bone marrow cells (early B-cell development, early T-cell development, macrophages, monocytes), urothelial cells, fibroblasts, parathyroid cells, thyroid cells, hypothalamic cells, pituitary cells, salivary gland cells, ovarian cells, and testicular cells. In a particular embodiment, the target cell is a cardiomyocyte or hepatocyte.

In certain embodiments of the methods described herein, the target cell is an ischemic cell. The term "ischemic" or "ischemia" refers to a reduction in blood flow. Ischemia is associated with a reduction in nutrients, including oxygen, delivered to tissues. Ischemia may arise due to conditions such as atherosclerosis; formation of a thrombus in an artery or vein; or blockage of an artery or vein by an embolus, vascular closure due to other causes, e.g., vascular spasm. Such conditions may reduce blood flow, producing a state of hypoperfusion to an organ or tissue, or block blood flow completely. Other conditions that can produce ischemia include tissue damage due to trauma or injury, such as, e.g., spinal cord injury or viral infection, which can lead to, e.g., congestive heart failure.

The term "ischemic condition" refers to acute ischemic conditions, including myocardial infarction (MI), ischemic stroke, pulmonary embolism, perinatal hypoxia, circulatory shock (e.g., hemorrhagic, septic, cardiogenic, mountain sickness, acute respiratory failure) and chronic ischemic conditions, including atherosclerosis, chronic venous insufficiency, chronic heart failure, cardiac cirrhosis, diabetes, macular degeneration, sleep apnea, Raynaud's disease, systemic sclerosis, nonbacterial thrombotic endocarditis, occlusive artery disease, angina pectoris, TIAs, and chronic alcoholic liver disease. Ischemic conditions may also result when individuals are placed under general anesthesia, which can cause tissue damage in organs prepared for transplant. Myocardial ischemic conditions (e.g., myocardial infarction) result in damage to cardiomyocytes.

In some embodiments, the target cell is an ischemic cardiomyocyte. When the target cell is a cardiomyocyte, the nucleic acid molecule may be translated to express the protein of interest in the heart.

Liver ischemia is a major complication in many clinical scenarios, such as liver resection, liver transplantation, and trauma (see, e.g., Konishi et al., "Hepatic Ischemia/Reperfusion: Mechanisms of Tissue Injury, Repair, and Regeneration," *Gene Expr.* 17(4):277-287, which is hereby incorporated by reference in its entirety). Hepatocytes, which comprise the main parenchymal tissue of the liver, may be damaged during liver ischemia. Thus, in some embodiments, the target cell is an ischemic hepatocyte. When the target cell is a hepatocyte, the nucleic acid molecule may be translated to express the protein of interest in the liver.

According to some embodiments, both cardiomyocytes and hepatocytes are contacted, and the nucleic acid molecule is translated to express the protein of interest in the heart and the liver.

In some embodiments, the contacting is carried out after an ischemic event in the target cell. Suitable ischemic events are associated with ischemic conditions, which are described in detail above and include, e.g., myocardial infarction (MI), ischemic stroke, pulmonary embolism, perinatal hypoxia, and circulatory shock.

The Examples below demonstrate the ability of a modRNA construct comprising a first nucleic acid sequence having at least a portion of a 5' UTR of a carboxylase gene and a second nucleic acid sequence encoding a reporter protein to selectively enhance translation of the reporter protein in cells that have undergone ischemia as compared to non-ischemic cells. Thus, in some embodiments, the contacting is effective to increase translation of the protein of interest in an ischemic target cell relative to a non-ischemic target cell. Suitable proteins of interest are described in detail above and include, e.g., Lin28 and Pkm2.

modRNA constructs can be used for the transient expression of target proteins of interest. Thus, in some embodiments, the protein of interest is transiently expressed. The protein of interest may be transiently expressed for a period of 1, 2, 3, 4, 5, 6, 7, 8, 9, 10, or more days. In some embodiments, the protein of interest is transiently expressed for 3-7 days.

A further aspect of the present application relates to a method of treating a subject for cardiac ischemia or hepatic ischemia. This method involves providing the nucleic acid molecule or a pharmaceutical composition described herein and contacting the subject with the nucleic acid molecule or pharmaceutical composition described herein, where the nucleic acid molecule is translated to express a protein of interest in the subject's heart or liver to treat the subject for cardiac ischemia or hepatic ischemia.

In carrying out the methods of the present application, "treating" or "treatment" includes inhibiting, preventing, ameliorating or delaying onset of a particular condition. Treating and treatment also encompasses any improvement in one or more symptoms of the condition or disorder. Treating and treatment encompasses any modification to the condition or course of disease progression as compared to the condition or disease in the absence of therapeutic intervention.

The terms "disorders" and "diseases" are used inclusively and refer to any condition deviating from normal. Thus, the term "ischemic condition(s)" refers to any condition, disease, or disorder that is associated with ischemia.

Suitable subjects for treatment according to the methods of the present application include, without limitation, domesticated and undomesticated animals such as rodents (mouse or rat), cats, dogs, rabbits, horses, sheep, pigs, and monkeys. In some embodiments the subject is a human subject. Exemplary human subjects include, without limitation, infants, children, adults, and elderly subjects.

In some embodiments, the subject is in need of treatment for an acute ischemic condition. Suitable acute ischemic conditions are described in detail above and include, e.g., myocardial infarction (MI), ischemic stroke, pulmonary embolism, perinatal hypoxia, and circulatory shock.

In some embodiments, the subject is in need of treatment for a chronic ischemic condition. Suitable chronic ischemic conditions are described above and include, e.g., atherosclerosis, chronic venous insufficiency, chronic heart failure, cardiac cirrhosis, diabetes, macular degeneration, sleep apnea, Raynaud's disease, systemic sclerosis, nonbacterial thrombotic endocarditis, occlusive artery disease, angina pectoris, TIAs, and chronic alcoholic liver disease.

In some embodiments, the subject is in need of treatment for a disorder characterized by insufficient cardiac function. In some embodiments, the methods disclosed herein are useful for treatment of a disease or disorder which is congestive heart failure, cardiomyopathy, myocardial infarction, tissue ischemia, cardiac ischemia, vascular disease, acquired heart disease, congenital heart disease, atherosclerosis, cardiomyopathy, dysfunctional conduction systems, dysfunctional coronary arteries, pulmonary heard hypertension. In some embodiments, the disease is selected from the group consisting of congestive heart failure, coronary artery disease, myocardial infarction, myocardial ischemia, atherosclerosis, cardiomyopathy, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, an autoimmune endocarditis, congenital heart disease, and combinations thereof.

In some embodiments, the contacting is effective to reduce at least one symptom of an ischemic disease or condition that is associated with the loss or dysfunction of the target cell type. In other embodiments, the contacting is effective to mediate an improvement in the ischemic disease or condition that is associated with the loss or dysfunction of the target cell type. In certain embodiments, the contacting is effective to prolong survival in the subject following an ischemic event as compared to expected survival if no contacting were carried out.

The methods described herein may be carried out to treat a subject for cardiac ischemia, hepatic ischemia, or both cardiac and hepatic ischemia. In some embodiments, the subject is treated for cardiac ischemia and cardiomyocytes in the subject are contacted with the nucleic acid molecule. In other embodiments, the subject is treated for hepatic ischemia and hepatocytes in the subject are contacted with the nucleic acid molecule. When the method is carried out to treat the subject for both cardiac ischemia and hepatic ischemia, cardiomyocytes and hepatocytes in the subject are contacted with the nucleic acid molecule.

In some embodiments, cardiomyocytes and hepatocytes in the subject are contacted with the pharmaceutical composition described herein. According to such embodiments, the contacting is carried out by injection.

As described herein above, the protein of interest may be transiently expressed. The term "transient expression" refers to expression of a protein of interest from a non-integrated transgene for a period of hours, days, or weeks, where the period of time of expression is less than the period of time for expression of the protein of interest if the transgene were integrated into the genome or contained within a stable plasmid replicon in a target host cell.

The protein of interest may be a cell cycle inducer. Suitable cell cycle inducer proteins are described above and include, e.g., Lin28 and Pyruvate Kinase Muscle Isozyme M2 (Pkm2).

In some embodiments, the contacting is effective to deliver the nucleic acid molecule or pharmaceutical composition described herein to a specific tissue in the subject. The tissue may be muscle tissue. For example, the muscle tissue may be skeletal muscle, cardiac muscle, or smooth muscle. In some embodiments, the tissue is the myocardium.

Contacting, according to the methods of the present application, may be carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Thus, in some embodiments, the contacting is carried out intramuscularly, intravenously, subcutaneously, orally, or intraperitoneally. In specific embodiments, the contacting is carried out by direct intra-myocardial injection.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Suitable regimens for initial contacting and further doses or for sequential contacting steps may all be the same or may be variable. Appropriate regimens can be ascertained by the skilled artisan, from this disclosure, the documents cited herein, and the knowledge in the art.

An in vitro dosage unit (e.g., for contacting target cells in a 6-well, 12-well, 24-well, or 96-well plate) can include from, for example, 0.1 to 10 µg, 0.5 to 10 µg, 1 to 5 µg, 1 to 10 µg, 1 to 15 µg, and 1 to 20 µg (e.g., 0.1 µg, 0.2 µg, 0.3 µg, 0.4 µg, 0.5 µg, 0.6 µg, 0.7 µg, 0.8 µg, 0.9 µg, 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg) of a compound described herein.

An in vivo dosage unit (e.g., for contacting target cells within a subject) can include from, for example, 1 to 100 µg, 10 to 100 µg, 15 to 100 µg, 20 to 100 µg, 25 to 100 µg, and 1 to 200 µg (e.g., 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg, 200 µg) of a compound described herein. In some embodiments, the in vivo dosage unit includes, for example, 1 to 10 mg, 1 to 20 mg, 1 to 30 mg, 1 to 40 mg, 1 to 50 mg, 1 to 60 mg, 1 to 70 mg, 1 to 80 mg, 1 to 90 mg, 1 to 100 mg, 10 to 100 mg, 20 to 100 mg, 30 to 100 mg, 40 to 100 mg, 50 to 100 mg, 60 to 100 mg, 70 to 100 mg, 80 to 100 mg, and 90 to 100 mg (e.g., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg) of a compound described herein.

In some embodiments, a subject is contacted with the nucleic acid molecule or pharmaceutical composition described herein in one dose. In other embodiments, the subject is contacted with the nucleic acid molecule or pharmaceutical composition described herein in a series of two or more doses in succession. In some other embodiments, where the subject is contacted with the nucleic acid molecule or pharmaceutical composition described herein in a single dose, in two doses, and/or more than two doses, the doses may be the same or different, and they are administered with equal or with unequal intervals between them.

A subject may be contacted with the nucleic acid molecule or pharmaceutical composition described herein in many frequencies over a wide range of times. In some embodiments, the subject is contacted over a period of less than one day. In other embodiments, the subject is contacted over two, three, four, five, or six days. In some embodiments, the contacting is carried out one or more times per week, over a period of weeks. In other embodiments, the contacting is carried out over a period of weeks for one to several months. In various embodiments, the contacting is carried out over a period of months. In others, the contacting may be carried out over a period of one or more years. Generally, lengths of treatment will be proportional to the length of the ischemic disease process, the effectiveness of the therapies being applied, and the condition and response of the subject being treated. According to some embodiments, the contacting is carried out daily.

The choice of formulation for contacting a subject with the nucleic acid molecule or pharmaceutical composition described herein will depend on a variety of factors. Prominent among these will be the species of subject, the nature of the disorder, dysfunction, or disease being treated and its state and distribution in the subject, the nature of other therapies and agents that are being administered, the optimum route for administration, survivability via the route, the dosing regimen, and other factors that will be apparent to those skilled in the art. In particular, for instance, the choice of suitable carriers and other additives will depend on the exact route of contacting and the nature of the particular dosage form.

Yet another aspect of the present application relates to a method of identifying a 5' untranslated region (5' UTR) for selectively enhancing translation of a heterologous protein of interest in a target cell or tissue. This method involves obtaining a first sample of living tissue comprising a target cell under disease conditions and a second sample of living tissue comprising the target cell under non-disease conditions; quantifying genes that are transcribed and translated in the first and second samples; identifying genes which (i) are transcribed at similar or lower levels in the first sample relative to the second sample and (ii) are translated at higher levels in the first sample relative to the second sample; and identifying the 5' UTR of the identified genes, where the identified 5' UTR is capable of selectively enhancing translation of a heterologous protein of interest in a target cell or tissue.

Figure 10A:
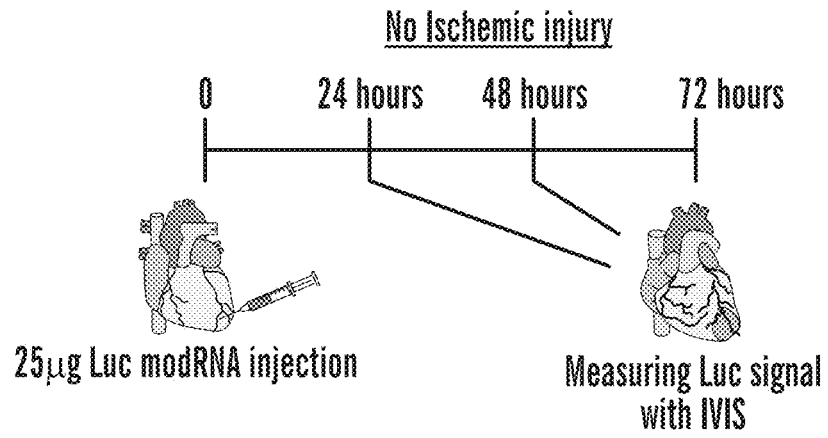
FIGS. 10A-10B demonstrate that Element D in the 5' UTR of Ces1d does not significantly increase mRNA translation over the full length 5' UTR of Ces1d or control 5' UTR in a heart non-ischemic mouse model.
Figure 11:
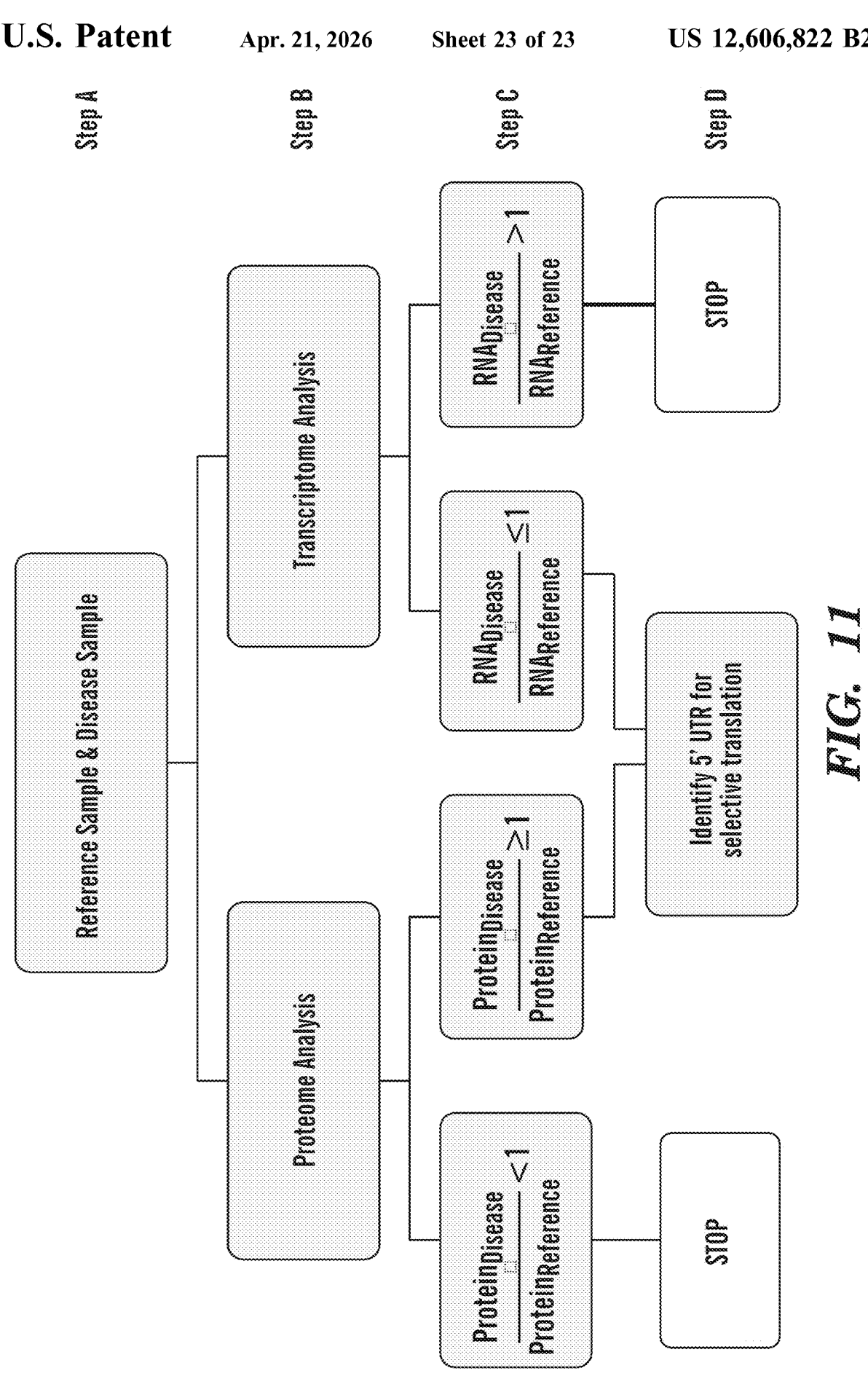
FIG. 11 is a flow diagram illustrating one embodiment of a method of identifying a 5' untranslated region (5' UTR) for selectively enhancing translation of a heterologous protein of interest in a target cell or tissue. Step A corresponds to obtaining a disease sample (i.e., a first sample of living tissue comprising a target cell under disease conditions) and a reference sample (i.e., second sample of living tissue comprising the target cell under non-disease conditions); step B corresponds to proteome analysis (i.e., quantifying genes that are translated) and transcriptome analysis (i.e., quantifying genes that are transcribed) in the disease and reference samples (i.e., the first and second samples); step C corresponds to identifying genes which (i) are transcribed at similar or lower levels in the first sample relative to the second sample and (ii) are translated at higher levels in the first sample relative to the second sample; and step D corresponds to identifying the 5' UTR of the identified genes, where the identified 5' UTR is capable of selectively enhancing translation of a heterologous protein of interest in a target cell or tissue.

FIG. 11 is a flow diagram illustrating one embodiment of a method of identifying a 5' untranslated region (5' UTR) described herein. In FIG. 10A, step A corresponds to the step of obtaining a disease sample (i.e., a first sample of living tissue comprising a target cell under disease conditions) and a reference sample (i.e., second sample of living tissue comprising the target cell under non-disease conditions); step B corresponds to proteome analysis (i.e., quantifying genes that are translated) and transcriptome analysis (i.e., quantifying genes that are transcribed) in the disease and reference samples (i.e., the first and second samples); step C corresponds to identifying genes which (i) are transcribed at similar or lower levels in the first sample relative to the second sample and (ii) are translated at higher levels in the first sample relative to the second sample; and step D corresponds to identifying the 5' UTR of the identified genes, where the identified 5' UTR is capable of selectively enhancing translation of a heterologous protein of interest in a target cell or tissue.

In some embodiments, the identified 5' UTR corresponds to a gene that encodes a protein that is translated at least 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.3-fold, 2.4-fold, 2.5-fold, 2.6-fold, 2.7-fold, 2.8-fold, 2.9-fold, or 3.0-fold greater under a disease condition than under a reference condition. The identified 5' UTR may correspond to a gene that encodes a protein that is transcribed at least 0.9-fold, 0.8-fold, 0.7-fold, 0.6-fold, 0.5-fold, 0.4-fold, 0.3-fold, 0.2-fold, or 0.1-fold less under a disease condition than under a reference condition.

The method may further involve selecting genes with a 5' UTR of less than 100 nucleotides before or after identifying the 5' UTR of the identified genes.

In some embodiments, the method further involves providing a first modified mRNA (modRNA) construct encoding a reporter protein operably coupled to the identified 5' UTR; providing a second modRNA construct encoding a reporter protein operably coupled to a reference 5' UTR; expressing the first modRNA construct and the second modRNA construct in a cell or tissue of interest under disease conditions and non-disease conditions; measuring the expression of the reporter protein from each of the first and second modRNA constructs under disease and non-disease conditions; and determining whether the identified 5' UTR of the first modRNA construct selectively enhances protein translation in a disease tissue as compared to the reference 5' UTR of the second modRNA construct.

The method according to this aspect of the present application may further involve providing a modRNA molecule comprising a heterologous protein of interest operably coupled to a portion of the identified 5' UTR and comparing translation of the protein of interest in the target cell under disease conditions to the translation of the protein of interest in the target cell under non-disease conditions; and identifying, based on said comparing, a nucleic acid sequence that selectively enhances translation of the protein of interest from the modRNA molecule under disease conditions. In some embodiments, the protein of interest is not a reporter protein. The protein of interest may comprise a cell cycle inducer. Suitable cell cycle inducers are described above and include, e.g., Lin28 and Pkm2.

Suitable modRNA modifications are described in detail above. In some embodiments, the modRNA comprises pseudouridine or methylpseudouridine.

In some embodiments, the disease condition is ischemia. Suitable ischemic conditions are described in detail above and include, e.g., acute and chronic ischemic conditions.

In some embodiments, the disease is cancer, an autoimmune disorder, bacterial infection, viral infection, inflammation, fibrotic disorder, metabolic disorder, a neoplasm, cardiovascular or cerebrovascular disorder, a skin disorder, or any disease or disorder in which it is or may be desirable to express a therapeutic protein of interest to improve the disease condition in a cell, tissue, or subject.

According to certain embodiments, the samples are obtained from a mammal. For example, the sample may be a rodent (e.g., a mouse or rat) sample, a rabbit sample, a guinea pig sample, a feline sample, a canine sample, a porcine sample, an equine sample, a bovine sample, an ovine sample, a non-human primate (e.g., a monkey) sample, or human sample. In some embodiments, the mammal is a rodent or a human. The human may be, without limitation, an infant, a child, an adult, or an elderly adult.

The present application may be further illustrated by reference to the following examples.

EXAMPLES

The examples below are intended to exemplify the practice of embodiments of the disclosure but are by no means intended to limit the scope thereof.

Materials and Methods for Examples 1-7

Mice

All animal procedures were performed according to protocols approved by the Icahn School of Medicine at Mount Sinai Institutional Care and Use Committee. CFW mice were used for the study. Before surgery, mice were anesthetized with a cocktail of 100 mg/kg ketamine and 10 mg/kg xylazine. For protein expression, mice received 25 µg of modRNA in citrate buffer injected directly into the myocardium during open-chest surgery. When required, 25 µg of modRNA was injected into the border zone with three injections immediately after left anterior descending artery (LAD) ligation.

ModRNA Synthesis

Clean PCR products generated with plasmid templates (GeneArt, ThermoFisher Scientific) were used as the template for mRNA. modRNAs were generated by transcription in vitro with a customized ribonucleoside blend of anti-reverse cap analog, 3'-O-Me-m7G(5')ppp(5')G (6 mM, Tri-Link Biotechnologies) or with Anti-Reverse Cap Analog (ARCA) or CleanCap® Reagent AG, guanosine triphosphate (1.5 mM, Life Technologies), adenosine triphosphate (7.5 mM, Life Technologies), cytidine triphosphate (7.5 mM, Life Technologies), and N1-methylpseudouridine-5-triphosphate (7.5 mM, TriLink Biotechnologies). The mRNA was purified with the MEGAclear™ kit (Life Technologies) and treated with Antarctic Phosphatase (New England Biolabs). It was then re-purified with the MEGAclear™ kit. The mRNA was quantified on a NanoDrop™ spectrometer (ThermoFisher Scientific), precipitated with ethanol and ammonium acetate, and resuspended in 10 mM Tris-HCl and 1 mM EDTA.

Rat Neonatal Cardiomyocytes (RNCM) Isolation

Ventricular RNCMs were isolated from 3-4 day-old Sprague-Dawley rat pups using the Pierce™ Primary Cardiomyocyte Isolation Kit (ThermoFisher Scientific, Catalog No. 88282). After isolation, cells were incubated in 10% horse serum DMEM; after 16 hours, media was changed, cardiomyocyte growth supplement was added, and cells were transfected with modRNA.

In Vitro modRNA Transfection

Either 2.5 µg/well in a 24-well plate of luciferase (Luc) modRNA or 10 µg/well in a 6-well plate of nGFP modRNA was transfected into neonatal rat cardiomyocytes (CMs) using the transfection reagent JetPEI® (Polyplus). The transfection mixture was prepared according to the manufacturer's protocol and then added to cells cultured in DMEM medium containing 10% fetal bovine serum (FBS) and Anti-anti. Then, 24-hours post-transfection, either cells were imaged to measure expression level in IVIS® (FIGS. 5A-5F) or cell lysates were collected and analyzed by western blot.

Heart Ischemic Injury

Myocardial Infarction (MI) was induced by permanently ligating the left anterior descending artery (LAD). The left thoracic region was shaved and sterilized. After intubation, the heart was exposed by left thoracotomy. The LAD was ligated with a suture. Mouse hearts without (sham) or with ischemic injury (MI) were collected at 4 and 23 hours post-MI (FIG. 1A). The ischemic area tissue (or equivalent area in sham-operated hearts) was collected, divided into two pieces, and quickly snap-frozen. Half of the ischemic heart tissues was sent for RNAseq while the other half was sent for proteomics analysis to evaluate gene and protein fold change, respectively, between MI versus sham-operated hearts.

When required, 25 µg modRNA was injected into the infarct border zone immediately after LAD ligation. The thoracotomy and skin were sutured closed in layers. Excess air was removed from the thoracic cavity, and the mouse was removed from ventilation when normal breathing was established.

Liver Ischemic Injury

Liver ischemia was induced by closing left lateral lobe and median for an hour. Three injections of 25 µg modRNA were injected into the left lateral lobe immediately after the clip was removed.

Kidney Ischemic Injury

Kidney ischemia was induced by applying a micro clip to the renal artery and renal vein. Successful ischemia can be visually confirmed by a gradual uniform darkening of the kidney. The clip was removed after 30 minutes and three injections of 25 µg modRNA were injected into the kidney.

In Vivo modRNA Delivery

25 µg Luc modRNA in a total volume of 60 µl in TB buffer was delivered via direct injection to the myocardium. The sucrose-citrate buffer contained 20 µl sucrose in nuclease-free water (0.3 g/mL) and 20 µl citrate (0.1 M, pH 7; Sigma) mixed with 20 µL modRNA. The transfection mixture was directly injected (three individual injections, 20 µl each) into the heart, kidney, or liver.

Detecting of Luciferase Expression Using the IVIS® In Vivo Imaging System

Bioluminescence imaging of the transfected cells (24-72 hours) or injected mice was taken at different time points (4-144 hours) using the IVIS® system. To visualize cells expressing Firefly luciferase (Luc) in vitro, D-luciferin was added to cell culture plates and images were taken in the IVIS® system (IVIS® Spectrum NCRR S10-RR026561-01). To visualize cells expressing *Renilla* luciferase in vitro, cells were washed twice with media and *Renilla* luciferase substrate was added to cell culture plates. Images were taken using an emission filter 500. To visualize tissues expressing Luc in vivo, mice were anesthetized with isoflurane (Abbott Laboratories), and luciferin (150 µg/g body weight; Sigma) was injected intraperitoneally. Mice were imaged using the IVIS® imaging system every 2 minutes until the Luc signal reached a plateau. Imaging data were analyzed and quantified with Living Image® software (PerkinElmer).

Western Blotting

Cell lysates were collected and subjected to SDS-PAGE in 12% precast Nupage Bis/Tris gels (Invitrogen) under reducing conditions in IVIES running buffer (Invitrogen). The resulting bands were transferred onto a nitrocellulose membrane (Bio-Rad) by blotting in a semidry transfer apparatus with Nupage-MOPS transfer buffer (Invitrogen). The membrane was blocked by incubation with TB S/TWEEN® containing 5% dry milk powder and incubated with specific primary antibodies overnight at 4° C. It was then washed in TBS/TWEEN® and incubated with rabbit or goat secondary antibodies conjugated to horseradish peroxidase for 1 hour at room temperature. Antibody binding was detected with an enhanced chemiluminescence (ECL) detection system (Pierce). Prestained protein standards (Amersham) were used to determine molecular weight.

RNA Isolation

Total RNA was isolated with RNeasy® Mini Kit (QIA-GEN) and DNA was degraded by treatment with TURBO DNase (Invitrogen). RNA quality was checked by bioanalyzer.

RNA Sequencing

Poly(A)-tailed RNA was prepared by the Epigenomics Core at Cornell Medical College, with the mRNA Seq Sample Prep Kit (Illumina), and used to create libraries for HiSeq2000 sequencing (Illumina). Single 50 bp reads were used for sequencing. A mean of 30 million reads per sample was obtained, with a mean quality score of 35.2. Partek® Flow® software was used for data analysis. RNA-Seq reads were aligned to mm10 with STAR version 2.53a. Read counts were generated by applying the Partek E/M algorithm to UCSC RefSeq 2017-08-02. Counts were normalized with the TMM algorithm and the Partek® Flow® GSA algorithm was used for statistical analysis. The RNAseq data used in this study are available using accession #GSE138201, which is hereby incorporated by reference in its entirety.

Protein Mass Spectrometry

All solvents were HPLC grade, from Sigma-Aldrich, and all chemicals where not stated otherwise were obtained from Sigma-Aldrich. For ample preparation, samples were lysed in Biognosys' Lysis Buffer with a TissueLyserII bead mill (QIAGEN) using stainless steel grinding beads for 3 minutes at 30 Hz. Samples were treated with benzonase after lysis to reduce DNA contamination. Protein concentrations of the lysates were estimated using a UV/VIS Spectrometer (SPECTROstar Nano, BMG LABTECH). Approximately 100 μg of protein from each sample were denatured using Biognosys' Denature Buffer, reduced using Biognosys' Reduction Solution for 60 minutes at 37° C. and alkylated using Biognosys' Alkylation Solution for 30 minutes at room temperature in the dark. Subsequently, digestion to peptides was carried out using 3 μg of trypsin (Promega) overnight at 37° C.

Peptides were desalted using C18 MacroSpincolumns (The Nest Group) according to the manufacturer's instructions and dried down using a SpeedVac system. Next, peptides were resuspended in 50 μl LC solvent A (1% acetonitrile, 0.1% formic acid (FA)) and spiked with Biognosys' iRT kit calibration peptides. Peptide concentrations were determined using a UV/VIS Spectrometer (SPECTROstar Nano, BMG LABTECH).

For HPRP fractionation, equal-volume samples from each condition were pooled. Ammonium hydroxide was added to all pools to a pH value>10. The fractionation was performed using a Dionex UltiMate 3000 RS Pump (Thermo Scientific) on an Acquity UPLC CSH C18 1.7 μm, 2.1×150 mm column (Waters). The gradient was 2% to 35% Solvent B in 10 min; solvents were A: 20 mM ammonium formate in H₂O, B: Acetonitrile. Fractions were taken every 15 sec and sequentially pooled to 4 fraction pools. These were dried down and resolved in 20 μl solvent A. Prior to mass spectrometric analyses, they were spiked with Biognosys' iRTkit calibration peptides. Peptide concentrations were determined using a UV/VIS Spectrometer (SPECTROstar Nano, BMG LABTECH).

For the LC-MS/MS (shotgun) measurements, 2 μg of peptides were injected to an in-house packed C18 column (ReproSil-Pur® (Maisch), 1.9 μm particle size, 120 Å pore size; 75 μm inner diameter, 50 cm length, New Objective) on a nano-liquid chromatography system (Easy nLC™ 1200 System, ThermoFisher Scientific) connected to a Q Exactive™ HF (ThermoFisher Scientific) mass spectrometer equipped with a standard nano-electrospray source. LC solvents were A: 1% acetonitrile in water with 0.1% FA; B: 15% water in acetonitrile with 0.1% FA. The non-linear LC gradient was 1-55% solvent B in 60 minutes followed by 55-90% B in 10 seconds, 90% B for 10 minutes, 90%-1% B for 10 seconds and 1% B for 5 minutes. A modified TOP15 method was used (Scheltema et al., "The Q Exactive HF, a Benchtop Mass Spectrometer with a Pre-Filter, High-Performance Quadrupole and an Ultra-High-Field Orbitrap Analyzer," Mol. Cell Proteomics 13:3698-3708 (2014), which is hereby incorporated by reference in its entirety).

The mass spectrometric data were analyzed using Biognosys' search engine Pulsar (version 1.0.16105), with the false discovery rate on peptide and protein level set to 1%. A mouse UniProt FASTA database (Mus musculus, 2017-07-01) was used for the search engine, allowing for 2 missed cleavages and variable modifications (N-term acetylation, methionine oxidation).

For the LC-MS/MS HRM measurements, 2 μg of peptides per sample were injected into C18 column (ReproSil-Pur® (Maisch), 1.9 μm particle size, 120 Å pore size; 75 μm inner diameter, 50 cm length, New Objective) on a nano-liquid chromatography system (Easy nLC™ 1200 System, ThermoFisher Scientific) connected to a Q Exactive™ HF (ThermoFisher Scientific) mass spectrometer equipped with a standard nano-electrospray source. LC solvents were A: 1% acetonitrile in water with 0.1% formic acid; B: 15% water in acetonitrile with 0.1% formic acid. The nonlinear LC gradient was 1-52% solvent B in 60 minutes followed by 52-90% B in 10 seconds and 90% B for 10 minutes. A DIA method with one full range survey scan and 14 DIA windows was used.

HRM mass spectrometric data were analyzed using Spectronaut™ Pulsar software (Biognosys). The false discovery rate on peptide and protein levels was set to 1%; data were filtered using row based extraction. The assay library (protein inventory) generated in this project was used for the analysis. The HRM measurements analyzed with Spectronaut™ were normalized using local regression normalization (Callister et al., "Normalization Approaches for Removing Systematic Biases Associated with Mass Spectrometry and Label-Free Proteomics," J. Proteome Res. 5:277-286 (2006), which is hereby incorporated by reference in its entirety).

Merging Proteomics and Transcriptomics Data

For proteomics/transcriptomics merging, gene IDs contained in the transcriptomics data sets were matched to gene names in the mouse UniProt Swiss-Prot proteome.

Statistical Analysis for Luciferase Activity Assay and RNA Protein Correlation

All statistical analysis was performed with GraphPad-Prism software. Values are reported as means±SD. One-way ANOVA with Bonferroni correction (*p<0.05 considered significant) was used for comparisons among groups. Parson R correlation was calculated for correlation between changes in mRNA expression and protein levels.

Example 1—Characterizing the Ischemic Heart Transcriptome and Proteome

To characterize the dynamics of the heart LV transcriptome and proteome post-MI, changes in gene expression and protein levels in the LV of mice at 4-hours and at 24-hours post-MI were analyzed and compared to changes to the LV from sham-operated mice (FIG. 1A). In total, 14,552 genes and 2,397 proteins were detected in the analyzed samples.

Figure 1C:
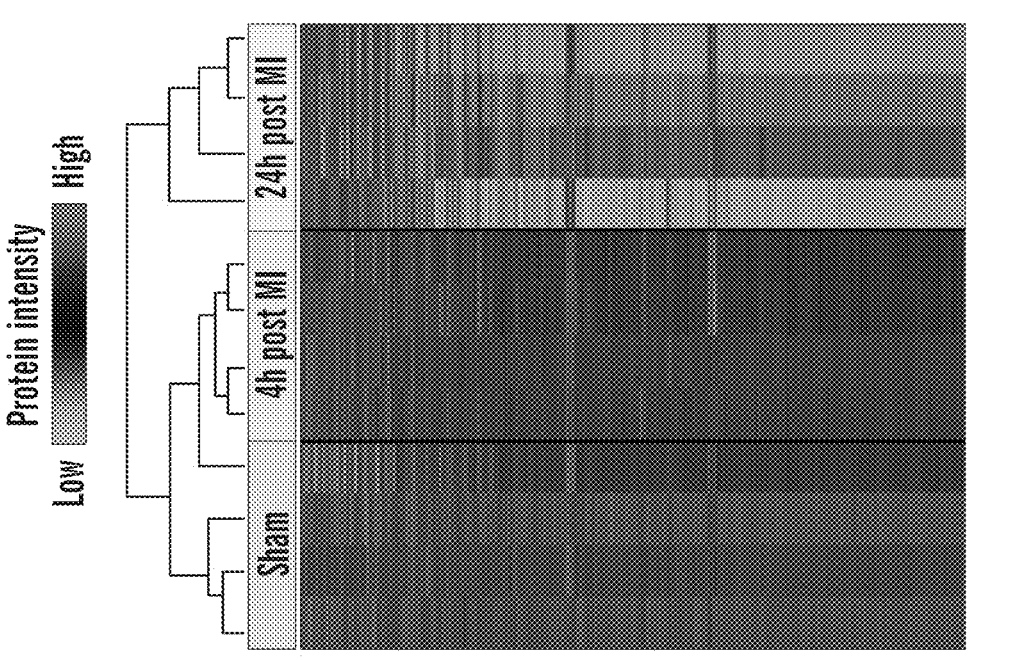
Figure 1B:
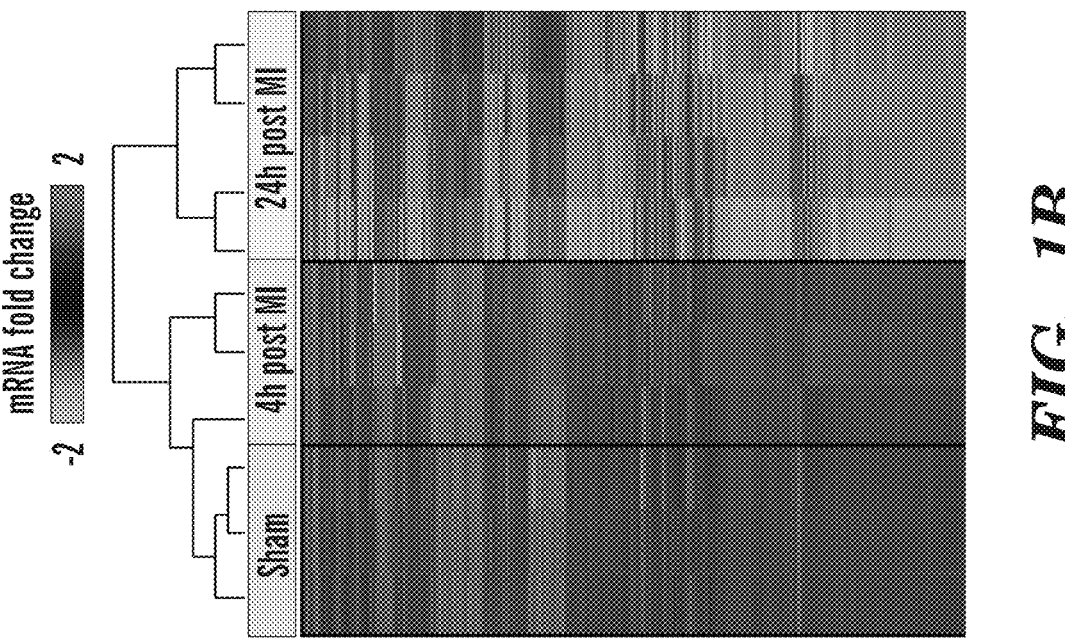

When comparing the two datasets, 2,272 genes were found with corresponding proteins. Out of all genes with corresponding proteins, 239 genes and 120 proteins were differentially expressed (q value<0.05) 4-hours post-MI. 24-hours post-MI, 1,702 genes and 272 proteins were differentially expressed. A hierarchical clustering dendrogram of gene expression (FIG. 1B, FIG. 2A) and protein levels (FIG. 1C) shows that in both cases the experimental groups cluster together, demonstrating significant differences in the transcriptome and proteome post-MI.

Figure 1E:
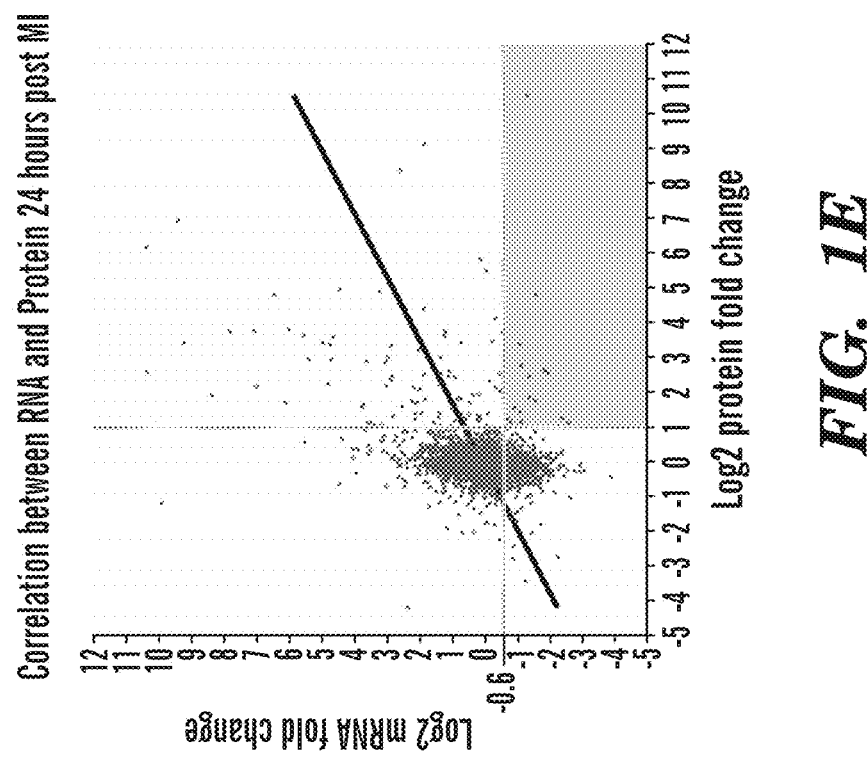
Figure 1D:
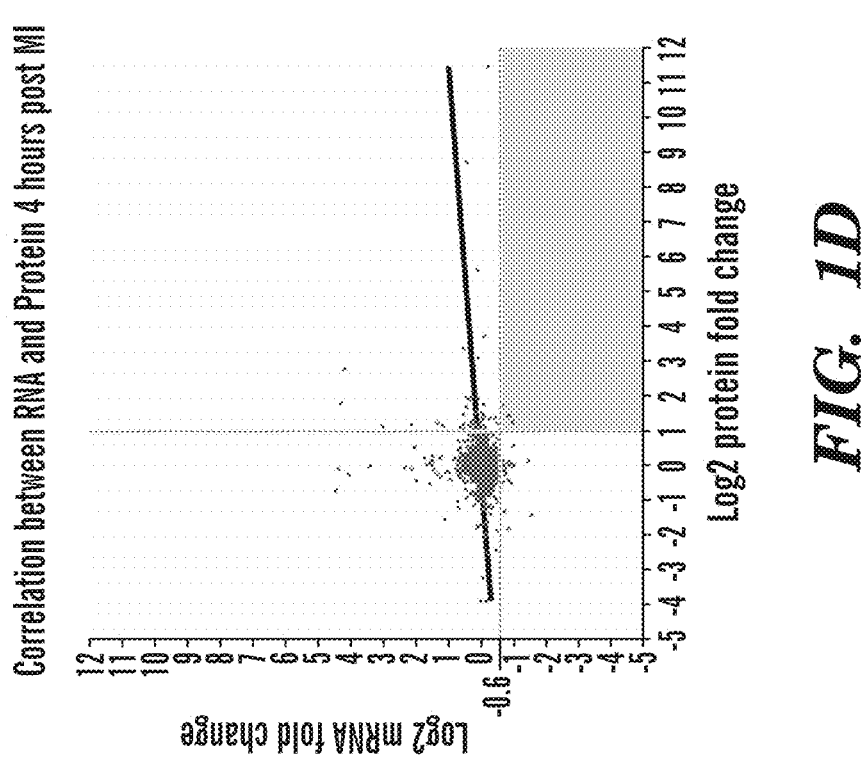

Pearson correlation analysis revealed a positive correlation between changes in gene expression and protein expression both 4-hours post-MI (r square=0.02, FIG. 1D) and 24-hours post-MI (r square=0.13, FIG. 1E). Significant correlation was found between the changes in gene expression and protein levels in the ischemic heart post-MI and in searching for a 5' UTR element that may elevate modRNA translation in the heart post-MI.

Example 2—Identification of 5' UTR Elements that Increase Translation of modRNA in the Heart Post-Myocardial Infarction (MI)

Figure 2D:
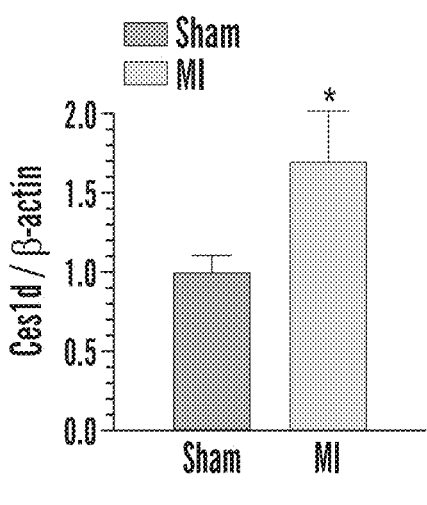

To identify genes with a significant non-correlation relationship between mRNA and protein expression, a screen for (i) genes that encode proteins with elevated levels 4-hours or 24-hours post-MI (fold change>2), (ii) mRNA that is down-regulated at 4-hours or 24-hours post-MI (fold change<0.64), and (iii) a 5' UTR shorter than 100 bp was carried out. 3 and 18 genes, each of which displayed high protein expression accompanied by lower or unchanged mRNA level as compared to sham-operated hearts, were identified at 4-hours (FIG. 1F) and 24-hours (FIG. 1G) post-MI, respectively. Five genes with the shortest 5' UTR among those 19 genes (as Fmd5 and Serpina 1b were present in both the 4-hour and 24-hour screen results) were identified (Gsn, Pzf, Serpina 1b, Fn3k, and Ces1d) (FIGS. 1F-1G; Table 4). The chosen genes had an upregulated protein expression that was unrelated to their mRNA expression, post-myocardial infarction. In addition, Ces1d expression results were validated using qPCR and western blot showing similar mRNA and protein expression as evaluated by RNAseq and proteomic analysis (FIGS. 2B-2D).

Figure 3A:
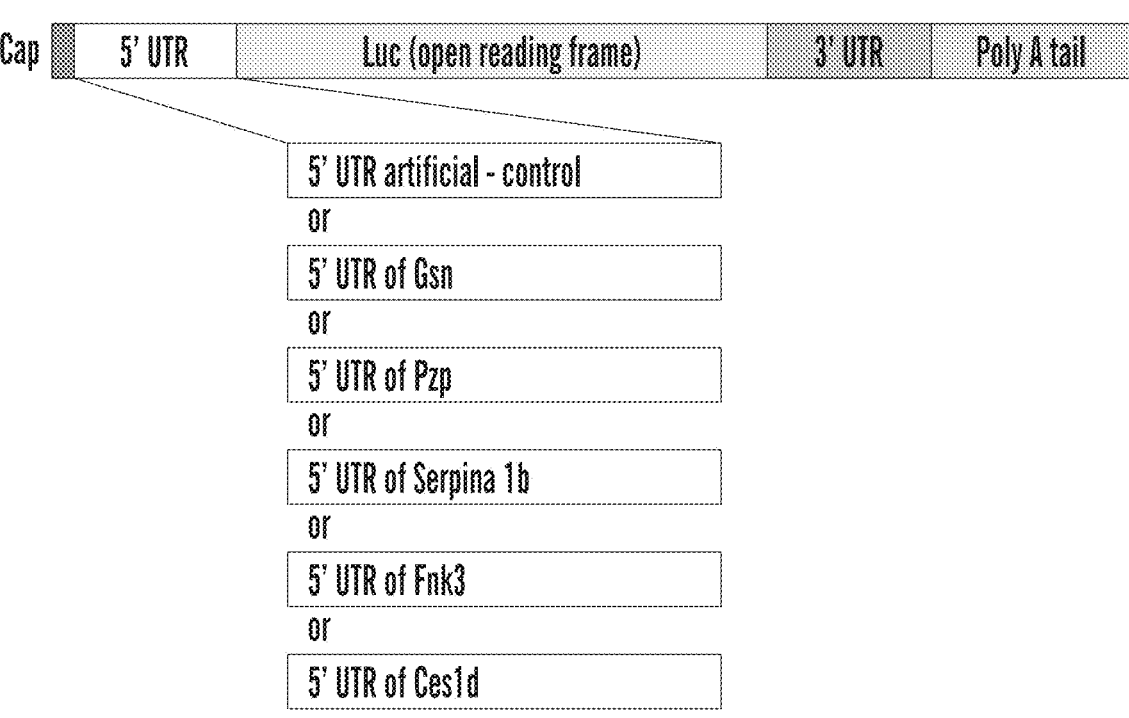
FIGS. 3A-3F show the translation efficiency of various synthetic modified mRNA (modRNA) constructs comprising 5' UTRs from genes identified in FIGS. 2A-2D.
Figure 3B:
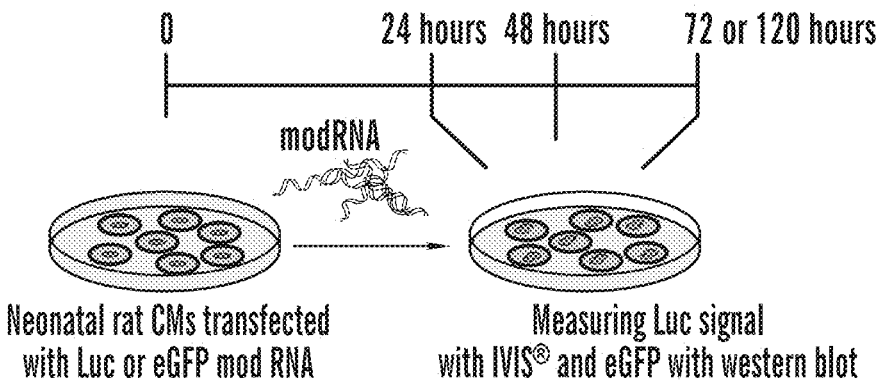
Figure 3C:
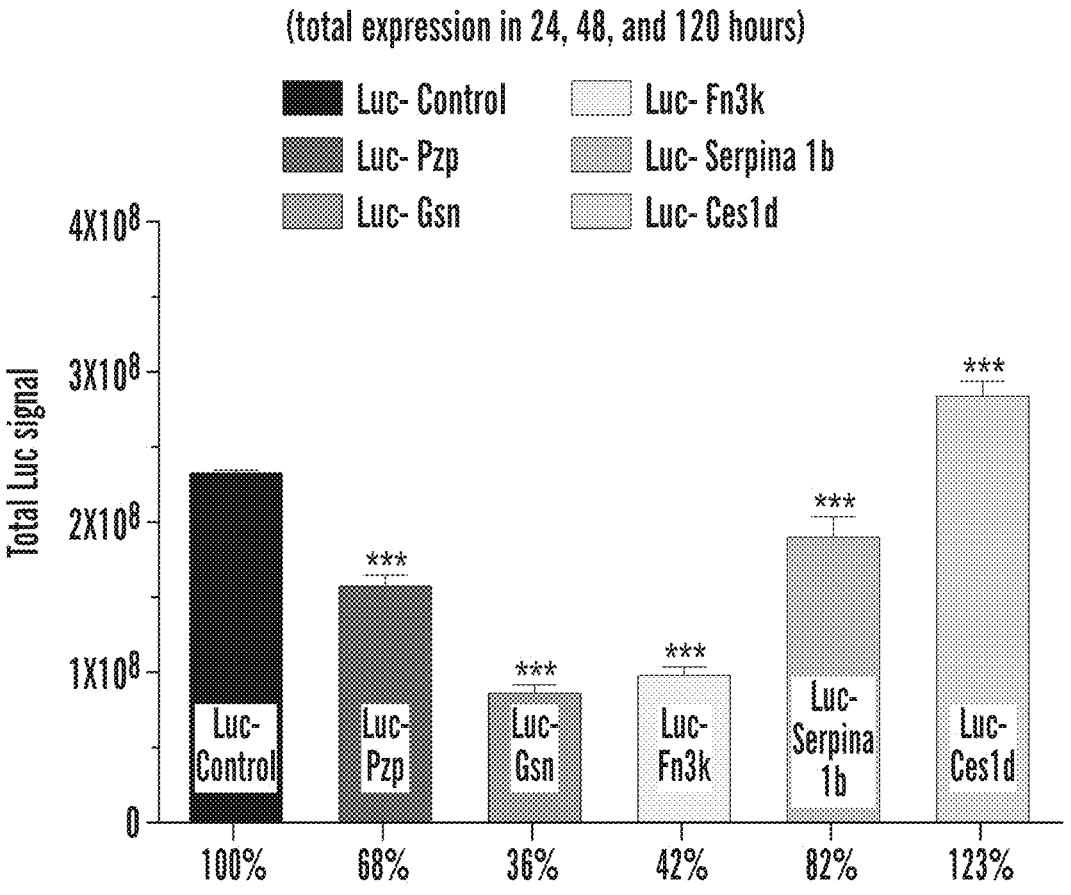

Example 3—The 5' UTR of Ces1d Increases In Vitro Expression of modRNA in Cardiomyocytes To evaluate the translational efficiency of the 5' UTR of genes identified in Table 4, five Luc modRNA constructs, each carrying the 5' UTR from one of the selected genes (i.e., Gsn, Pzf, Serpina 1b, Fn3k, and Ces1d), were designed and generated (FIG. 3A). A control Luc modRNA construct (Luc-Control) that carries an artificial 36 nucleotide 5' UTR commonly used for in vitro modRNA production was also generated (see, e.g., Warren et al., "Highly Efficient Reprogramming to Pluripotency and Directed Differentiation of Human Cells with Synthetic Modified mRNA," *Cell Stem Cell* 7:618-630 (2010), which is hereby incorporated by reference in its entirety). In vitro screening showed that all Luc modRNA constructs tested allowed modRNA protein translation in neonatal rat cardiomyocytes (FIGS. 3B-3C). However, Luc modRNA constructs comprising the 5' UTR from Gsn, Pzf, Serpina 1b, or Fn3k demonstrated significantly lower translational efficiency when compared to the Luc-Control modRNA construct (FIG. 3C). Interestingly, the Luc modRNA construct comprising the 5' UTR of Ces1d (Luc-Ces1d) showed a 23% increase in modRNA translation, as compared to the Luc-Control modRNA construct (FIG. 3C, FIGS. 4A-4B).

Figure 3F:
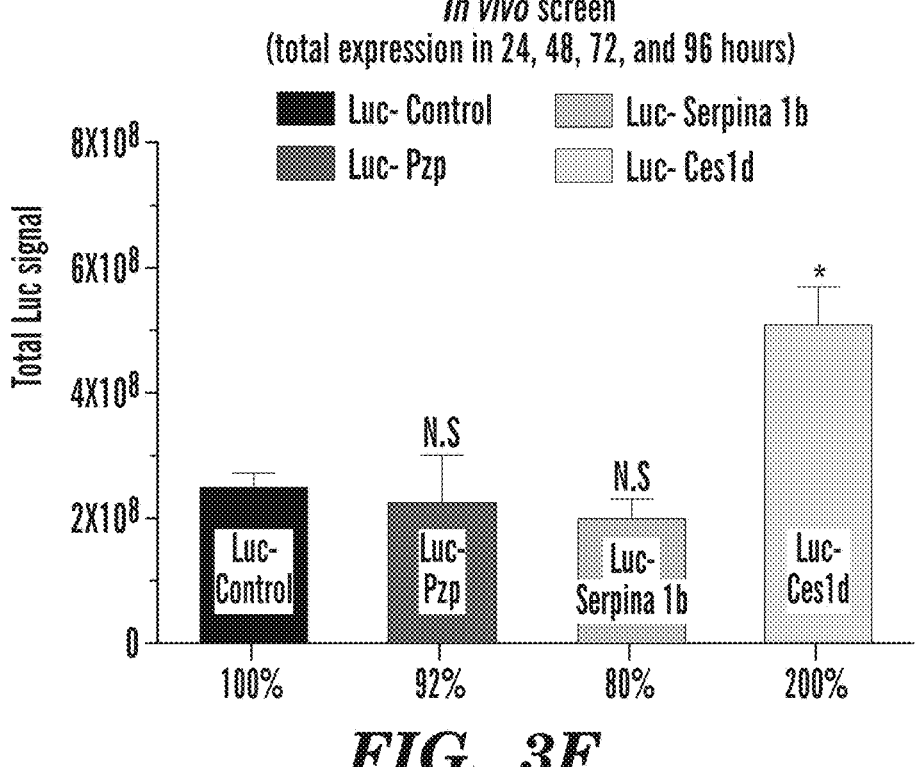
Figure 4D:
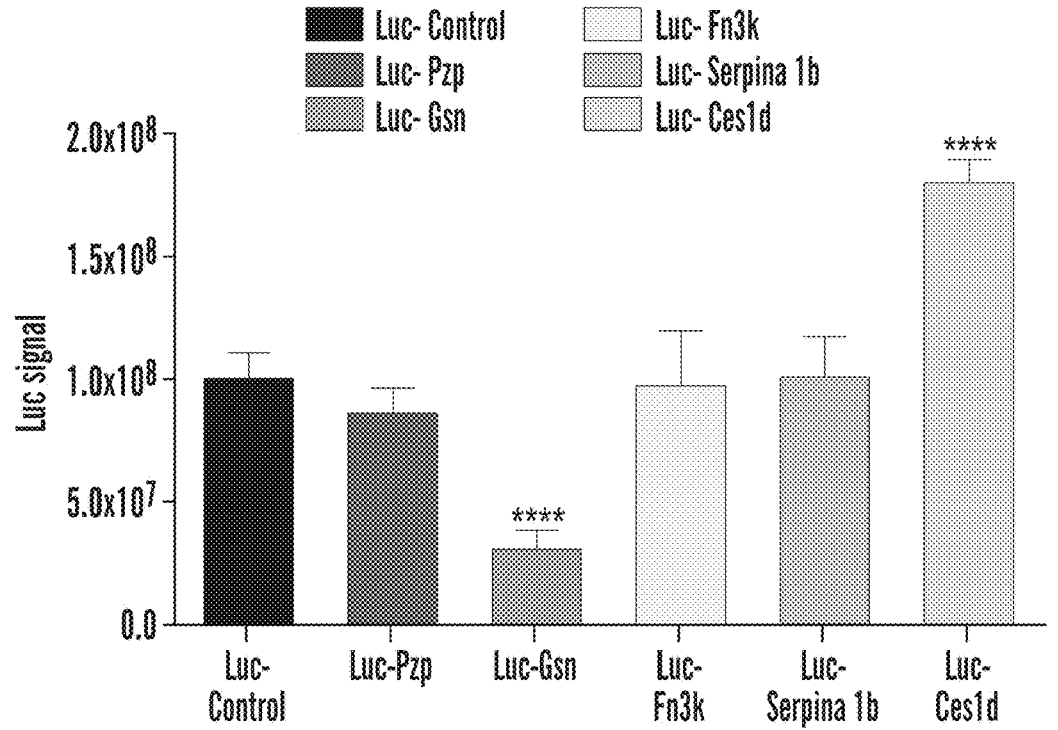
Figure 4E:
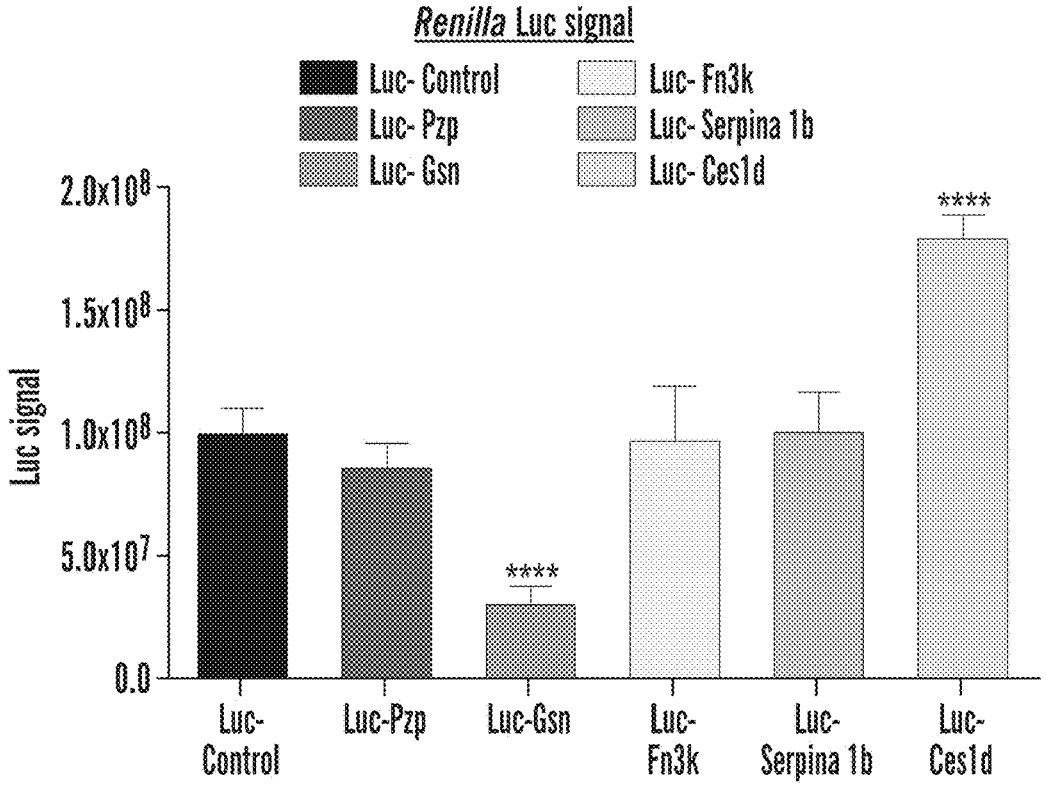
Figure 5A:
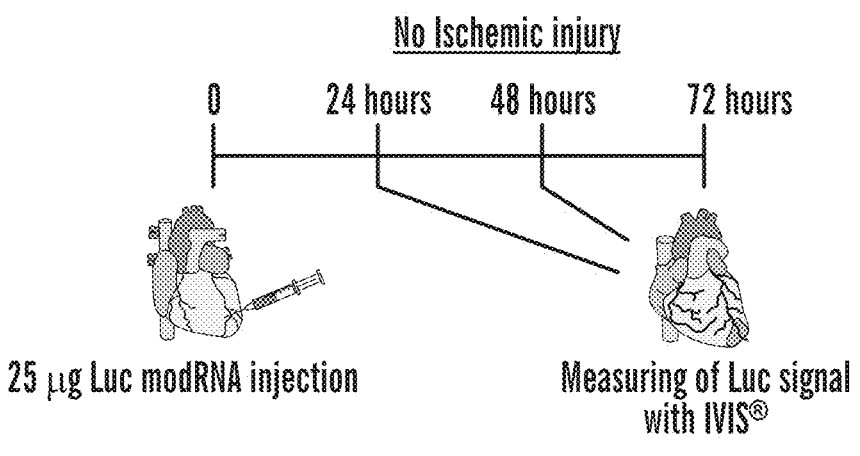
FIGS. 5A-5D demonstrate that the 5' UTR of Ces1d significantly enhances mRNA translation in ischemic hearts but not in a non-ischemic mouse model.
Figure 5B:
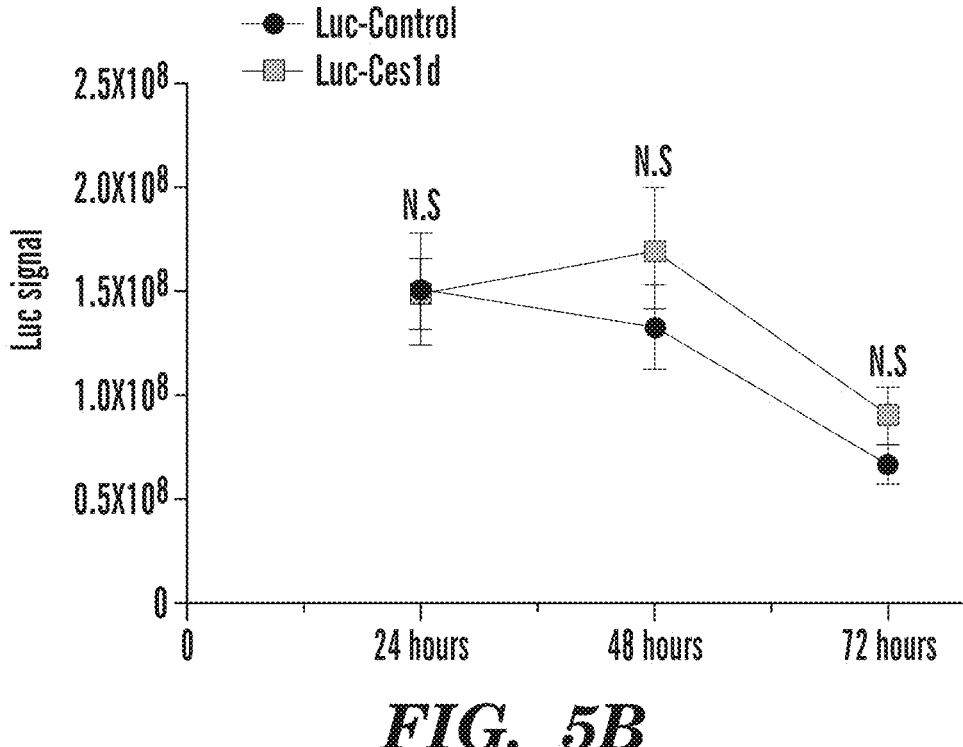
Figure 5C:
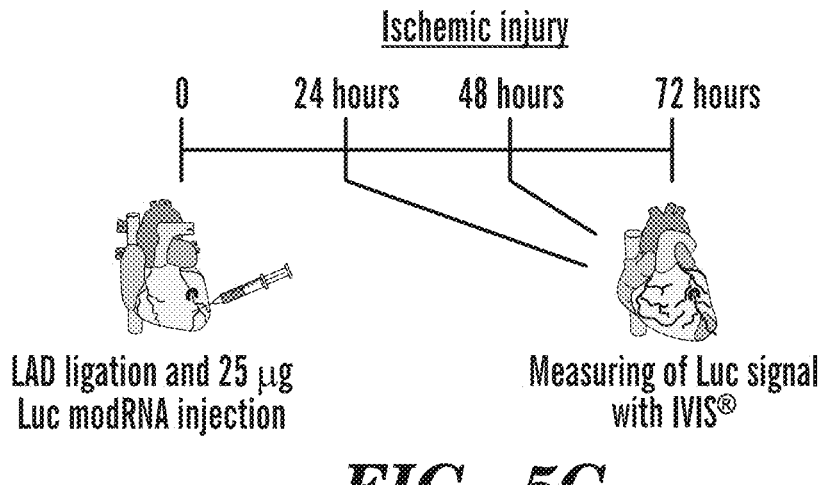
Figure 5D:
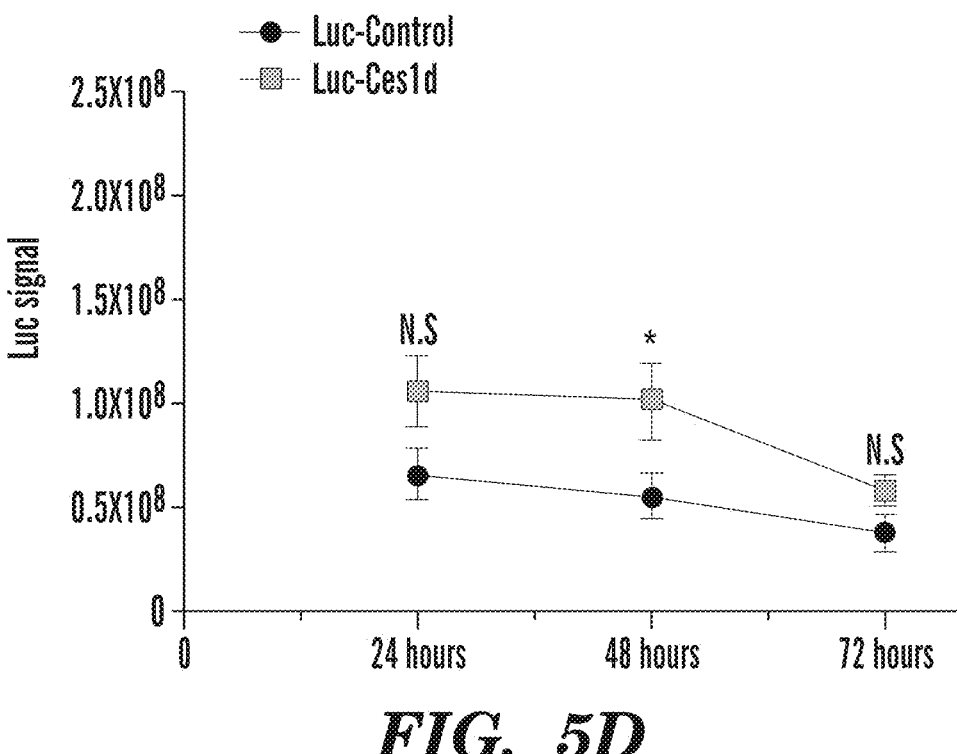

To confirm that the increase in modRNA translation using the Luc-Ces1d construct was not due to differential transfection efficiencies, a parallel in vitro experiment was carried out with co-transfection of Firefly Luc 5' UTR modRNA constructs and a *Renilla* Luc modRNA construct comprising a control 5' UTR (as an internal control) in neonatal rat cardiomyocytes (*Renilla* Luc-Control) (FIG. 4A). 24 hours post-transfection, the IVIS® system was used to measure simultaneously the translation of the two different luciferase (firefly and *Renilla*) modRNA, in vitro (FIG. 4B). Similar to the results shown in FIG. 3F, the Luc-Ces1d modRNA construct produced a significantly higher firefly Luc signal (which is indicative of a significantly higher translation efficiency) as compared to the Luc-Control modRNA construct, without a corresponding significant change in the *Renilla* Luc signal produced using the *Renilla* Luc-Control modRNA construct (FIGS. 4B-4C). These results indicate that the high translation efficiency of the

TABLE 4

5' UTR Sequence of Selected Genes from
FIG. 1F and FIG. 1G.

| Gene Name | 5' UTR Sequence[†] | SEQ ID NO. |
|---|---|---|
| Ces1d | AGGAGGCGGGTCCCCTGGTCCACAACAGAAGCATTGCTAAAGC AGCAGATAGCTCAGAGACCACAGAGCCCTTGTCCTTCCACA | 1 |
| Gsn | GCTAGGGCGGGATGGGACGGCCGGTTACTTAAAGGTTGGGGCG ACCAAGGGTCCGCGGCCGCAGCCTGGGTCCTCACCGTCGCC | 54 |
| Pzp | CAAGGATCAGAGTTCGGGGGCTGAGGGCTCAGACGTTCTTCTC TGCCCTCTCCACC | 55 |
| Serpina 1b | ATATCCCCCTTGGCTCCCACTGCTTAAATACAGACTAGGAGAG GGCTCTGTCTCCTCAGCCTCGGTCACCACCCAGCTCTGGGACA GCAAGCTGAAA | 56 |
| Fn3k | TGCGTCACCTGACCGCATTCTGCACCTCAACTCTCC | 57 |

[†]RNA Element D of the carboxylesterase 5' UTR sequence is shown in bold underline in the above Table 4.

modRNA constructs is due to the use of the Ces1d 5' UTR and not due to different transfection efficiency.

To further confirm this finding, eGFP modRNA constructs comprising the 5' UTR of Ces1d (eGFP-Ces1d) or the artificial 36 nucleotide 5' UTR described above (eGFP-Control) were generated. The eGFP translation levels of the eGFP-Ces1d and eGFP-Control constructs were evaluated by western blot in neonatal rat cardiomyocytes. Similar to the Luc modRNA results, eGFP-Ces1d showed a 22% increase in modRNA translation in comparison to eGFP-Control (FIG. 3D).

Figure 3D:
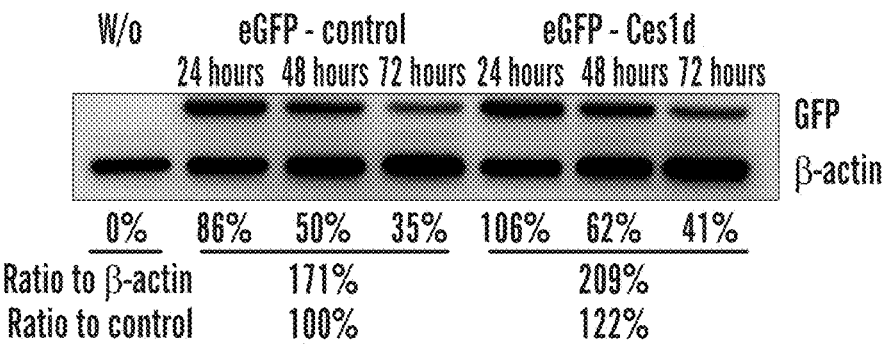
Figure 3E:
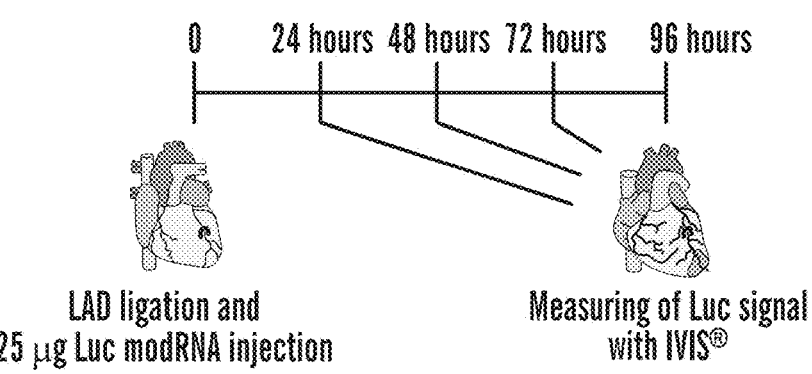

Example 4—The 5' UTR of Ces1d Increases In Vivo Expression of modRNA in Cardiomyocytes A mouse myocardial infarction model was used to further evaluate the translational efficiency of the three Luc modRNA constructs that showed the highest translation levels in vitro (Luc-Pzp, Luc-Serpina 1b, and Luc-Ces1d) (FIGS. 3B-3D). The in vivo translation efficiency of Luc-Pzp, Luc-Serpina 1b, Luc-Ces1d, and Luc-Control modRNA constructs was measured 24-hours, 48-hours, 72-hours, and 96-hours post-MI (FIG. 3E). FIG. 3F demonstrates that injection with Luc-Ces1d modRNA resulted in significantly (2-fold) higher luciferase signals, which indicate a significantly higher translation of the modRNA construct than either Luc-Control modRNA, Luc-Pzp modRNA, or Luc-Serpina 1b modRNA constructs.

Example 5—Pharmacokinetic Evaluation of Luc-Ces1d modRNA in Mouse Heart

Figures 6A, 6B:
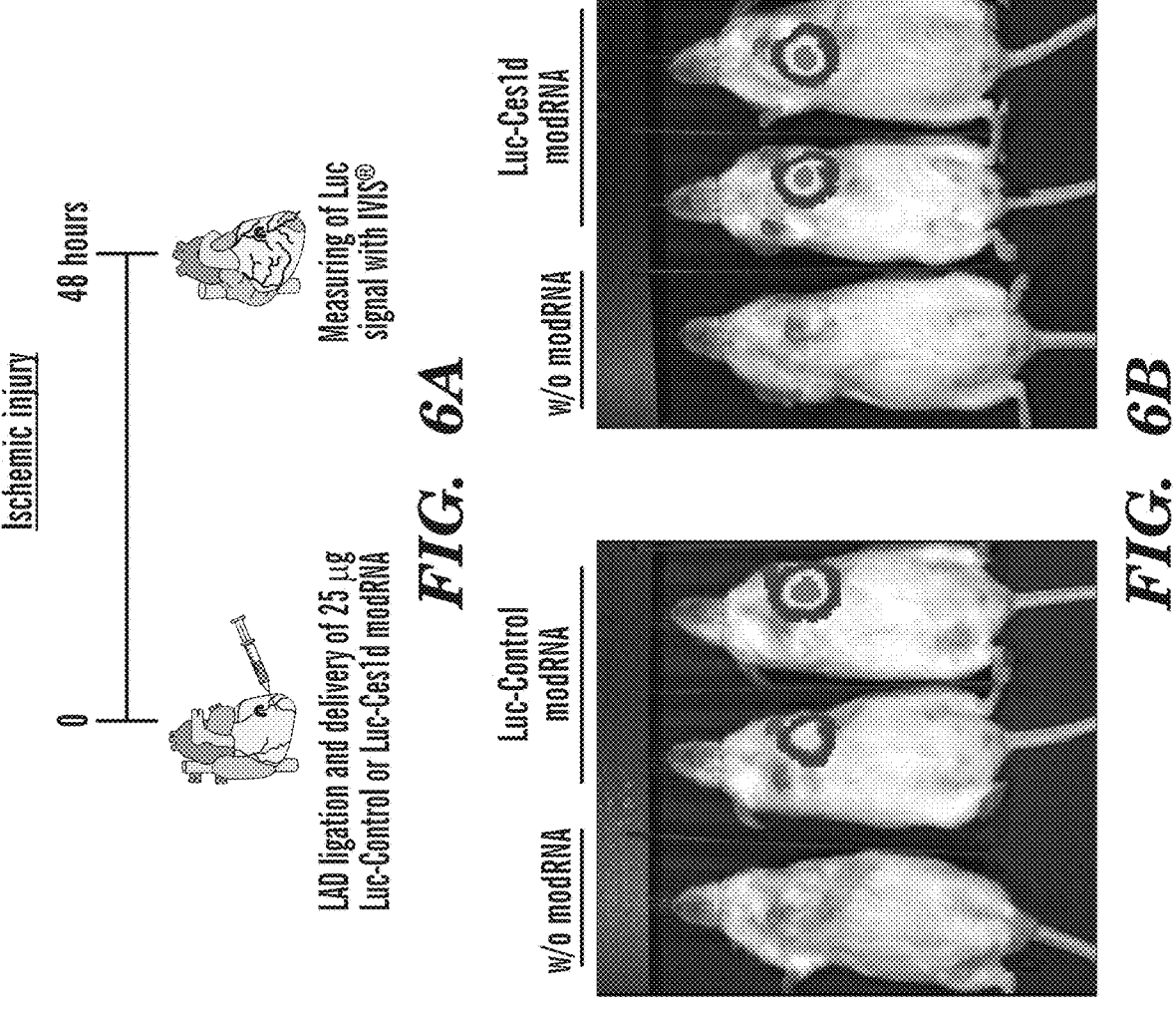

To determine whether the 5' UTR of Ces1d regulates protein translation in other contexts, Luc-Ces1d and Luc-Control modRNA-mediated translation was evaluated in non-ischemic (FIGS. 5A-5B) and ischemic heart mouse models (FIGS. 5C-5D, FIGS. 6A-6B). While there were no significant changes in Luc-Ces1d modRNA translation levels in comparison with Luc-Control modRNA in the heart without MI 24 hours, 48 hours, or 72 hours days post-injection (FIG. 5B), significantly more Luc-Ces1d translation was observed than Luc-Control translation 48 hours-days post-MI (FIG. 5D; FIG. 6B). These results suggest that the 5' UTR of Ces1d may enhance modRNA translation in the heart only under ischemic conditions, like MI.

Figure 7A:
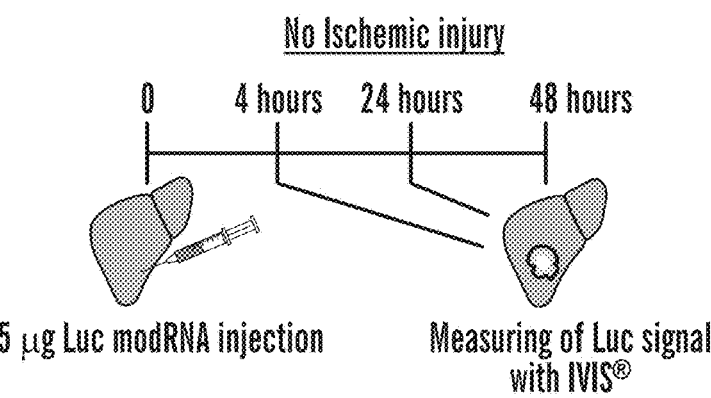
FIGS. 7A-7H demonstrate that the 5' UTR of Ces1d significantly enhances Luc modRNA translation in the liver, but not in non-ischemic or kidney ischemic mouse models.
Figure 7B:
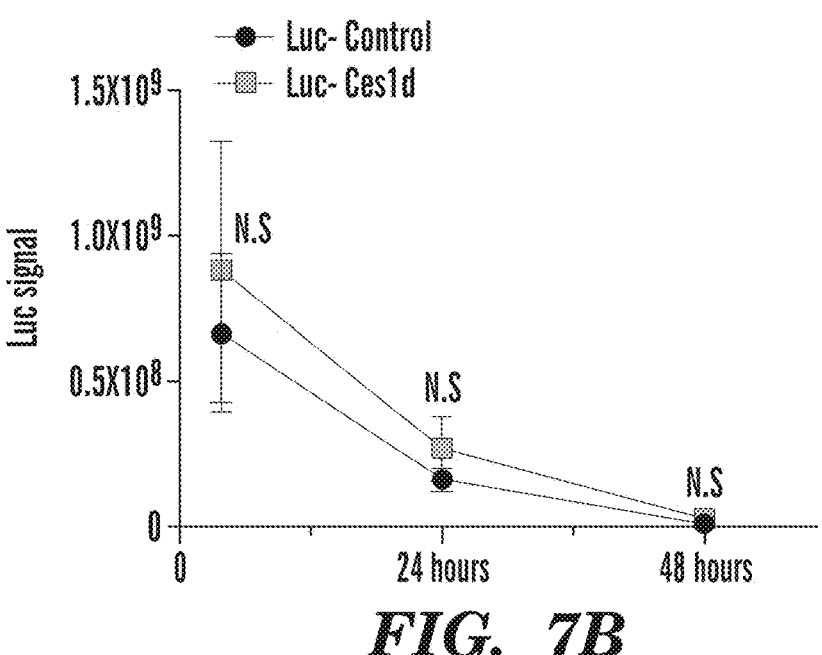
Figure 7C:
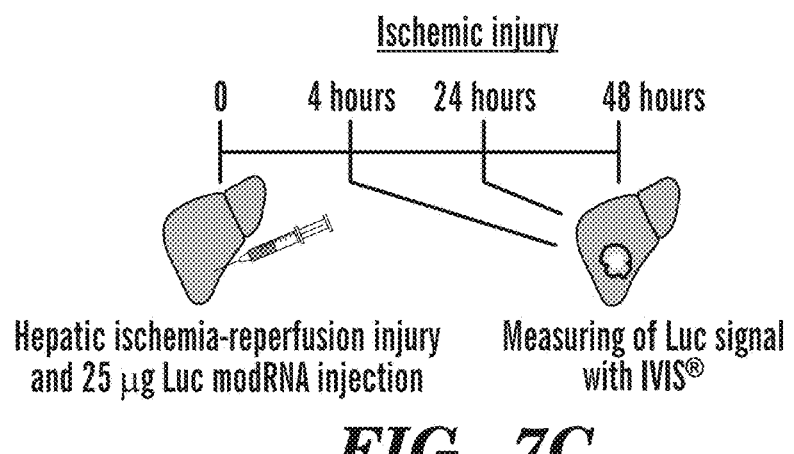
Figure 7D:
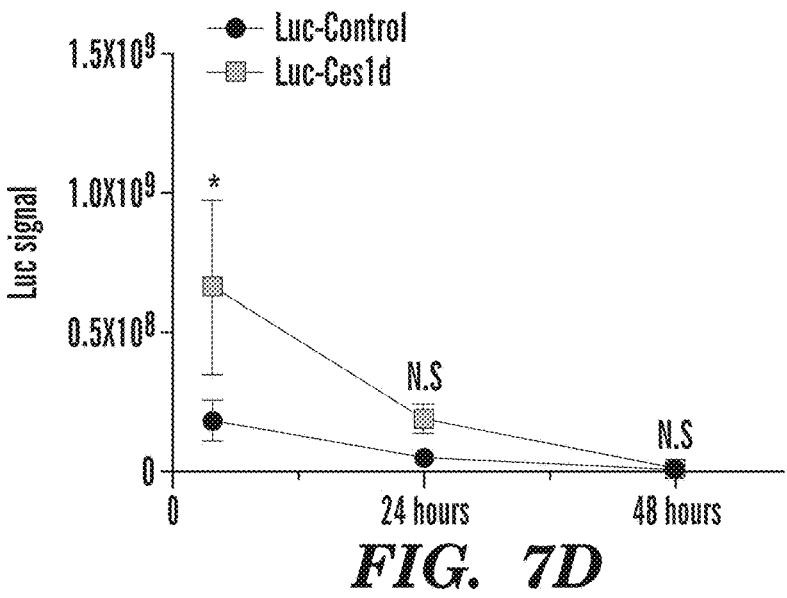
Figure 7E:
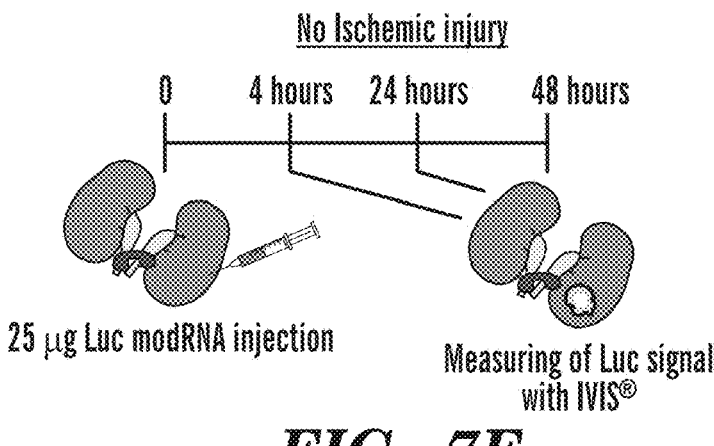
Figure 7F:
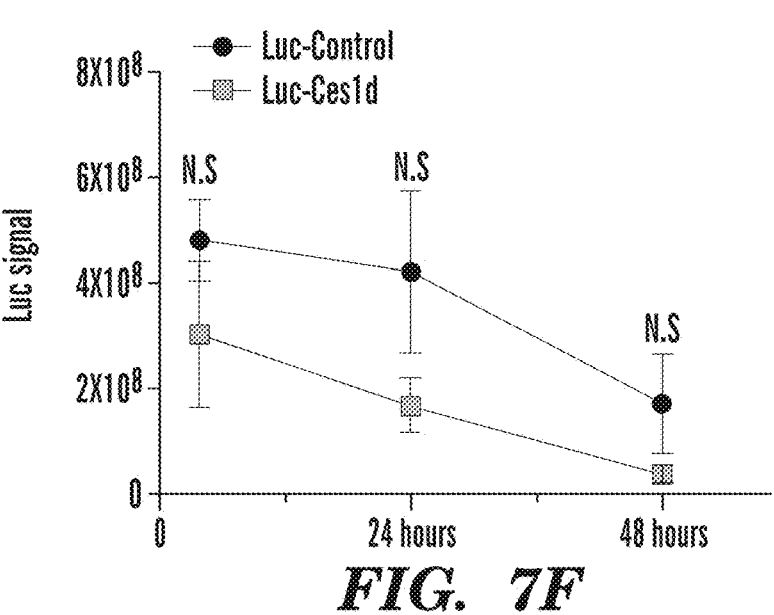
Figure 7G:
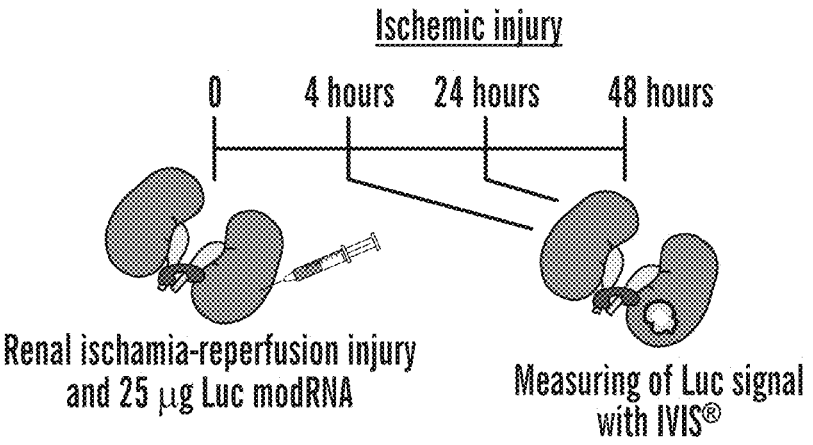
Figure 7H:
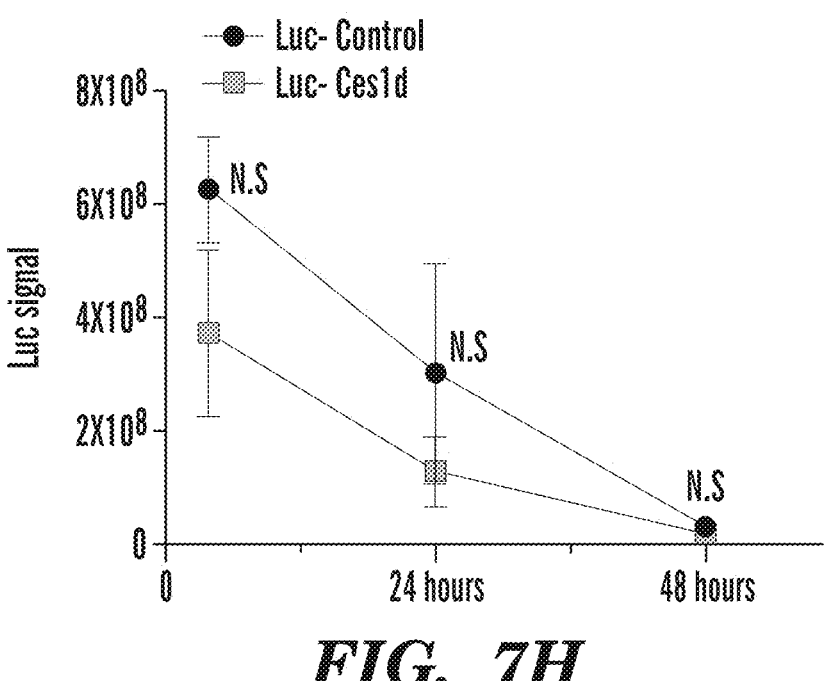

Example 6—Pharmacokinetic Evaluation of Luc-Ces1d modRNA in Mouse Liver and Kidney The role of the 5' UTR of Ces1d in modRNA translation under ischemic conditions in organs other than the heart was next evaluated. Since acute hepatic or renal ischemia may lead to hepatic or renal failure, which may be fatal, liver and kidney were chosen as representative organs for ischemic disease. Similar to the heart, ischemic injury in the liver significantly increased Luc-Ces1d modRNA expression (4-hours post-delivery) in comparison to Luc-Control modRNA expression (FIGS. 6C-6D, FIGS. 7A-7D). Similar to heart, no significant differences were seen between groups in the liver without ischemic injury (FIGS. 7A-7B). Yet, Luc-Ces1d modRNA had no significant translational differences in comparison to Luc-Control in ischemic and non-ischemic conditions in the kidney (FIGS. 6E-6F, FIGS. 7E-7H).

Figure 8B:
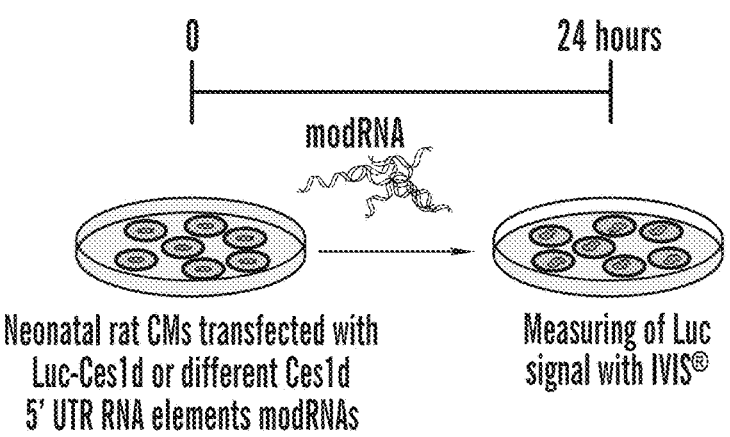
Figure 8C:
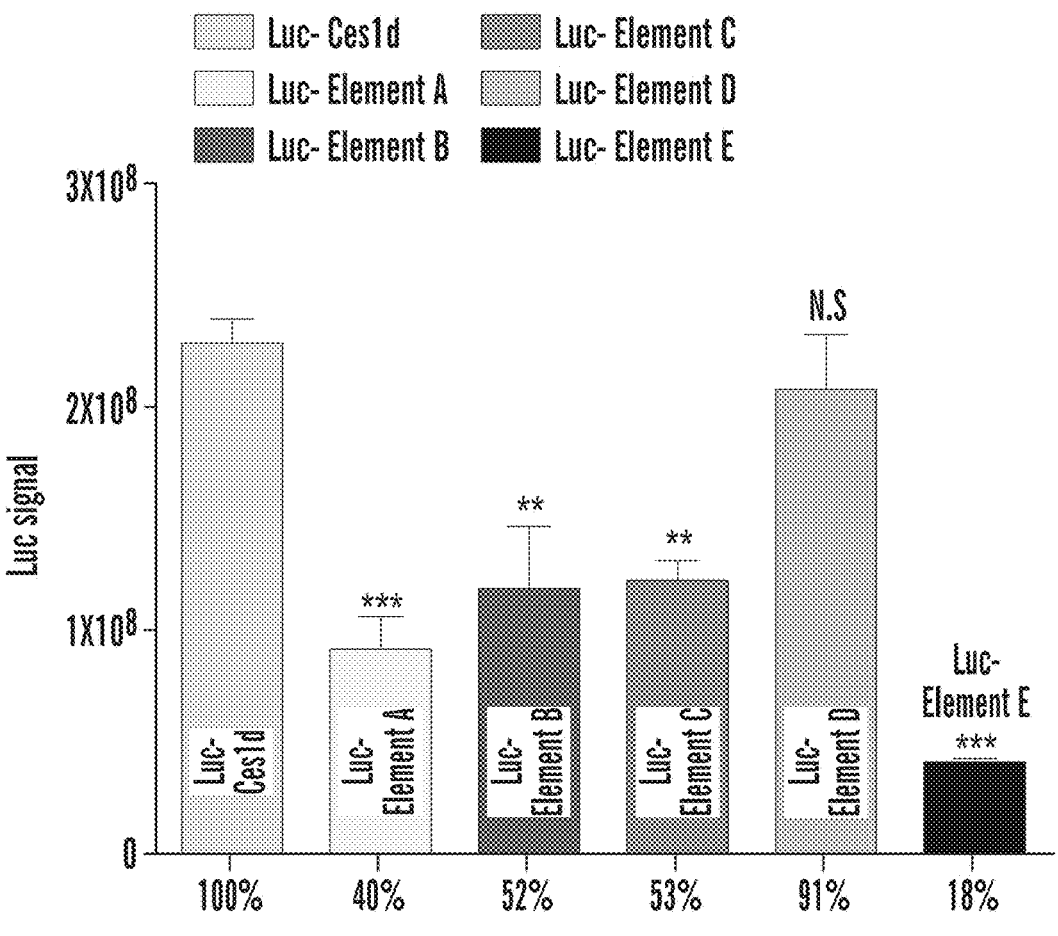

Example 7—RNA Element D Increases modRNA Translation Post-Myocardial Infarction To identify the RNA element in the 5' UTR of Ces1d responsible for the significantly enhanced translation of modRNA carrying the 5' UTR of Ces1d, consensus elements conserved among different species (e.g., mouse, rat, pig, gerbil, and human) were examined. Interestingly, four out of the five elements identified (Elements B-E) were conserved among species (FIG. 8A). Based on this information, five Luc modRNA constructs, each carrying a different RNA element of Ces1d as its 5' UTR, were generated (i.e., Luc-Element A, Luc-Element B, Luc-Element C, Luc-Element D, and Luc-Element E modRNA constructs). The translation abilities of each of those constructs was evaluated in neonatal rat cardiomyocytes in comparison to Luc-Ces1d modRNA (FIGS. 8B-8C). Significantly reduced translation ability was observed for Luc-Element A, Luc-Element B, Luc-Element C, and Luc-Element E modRNA constructs, but not for the Luc-Element D modRNA construct (FIG. 8C). It was thus hypothesized that element D is the RNA element responsible for the higher translation ability of Luc-Ces1d.

Figure 8D:
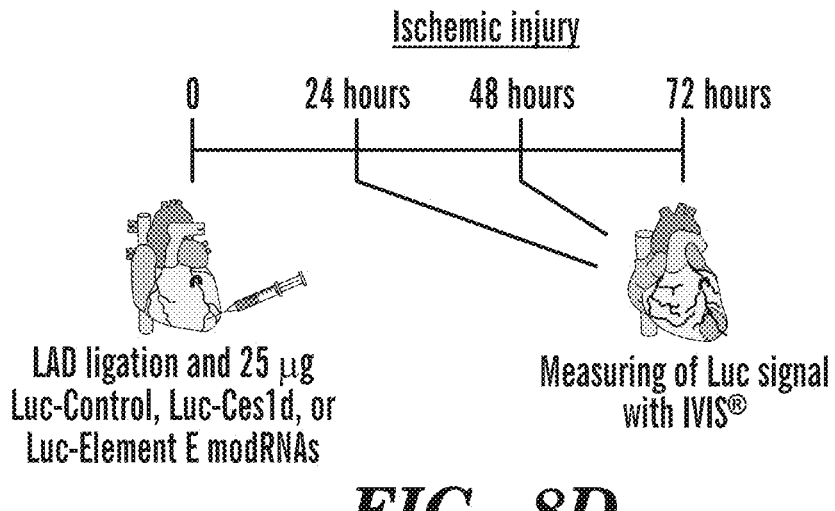
Figure 8E:
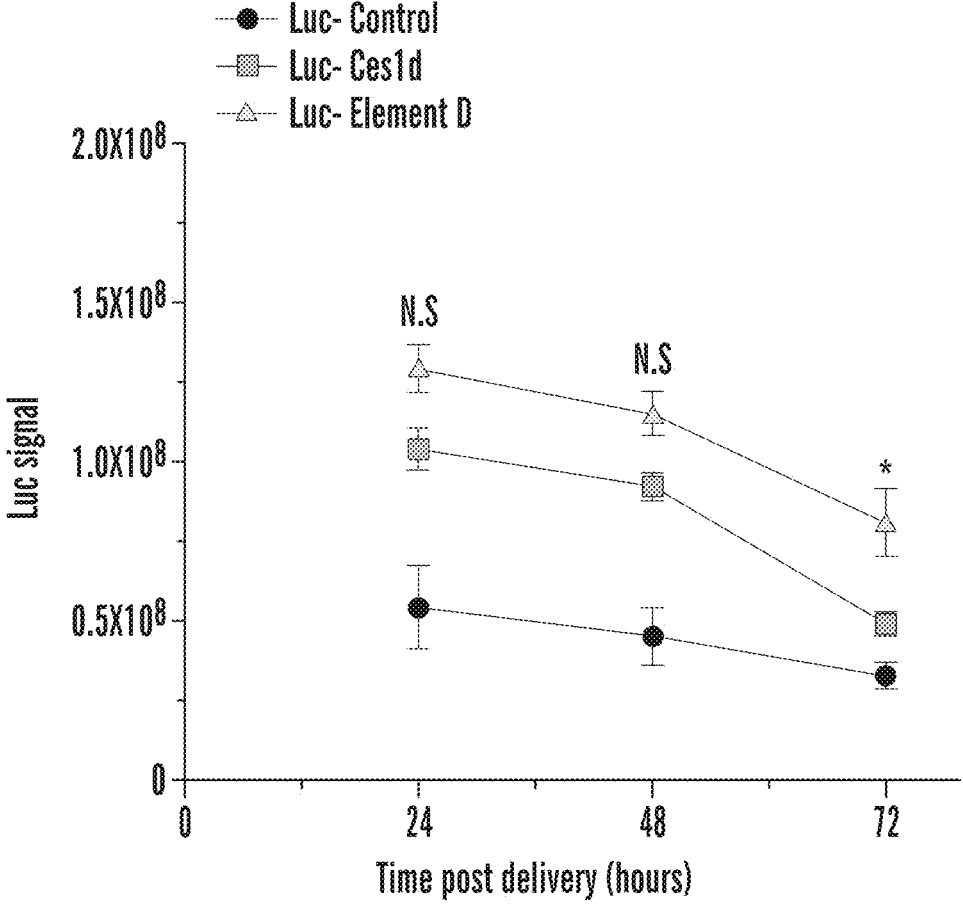
Figure 9A:
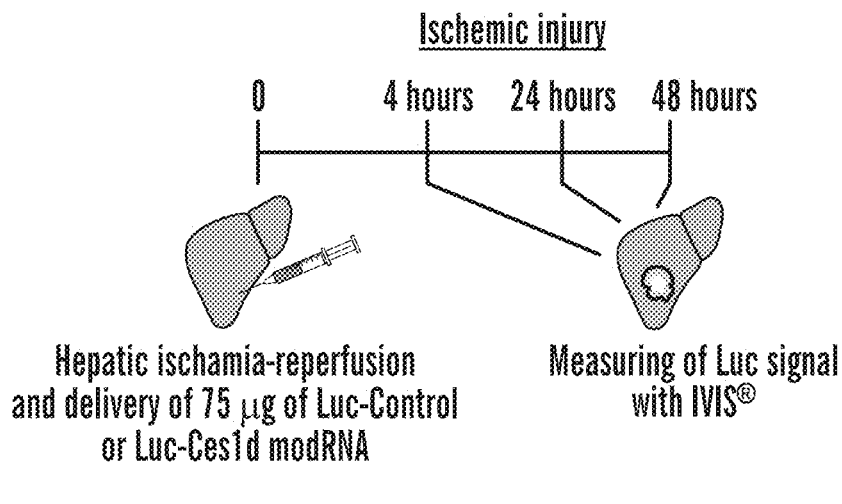
FIGS. 9A-9B demonstrate that Element D of the 5' UTR of Ces1d does not increase mRNA translation significantly more than the full-length 5' UTR of Ces1d in a liver ischemic mouse model.
Figure 9B:
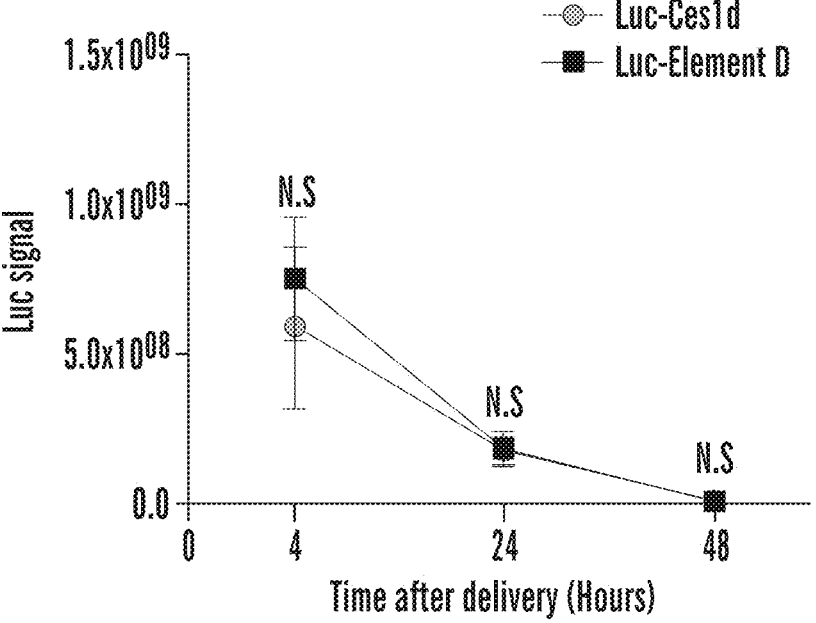
Figure 10B:
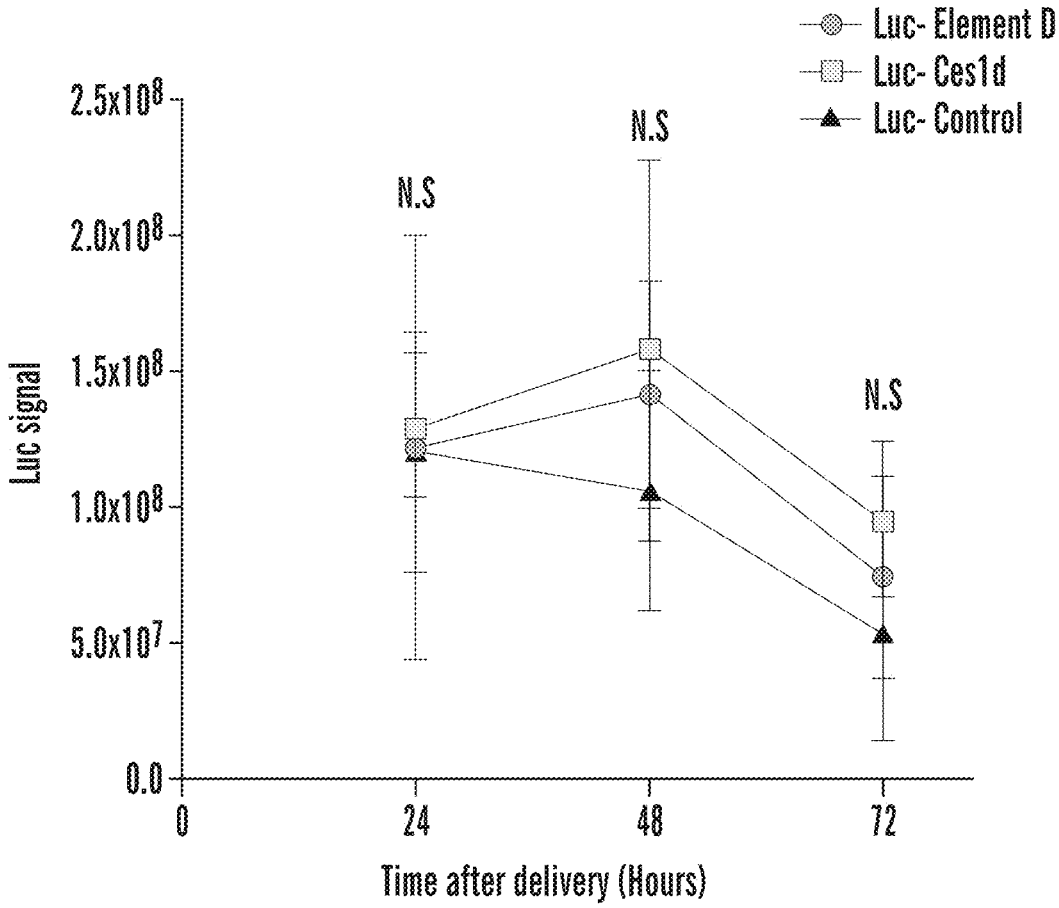

To confirm that Element D is the RNA element responsible for the higher translation ability of Luc-Ces1d modRNA, the expression of Luc-Ces1d and Luc-Element D was compared to the expression of Luc-Control in an ischemic heart model over three days (FIG. 8D). FIG. 8E demonstrates that Luc modRNA constructs comprising the 5' UTR of Ces1d or Element D of Ces1d have increased translation compared to Luc-Control modRNA. Surprisingly, Element D of Ces1d alone has a significantly higher translation rate in the heart at 3 days post-MI (FIG. 8E). Overall, combining the three day readouts, Luc-Element D translation in the heart post-MI was 2.5-fold higher than the widely used artificial 5' UTR, Luc-Control. However, Luc-Element D failed to increase translation more than Luc-Ces1d in liver ischemic injury (FIGS. 9A-9B) and over Ces1d-Luc or Luc-Control in heart non-ischemic injury (FIGS. 10A-10B).

Discussion of Examples 1-7

The use of modRNA as a gene delivery tool is growing in the field of therapeutic medicine. The results presented herein suggest that modRNA may be employed to induce cardiac protection, cardiovascular regeneration, and cardiovascular regeneration post-ischemic injury (Hadas et al., "Modified mRNA as a Therapeutic Tool to Induce Cardiac Regeneration in Ischemic Heart Disease," *Wiley Interdiscip. Rev. Syst. Biol. Med.* 9 (2017), which is hereby incorporated by reference in its entirety). The immediate delivery of VEGF-A modRNA in a MI mouse model has been shown to lead to the induction of cardiovascular regeneration (Zangi et al., "Modified mRNA Directs the Fate of Heart Progenitor Cells and Induces Vascular Regeneration after Myocardial Infarction," *Nat. Biotechnol.* 31:898-907 (2013), which is hereby incorporated by reference in its entirety). A follow-up large animal study showed a significant improvement of cardiac function when VEGF-A modRNA was delivered one week post-MI (Carlsson et al., "Biocompatible, Purified VEGF-A mRNA Improves Cardiac Function after Intracardiac Injection 1 Week Post-myocardial Infarction in Swine," *Mol. Ther. Methods Clin. Dev.* 9:330-346 (2018), which is hereby incorporated by reference in its entirety). Recently, intradermal VEGF-A modRNA delivery in patients suffering from type 2 diabetes was shown to be safe and to possibly promote angiogenesis (Gan et al., "Intradermal Delivery of Modified mRNA Encoding VEGF-A in Patients with Type 2 Diabetes," *Nat. Commun.* 10:871 (2019), which is hereby incorporated by reference in its entirety).

VEGF-A modRNA is now being evaluated in Phase 2a human clinical trials to improve cardiac function in patients with heart failure. In parallel, other groups are using modRNA to deliver different target genes in preclinical studies of different liver diseases, including models for factor IX deficiency hemophilia B (DeRosa et al., "Therapeutic Efficacy in a Hemophilia B Model Using a Biosynthetic mRNA Liver Depot System," *Gene Ther.* 23:699-707 (2016), which is hereby incorporated by reference in its entirety); acute intermittent porphyria (Jiang et al., "Systemic Messenger RNA as an Etiological Treatment for Acute Intermittent Porphyria," *Nat. Med.* 24:1899-1909 (2018), which is hereby incorporated by reference in its entirety); glycogen storage disease type 1A (Roseman et al., "G6PC mRNA Therapy Positively Regulates Fasting Blood Glucose and Decreases Liver Abnormalities in a Mouse Model of Glycogen Storage Disease 1a," *Mol. Ther.* 26:814-821 (2018), which is hereby incorporated by reference in its entirety); thrombotic thrombocytopenic purpura (Liu-Chen et al., "mRNA Treatment Produces Sustained Expression of Enzymatically Active Human ADAMTS13 in Mice," *Sci. Rep.* 8:7859 (2018), which is hereby incorporated by reference in its entirety); alpha-1 antitrypsin deficiency (Connolly et al., "SERPINA1 mRNA as a Treatment for Alpha-1 Antitrypsin Deficiency," *J. Nucleic Acids* 2018:8247935 (2018), which is hereby incorporated by reference in its entirety); Crigler-Najjar syndrome type 1 (Apgar et al., "Quantitative Systems Pharmacology Model of hUGT1A1-modRNA Encoding for the UGT1A1 Enzyme to Treat Crigler-Najjar Syndrome Type 1," *CPT Pharmacometrics Syst. Pharmacol.* 7:404-412 (2018), which is hereby incorporated by reference in its entirety); and urea cycle disorders (Prieve et al., "Targeted mRNA Therapy for Ornithine Transcarbamylase Deficiency," *Mol. Ther.* 26:801-813 (2018), which is hereby incorporated by reference in its entirety) with target genes of FIX, PBGD, glucose-6-phosphatase, ADAMTS13, SERPINA1, bilirubin-UGT, ornithine, and transcarbamoylase, respectively.

As described above, both heart and liver diseases have been heavily studied in the search for new treatments using modRNA. One obstacle in moving to large animal and clinical trials that is related to modRNA is the need for large amounts of modRNA to transfect human or large animal hearts and livers. In addition, due to the short expression of modRNA, it might need to be administered several times. To reduce the need to administer large amounts and/or multiple doses of therapeutic modRNA, it is desirable to improve modRNA translation such that therapeutically effective amounts of protein may be effectively translated from relatively low amounts of modRNA.

Several elements within RNA are responsible for regulating translation including, e.g., nucleotide type, poly A tail length, 5' UTR, 3' UTR, and cap analog structures. The results presented herein demonstrate that replacing pseudouridine with 1-M-pseudouridine in modRNA results in higher modRNA translation in the heart when 1-M-pseudouridine is being used (Sultana et al., "Optimizing Cardiac Delivery of Modified mRNA," *Mol. Ther.* 25(6):1306-1315 (2017), which is hereby incorporated by reference in its entirety). In addition, it was found that a longer poly-A tail can increase modRNA translation in vivo. Examples 1-7 herein describe a novel screening method that compares proteomic and transcriptomic analysis to identify 5' UTR sequences that can increase modRNA translation in ischemia more effectively than the widely used artificial 5' UTR that has been used in previous modRNA publications (Sultana et al., "Optimizing Cardiac Delivery of Modified mRNA," *Mol.*

*Ther.* 25(6):1306-1315 (2017); Hadas et al., "Optimizing Modified mRNA In Vitro Synthesis Protocol for Heart Gene Therapy," *Mol. Ther. Methods Clin. Dev.* 14(13):300-305 (2019); Zangi et al., "Modified mRNA Directs the Fate of Heart Progenitor Cells and Induces Vascular Regeneration after Myocardial Infarction," *Nat. Biotechnol.* 31:898-907 (2013), Kormann et al., "Expression of Therapeutic Proteins after Delivery of Chemically Modified mRNA in Mice," *Nat. Biotechnol.* 29:154-157 (2011); Kormann et al., "Expression of Therapeutic Proteins After Delivery of Chemically Modified mRNA in Mice," *Nat. Biotechnol.* 29:154-157 (2011); Carlsson et al., "Biocompatible, Purified VEGF-A mRNA Improves Cardiac Function after Intracardiac Injection 1 Week Post-myocardial Infarction in Swine," *Mol. Ther. Methods Clin. Dev.* 9: 330-346 (2018); and Gan et al., "Intradermal Delivery of Modified mRNA Encoding VEGF-A in Patients with Type 2 Diabetes," *Nat. Commun.* 10:871 (2019), which are hereby incorporated by reference in their entirety).

The results presented herein show a positive correlation at both 4-hours and 24-hours post-MI in mRNA levels and protein intensity in the ischemic heart. 19 negatively correlating genes, in which mRNA levels were either reduced or unchanged while their protein levels were upregulated at 4-hours and 24-hours post-MI, were also identified. The average 5' UTR length is ~100 to ~220 nucleotides across species (Pesole et al., "Structural and Functional Features of Eukaryotic mRNA Untranslated Regions," *Gene* 276:73-81 (2001), which is hereby incorporated by reference in its entirety). In vertebrates, longer 5' UTRs tend to be associated with poor translation (Davuluri et al., "CART Classification of Human 5' UTR sequences," *Genome Res.* 10:1807-1816 (2000), which is hereby incorporated by reference in its entirety). Therefore, five genes with the shortest 5' UTRs were selected for evaluation (<100 base pairs) (FIGS. 1A-1G).

Negative correlation between mRNA levels and protein expression has been reported, especially when internal or external stimuli trigger alteration in translation of specific genes. VEGF-A has been shown to be a stress-induced protein in many conditions such as hypoxia and hypoglycemia (Shweiki et al., "Induction of Vascular Endothelial Growth Factor Expression by Hypoxia and by Glucose Deficiency in Multicell Spheroids: Implications for Tumor Angiogenesis," *Proc. Natl. Acad. Sci. USA* 92:768-772 (1995) and Akiri et al., Regulation of Vascular Endothelial Growth Factor (VEGF) Expression is Mediated by Internal Initiation of Translation and Alternative Initiation of Transcription," *Oncogene* 17:227-236 (1998), which are hereby incorporated by reference in their entirety). Other genes that undergo translation changes in response to internal or external signals are PDGF2 and TGFβ (Tobin et al., "Consequences of Altered TGF-beta Expression and Responsiveness in Breast Cancer: Evidence for Autocrine and Paracrine Effects," *Oncogene* 21:108-118 (2002), which is hereby incorporated by reference in its entirety). During the embryonic stage, when most organ development and cell differentiation takes place, translation regulation plays a key role by altering the expression levels of specific mRNA subsets during a certain time frame whereas the bulk of transcripts remain unaffected (Jackson et al., "The Mechanism of Eukaryotic Translation Initiation and Principles of Its Regulation," *Nat. Rev. Mol. Cell Biol.* 11:113-127 (2010); Sonenberg & Hinnebusch, "Regulation of Translation Initiation in Eukaryotes: Mechanisms and Biological Targets," *Cell* 136: 731-745 (2009); and Gebauer & Hentze, "Molecular Mechanisms of Translational Control," *Nat. Rev. Mol. Cell Biol.* 5:827-835 (2004), which are hereby incorporated by reference in their entirety).

The results presented herein identify several 5' UTRs that may allow translation of modRNA in the heart or liver post ischemic injury. Both Pzp and Serpina 1b 5' UTR showed non-significant and similar in vivo translation ability as a control 5' UTR sequence (FIGS. 3E-3F). Since the control 5' UTR used in the studies described herein is the most commonly used 5' UTR in the modified RNA field (Zangi et al., "Modified mRNA Directs the Fate of Heart Progenitor Cells and Induces Vascular Regeneration after Myocardial Infarction," *Nat. Biotechnol.* 31:898-907 (2013); Carlsson et al., "Biocompatible, Purified VEGF-A mRNA Improves Cardiac Function after Intracardiac Injection 1 Week Post-myocardial Infarction in Swine," *Mol. Ther. Methods Clin. Dev.* 9: 330-346 (2018); Kondrat et al., "Synthesis of Modified mRNA for Myocardial Delivery," *Methods in Molecular Biology* 1521:127-138 (2017); Lui et al., "Driving Vascular Endothelial Cell Fate of Human Multipotent Isl1+ Heart Progenitors with VEGF Modified mRNA," *Cell Res.* 23:1172-1186 (2013); Magadum et al., "Ablation of a Single N-Glycosylation Site in Human FSTL 1 Induces Cardiomyocyte Proliferation and Cardiac Regeneration," *Mol. Ther. Nucleic Acids* 13:133-143 (2018); Mohamed et al., "Regulation of Cell Cycle to Stimulate Adult Cardiomyocyte Proliferation and Cardiac Regeneration," *Cell* 173:104-116 e112 (2018); and Turnbull et al., "Myocardial Delivery of Lipidoid Nanoparticle Carrying modRNA Induces Rapid and Transient Expression," *Mol. Ther.* 24:66-75 (2016), which are hereby incorporated by reference in their entirety), the results presented herein indicate how well the selected 5' UTR sequences performed relative to a premium control.

The studies presented herein focused on the 5' UTR of Ces1d as an enhancer of modRNA translation in cardiac and hepatic ischemic conditions (FIGS. 3A-3F; FIGS. 5A-5D; and FIGS. 7A-7H). Ces1d belongs to a family of carboxylesterases, which have important roles in lipid metabolism and hydrolyze endogenous esters and thioesters. Carboxylesterases are known for their involvement in environmental detoxification as well as pro-drug metabolism. Ces1d is the functional mouse ortholog of human CES1 and has similar protein expression profiles in different cells and tissues. Several of Ces1d's roles are directly associated with lipid metabolism (Dominguez et al., "Integrated Phenotypic and Activity-Based Profiling Links Ces3 to Obesity and Diabetes," *Nat. Chem. Biol.* 10:113-121 (2014); Lian et al., "Ces1d Deficiency Protects Against High-Sucrose Diet-Induced Hepatic Triacylglycerol Accumulation," *J. Lipid Res.* 60:880-891 (2019); and Marrades et al., "A Dysregulation in CES1, APOE and Other Lipid Metabolism-Related Genes is Associated to Cardiovascular Risk Factors Linked to Obesity," *Obes. Facts* 3:312-318 (2010), which are hereby incorporated by reference in their entirety), which is an important process for normal heart function. Fatty acids are the preferred substrates under aerobic conditions (Ford, "Alterations in Myocardial Lipid Metabolism During Myocardial Ischemia and Reperfusion," *Prog. Lipid Res.* 41:6-26 (2002), which is hereby incorporated by reference in its entirety). As Ces1d takes part in lipid metabolism, which MI alters, it is hypothesized that Ces1d mRNA is triggered toward improved translation by ischemia in the heart post-MI. The results presented herein show that Element D is the RNA element in Ces1d that is responsible for elevating mRNA translation post-MI (FIGS. 7A-7H). It is therefore desirable to evaluate Element D and the 5' UTR of Ces1d in the context of different ischemic conditions, as well as in organs other than the heart, liver, and kidney. The fact that the 5' UTR of Ces1d raised translation in the ischemic heart and liver, but not the kidney, is interesting, as all three organs primarily uses fatty acid oxidation for energy. This result may indicate that each organ and physiological condition will need a separate evaluation using approaches similar to those described herein.

The results presented herein identify the 5' UTR of Ces1d, and element D in the 5' UTR of Ces1d as RNA elements that improve modRNA translation in the heart and liver post-ischemic injury. This may have clinical applications, as both organs are heavily targeted with modRNA in different cardiac and hepatic diseases. These results inform the design of superior modRNA constructs which may carry the 5' UTR of Ces1d or Element D of Ces1d for preclinical studies in ischemic cardiac and liver diseases. The results presented herein also provide a platform technology for screening for superior 5' UTRs in different organs under normal or abnormal physiological conditions or diseases.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A nucleic acid molecule comprising:
   a first nucleic acid sequence comprising at least a portion of a 5' untranslated region (5' UTR) of a carboxylesterase gene, wherein the carboxylase is a carboxylase 1D (Ces1D) or a carboxylesterase 1 (CES1), and
   a second nucleic acid sequence encoding a protein of interest, wherein the second nucleic acid sequence is heterologous to and operatively coupled to the first nucleic acid sequence.

2. The nucleic acid molecule according to claim 1, wherein said first and second nucleic acids are modified mRNAs (modRNAs).

3. The nucleic acid molecule according to claim 2, wherein the modRNAs comprise pseudouridine or methylpseudouridine.

4. The nucleic acid molecule according to claim 1, wherein the carboxylesterase gene is a carboxylesterase 1D (Ces1d) gene.

5. The nucleic acid molecule according to claim 4, wherein the first nucleic acid sequence comprises the nucleic acid sequence of SEQ ID NO:1.

6. The nucleic acid molecule according to claim 4, wherein the first nucleic acid sequence comprises the nucleic acid sequence of SEQ ID NO:10.

7. The nucleic acid molecule according to claim 1, wherein the carboxylesterase gene is a carboxylesterase 1 (CES1) gene.

8. The nucleic acid molecule according to claim 7, wherein the first nucleic acid sequence comprises the nucleic acid sequence of SEQ ID NO:5.

9. The nucleic acid molecule according to claim 7, wherein the first nucleic acid sequence comprises the nucleic acid sequence of SEQ ID NO:29.

10. The nucleic acid molecule according to claim 1, wherein the protein of interest is a cell cycle inducer.

11. The nucleic acid molecule according to claim 10, wherein the cell cycle inducer is selected from the group consisting of Lin28, Pyruvate Kinase Muscle Isozyme M2 (Pkm2), β-catenin, caERBB2, Yes Associated Protein 1 (YAP), Cyclin D1, and c-Myc.

12. A method of expressing a protein of interest in a target cell, said method comprising:
    providing the nucleic acid molecule according to claim 1 and
    contacting a target cell with the nucleic acid molecule, wherein said nucleic acid molecule is translated to express the protein of interest in the target cell.

13. The method according to claim 12, wherein the target cell is an ischemic cell.

14. The method according to claim 12, wherein the target cell is a cardiomyocyte or hepatocyte.

15. The method according to claim 12, wherein said contacting is carried out after an ischemic event in the target cell.

16. The method according to claim 12, wherein said protein of interest comprises a cell cycle inducer protein selected from the group consisting of Lin28, Pkm2, β-catenin, caERBB2, Yes Associated Protein 1 (YAP), Cyclin D1, and cMYC.

17. The method according to claim 16, wherein said cycle inducer is Lin28 or Pkm2.

18. The method according to claim 12, wherein the protein of interest comprises a cell cycle inducer.

19. The method according to claim 18, wherein the cell cycle inducer is Lin28 or Pkm2.

\* \* \* \* \*

SEQUENCE LISTING

```
<160> NUMBER OF SEQ ID NOS: 57

<210> SEQ ID NO 1
<211> LENGTH: 85
<212> TYPE: DNA
<213> ORGANISM: Mus musculis

<400> SEQUENCE: 1
aggaggcggg tcccctggtc cacaacagaa gcattgctaa agcagcagat agctcagaga      60
cccacagagc ccttgtcctt ccaca                                          85

<210> SEQ ID NO 2
<211> LENGTH: 51
<212> TYPE: DNA
<213> ORGANISM: Rattus norvegicus
```

-continued

```
<400> SEQUENCE: 2
tgctaaagga acaaatagcc cacagatccg cagaacccct gtccttccac a          51

<210> SEQ ID NO 3
<211> LENGTH: 98
<212> TYPE: DNA
<213> ORGANISM: Cavia porcellus

<400> SEQUENCE: 3
gaattcacag gatcatatcc agtactgttc aaggacaagt gcatttccat gaatcaggac    60
agagagctcc ttggctccca acctgttgtc ttcccatg                         98

<210> SEQ ID NO 4
<211> LENGTH: 76
<212> TYPE: DNA
<213> ORGANISM: Meriones unguiculatus

<400> SEQUENCE: 4
caggaccttg ggtccacaac agcattgcta aagcagcaga tatcacacag acccacggaa    60
cccttgtcct tccaca                                                  76

<210> SEQ ID NO 5
<211> LENGTH: 108
<212> TYPE: DNA
<213> ORGANISM: Homo sapiens

<400> SEQUENCE: 5
agcgcagggc ggtaactctg ggcggggctg ggctccaggg ctggacagca cagtccctct    60
gaactgcaca gagacctcgc aggccccgag aactgtcgcc cttccacg              108

<210> SEQ ID NO 6
<211> LENGTH: 69
<212> TYPE: DNA
<213> ORGANISM: Macaca mulatta

<400> SEQUENCE: 6
ggctttactg ctatctccca attagaggat taggcaattg gcagctcagg gtggtaactc    60
agggcctgg                                                          69

<210> SEQ ID NO 7
<211> LENGTH: 22
<212> TYPE: DNA
<213> ORGANISM: Artificial Sequence
<220> FEATURE:
<223> OTHER INFORMATION: Mouse Element A

<400> SEQUENCE: 7
aggaggcggg tcccctggtc ca                                           22

<210> SEQ ID NO 8
<211> LENGTH: 23
<212> TYPE: DNA
<213> ORGANISM: Artificial Sequence
<220> FEATURE:
<223> OTHER INFORMATION: Mouse Element B

<400> SEQUENCE: 8
caacagaagc attgctaaag cag                                          23

<210> SEQ ID NO 9
<211> LENGTH: 8
```

-continued

```
<212> TYPE: DNA
<213> ORGANISM: Artificial Sequence
<220> FEATURE:
<223> OTHER INFORMATION: Mouse Element C

<400> SEQUENCE: 9 cagatagc                                                            8

<210> SEQ ID NO 10
<211> LENGTH: 19
<212> TYPE: DNA
<213> ORGANISM: Artificial Sequence
<220> FEATURE:
<223> OTHER INFORMATION: Mouse Element D

<400> SEQUENCE: 10
tcagagaccc acagagccc                                               19

<210> SEQ ID NO 11
<211> LENGTH: 13
<212> TYPE: DNA
<213> ORGANISM: Artificial Sequence
<220> FEATURE:
<223> OTHER INFORMATION: Mouse Element E

<400> SEQUENCE: 11
ttgtccttcc aca                                                     13

<210> SEQ ID NO 12
<211> LENGTH: 11
<212> TYPE: DNA
<213> ORGANISM: Artificial Sequence
<220> FEATURE:
<223> OTHER INFORMATION: Rat Element B

<400> SEQUENCE: 12
tgctaaagga a                                                       11

<210> SEQ ID NO 13
<211> LENGTH: 8
<212> TYPE: DNA
<213> ORGANISM: Artificial Sequence
<220> FEATURE:
<223> OTHER INFORMATION: Rat Element C

<400> SEQUENCE: 13 caaatagc                                                            8

<210> SEQ ID NO 14
<211> LENGTH: 19
<212> TYPE: DNA
<213> ORGANISM: Artificial Sequence
<220> FEATURE:
<223> OTHER INFORMATION: Rat Element D

<400> SEQUENCE: 14
ccacagatcc gcagaaccc                                               19

<210> SEQ ID NO 15
<211> LENGTH: 13
<212> TYPE: DNA
<213> ORGANISM: Artificial Sequence
<220> FEATURE:
<223> OTHER INFORMATION: Rat Element E

<400> SEQUENCE: 15
```
ttgtccttcc aca                                              13

<210> SEQ ID NO 16
<211> LENGTH: 29
<212> TYPE: DNA
<213> ORGANISM: Artificial Sequence
<220> FEATURE:
<223> OTHER INFORMATION: Pig Element A

<400> SEQUENCE: 16
gaattcacag gatcatatcc agtactgtt                             29

<210> SEQ ID NO 17
<211> LENGTH: 30
<212> TYPE: DNA
<213> ORGANISM: Artificial Sequence
<220> FEATURE:
<223> OTHER INFORMATION: Pig Element B

<400> SEQUENCE: 17
caaggacaag tgcatttcca tgaatcagga                            30

<210> SEQ ID NO 18
<211> LENGTH: 8
<212> TYPE: DNA
<213> ORGANISM: Artificial Sequence
<220> FEATURE:
<223> OTHER INFORMATION: Pig Element C

<400> SEQUENCE: 18 cagagagc                                                    8

<210> SEQ ID NO 19
<211> LENGTH: 16
<212> TYPE: DNA
<213> ORGANISM: Artificial Sequence
<220> FEATURE:
<223> OTHER INFORMATION: Pig Element D

<400> SEQUENCE: 19
tccttggctc ccaacc                                           16

<210> SEQ ID NO 20
<211> LENGTH: 15
<212> TYPE: DNA
<213> ORGANISM: Artificial Sequence
<220> FEATURE:
<223> OTHER INFORMATION: Pig Element E

<400> SEQUENCE: 20
tgttgtcttc ccatg                                            15

<210> SEQ ID NO 21
<211> LENGTH: 16
<212> TYPE: DNA
<213> ORGANISM: Artificial Sequence
<220> FEATURE:
<223> OTHER INFORMATION: Gerbil Element A

<400> SEQUENCE: 21
caggaccttg ggtcca                                           16

<210> SEQ ID NO 22
<211> LENGTH: 18
<212> TYPE: DNA
<213> ORGANISM: Artificial Sequence

```
<220> FEATURE:
<223> OTHER INFORMATION: Gerbil Element B

<400> SEQUENCE: 22
caacagcatt gctaaagc                                                        18

<210> SEQ ID NO 23
<211> LENGTH: 8
<212> TYPE: DNA
<213> ORGANISM: Artificial Sequence
<220> FEATURE:
<223> OTHER INFORMATION: Gerbil Element C

<400> SEQUENCE: 23 agcagata                                                                   8

<210> SEQ ID NO 24
<211> LENGTH: 21
<212> TYPE: DNA
<213> ORGANISM: Artificial Sequence
<220> FEATURE:
<223> OTHER INFORMATION: Gerbil Element D

<400> SEQUENCE: 24
tcacacagac ccacggaacc c                                                    21

<210> SEQ ID NO 25
<211> LENGTH: 13
<212> TYPE: DNA
<213> ORGANISM: Artificial Sequence
<220> FEATURE:
<223> OTHER INFORMATION: Gerbil Element E

<400> SEQUENCE: 25
ttgtccttcc aca                                                             13

<210> SEQ ID NO 26
<211> LENGTH: 37
<212> TYPE: DNA
<213> ORGANISM: Artificial Sequence
<220> FEATURE:
<223> OTHER INFORMATION: Human Element A

<400> SEQUENCE: 26
agcgcagggc ggtaactctg ggcggggctg ggctcca                                  37

<210> SEQ ID NO 27
<211> LENGTH: 31
<212> TYPE: DNA
<213> ORGANISM: Artificial Sequence
<220> FEATURE:
<223> OTHER INFORMATION: Human Element B

<400> SEQUENCE: 27
gggctggaca gcacagtccc tctgaactgc a                                         31

<210> SEQ ID NO 28
<211> LENGTH: 12
<212> TYPE: DNA
<213> ORGANISM: Artificial Sequence
<220> FEATURE:
<223> OTHER INFORMATION: Human Element C

<400> SEQUENCE: 28
cagagacctc gc                                                             12
```

-continued

```
<210> SEQ ID NO 29
<211> LENGTH: 13
<212> TYPE: DNA
<213> ORGANISM: Artificial Sequence
<220> FEATURE:
<223> OTHER INFORMATION: Human Element D

<400> SEQUENCE: 29
aggccccgag aac                                                  13

<210> SEQ ID NO 30
<211> LENGTH: 15
<212> TYPE: DNA
<213> ORGANISM: Artificial Sequence
<220> FEATURE:
<223> OTHER INFORMATION: Human Element E

<400> SEQUENCE: 30
tgtcgccctt ccacg                                                15

<210> SEQ ID NO 31
<211> LENGTH: 23
<212> TYPE: DNA
<213> ORGANISM: Artificial Sequence
<220> FEATURE:
<223> OTHER INFORMATION: Consensus Element A
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 31
ggannnnggg gcncatancc can                                       23

<210> SEQ ID NO 32
<211> LENGTH: 31
<212> TYPE: DNA
<213> ORGANISM: Artificial Sequence
<220> FEATURE:
<223> OTHER INFORMATION: Consensus Element B
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
```

```
<400> SEQUENCE: 32
acaggncnag aacccatngc ctnccatnaa t                                          31

<210> SEQ ID NO 33
<211> LENGTH: 12
<212> TYPE: DNA
<213> ORGANISM: Artificial Sequence
<220> FEATURE:
<223> OTHER INFORMATION: Consensus Element C
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 33
caganannag an                                                              12

<210> SEQ ID NO 34
<211> LENGTH: 19
<212> TYPE: DNA
<213> ORGANISM: Artificial Sequence
<220> FEATURE:
<223> OTHER INFORMATION: Consensus Element D
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t

<400> SEQUENCE: 34
ctcccnggct ccnancann                                                       19

<210> SEQ ID NO 35
<211> LENGTH: 11
<212> TYPE: DNA
<213> ORGANISM: Artificial Sequence
<220> FEATURE:
<223> OTHER INFORMATION: Consensus Element E

<400> SEQUENCE: 35
ttgtcttcca t                                                               11

<210> SEQ ID NO 36
<211> LENGTH: 630
<212> TYPE: DNA
<213> ORGANISM: Mus musculis

<400> SEQUENCE: 36
atgggctcgg tgtccaacca gcagtttgca ggtggctgcg ccaaggcagc ggagaaggcg    60
```

-continued

```
ccagaggagg cgccgcctga cgcggcccga gcggcagacg agccgcagct gctgcacggg      120
gccggcatct gtaagtggtt caacgtgcgc atggggttcg gcttcctgtc tatgaccgcc      180
cgcgctgggg tcgcgctcga cccccggtg dacgtctttg tgcaccagag caagctgcac      240
atggaagggt tccgaagcct caaggagggt gaggcggtgg agttcacctt taagaagtct      300
gccaagggtc tggaatccat ccgtgtcact ggccctggtg gtgtgttctg tattgggagt      360
gagcggcggc caaaagggaa gaacatgcag aagcgaagat ccaaaggaga caggtgctac      420
aactgcggtg ggctagacca tcatgccaag gaatgcaagc tgccacccca gcccaagaag      480
tgccactttt gccaaagcat caaccatatg gtggcctcgt gtccactgaa ggcccagcag      540
ggccccagtt ctcagggaaa gcctgcctac ttccgggagg aagaggaaga gatccacagc      600
cctgccctgc tcccagaagc ccagaattga                                        630

<210> SEQ ID NO 37
<211> LENGTH: 1596
<212> TYPE: DNA
<213> ORGANISM: Mus musculis

<400> SEQUENCE: 37
atgccgaagc cacacagtga agcagggact gccttcattc agacccagca gctccatgca       60
gccatggctg acaccttcct ggaacacatg tgccgcctgg acattgactc tgcccccatc      120
acggcccgca acactggcat catttgtacc attgggcctg cttcccgatc tgtggagatg      180
ctgaaggaga tgattaagtc tggaatgaat gtggctcggc tgaatttctc tcatggaacc      240
catgagtacc atgcagagac catcaagaat gtccgtgaag ccacagaaag ctttgcatct      300
gatcccattc tctaccgtcc tgttgcggtg gctctggata caaagggacc tgagatccgg      360
actggactca tcaagggcag cggcaccgct gaggtggagc tgaagaaggg agccactctg      420
aagatcaccc tggacaacgc ttacatggag aagtgtgacg agaacatcct gtggctggac      480
tacaagaaca tctgcaaggt ggtggaggtg ggcagcaaga tctacgtgga cgatgggctc      540
atctcactgc aggtgaagga gaaaggcgct gacttcctgg tgacggaggt ggagaatggt      600
ggctccttgg gcagcaagaa gggcgtgaac ctgccgggcg ctgctgtgga tctccccgct      660
gtgtcggaaa aggacatcca ggacctgaag tttggggtgg agcaggatgt ggacatggtg      720
tttgcatctt tcatccgcaa ggcagccgac gtgcatgaag tcaggaaggt gctgggagag      780
aagggcaaga acatcaagat catcagcaaa atcgagaacc atgaaggcgt ccgcaggttt      840
gatgagatct tggaggccag tgatgggatc atggtggctc gtggtgacct gggcattgag      900
attcctgcag agaaggtctt cctggctcag aagatgatga tcgggcgatg caaccgagct      960
gggaagcctg tcatctgtgc cacacagatg ctggagagca tgatcaagaa gccacgcccc     1020
acccgtgctg aaggcagtga tgtggccaat gcagtcctgg atggagcaga ctgcatcatg     1080
ctgtctggag aaacagccaa gggggactac cctctggagg ctgttcgcat gcagcacctg     1140
attgcccgag aggcagaggc tgccatctac cacttgcagc tattcgagga actccgccgc     1200
ctggcgccca ttaccagcga ccccacagaa gctgccgccg tgggtgccgt ggaggcctcc     1260
ttcaagtgct gcagtggggc cattatcgtg ctcaccaagt ctggcaggag tgctcaccaa     1320
gtggccaggt accgccctcg ggctcctatc attgccgtga ctcgaaatcc ccagactgct     1380
cgccaggccc atctgtaccg tggcatcttc cctgtgctgt gtaaggatgc cgtgctgaat     1440
gcctgggctg aggatgtcga ccttcgtgta aacttggcca tggatgttgg caaggcccga     1500
ggcttcttca gaaagggaga tgtggtcatt gtgctgaccg ggtggcgccc tggctctgga     1560
```

-continued

```
ttcaccaaca ccatgcgtgt agtgcctgta ccttga                         1596

<210> SEQ ID NO 38
<211> LENGTH: 2346
<212> TYPE: DNA
<213> ORGANISM: Mus musculis

<400> SEQUENCE: 38
atggctactc aagctgacct gatggagttg gacatggcca tggagccgga cagaaaagct     60
gctgtcagcc actggcagca gcagtcttac ttggattctg gaatccattc tggtgccacc    120
accacagctc cttccctgag tggcaagggc aaccctgagg aagaagatgt tgacacctcc    180
caagtccttt atgaatggga gcaaggcttt tcccagtcct tcacgcaaga gcaagtagct    240
gatattgacg ggcagtatgc aatgactagg gctcagaggg tccgagctgc catgttccct    300
gagacgctag atgagggcat gcagatccca tccacgcagt ttgacgctgc tcatcccact    360
aatgtccagc gcttggctga accatcacag atgttgaaac atgcagttgt caatttgatt    420
aactatcagg atgacgcgga acttgccaca cgtgcaattc ctgagctgac aaaaactgcta   480 aacgatgagg accaggtggt agttaataaa gctgctgtta tggtccatca gctttccaaa    540
aaggaagctt ccagacatgc catcatgcgc tcccctcaga tggtgtctgc cattgtacgc    600
accatgcaga atacaaatga tgtagagaca gctcgttgta ctgctgggac tctgcacaac    660
ctttctcacc accgcgaggg cttgctggcc atctttaagt ctggtggcat cccagcgctg    720
gtgaaaatgc ttgggtcacc agtggattct gtactgttct acgccatcac gacactgcat    780
aatctcctgc tccatcagga aggagctaaa atggcagtgc gcctagctgg tggactgcag    840
aaaatggttg ctttgctcaa caaaacaaac gtgaaattct tggctattac aacagactgc    900
cttcagatct tagcttatgg caatcaagag agcaagctca tcattctggc cagtggtgga    960
ccccaagcct tagtaaacat aatgaggacc tacacttatg agaagcttct gtggaccaca   1020
agcagagtgc tgaaggtgct gtctgtctgc tctagcaaca agccggccat tgtagaagct   1080
ggtgggatgc aggcactggg gcttcatctg acagacccaa gtcagcgact tgttcaaaac   1140
tgtctttgga ctctcagaaa cctttcagat gcagcgacta gcaggaagg gatggaaggc    1200 ctccttggga ctctagtgca gcttctgggt tccgatgata taaatgtggt cacctgtgca   1260
gctggaattc tctctaacct cacttgcaat aattacaaaa acaagatgat ggtgtgccaa   1320
gtgggtggca tagaggctct tgtacgcacc gtccttcgtg ctggtgacag ggaagacatc   1380
actgagcctg ccatctgtgc tcttcgtcat ctgaccagcc ggcatcagga agccgagatg   1440
gcccagaatg ccgttcgcct tcattatgga ctgcctgttg tggttaaact cctgcaccca   1500
ccatcccact ggcctctgat aaaggcaact gttggattga ttcgaaacct tgccctttgc   1560
ccagcaaatc atgcgccttt gcgggaacag ggtgctattc cacgactagt tcagctgctt   1620
gtacgagcac atcaggacac ccaacggcgc acctccatgg gtggaacgca gcagcagttt   1680
gtggagggcg tgcgcatgga ggagatagta gaagggtgta ctggagctct ccacatcctt   1740
gctcgggacg ttcacaaccg gattgtaatc cgaggactca ataccattcc attgtttgtg   1800
cagttgcttt attctcccat tgaaaatatc caaagagtag ctgcagggt cctctgtgaa    1860 cttgctcagg acaaggaggc tgcagaggcc attgaagctg agggagccac agctccctg    1920 acagagttac tccactccag gaatgaaggc gtggcaacat acgcagctgc tgtcctattc    1980
cgaatgtctg aggacaagcc acaggattac aagaagcggc tttcagtcga gctgaccagt    2040
```

-continued

```
tccctcttca ggacagagcc aatggcttgg aatgagactg cagatcttgg actggacatt    2100
ggtgcccagg gagaagccct tggatatcgc caggatgatc ccagctaccg ttcttttcac    2160
tctggtggat acggccagga tgccttgggg atggaccct a tgatggagca tgagatgggt    2220
ggccaccacc ctggtgctga ctatccagtt gatgggctgc ctgatctggg acacgcccag    2280
gacctcatgg atgggctgcc cccaggtgat agcaatcagc tggcctggtt tgatactgac    2340
ctgtaa                                                               2346

<210> SEQ ID NO 39
<211> LENGTH: 3678
<212> TYPE: DNA
<213> ORGANISM: Mus musculis

<400> SEQUENCE: 39
atgaagctgc ggctgcccgc ctctcctgag acacacctgg acatgctgcg gcacctgtac      60
cagggctgtc aggtggtgca gggcaacctg gaactgacct acctgcccac caacgccagc     120
ctgagctttc tgcaggacat ccaggaagtg cagggctacg tcctgatcgc ccacaaccag     180
gtccgacagg tgccctgca gagactgaga atcgtgcggg gcacccagct gttcgaggac      240
aattatgccc tggccgtgct ggacaacggc gaccccctga acaataccac ccctgtgaca     300
ggcgccagcc ctggcggact gagagaactg cagctgcgga gcctgaccga gatcctgaag     360
ggcggcgtgc tgatccagag aaaccccag ctgtgctacc aggacaccat cctgtggaag      420
gacatcttcc acaagaacaa ccagctggcc ctgaccctga tcgacaccaa cagaagcaga     480
gcctgccacc cctgcagccc catgtgcaag ggctctagat gttggggcga gagcagcgag     540
gactgccagt ccctgaccag aacagtgtgt gccggcggat cgccagatg caagggccct      600 ctgcctaccg attgctgcca cgagcagtgt gccgctggct gtacaggccc caagcacagc     660
gattgcctgg cctgcctgca ctttaaccac agcggcatct gcgagctgca ctgccctgcc     720
ctggtcacct acaacaccga cacttcgag agcatgccca accccgaggg cagatacacc      780
ttcggcgcca gctgtgtgac cgcctgcccc tacaactacc tgagcaccga gtgtgggcagc    840 tgcaccctcg tgtgcccccct gcacaatcag gaagtgaccg ccgaggacgg cacccagaga    900
tgcgagaagt gcagcaagcc ctgcgccaga gtgtgctacg gcctgggcat ggaacacctg     960
agagaagtgc gggccgtgac cagcgccaat atccaggaat cgccggctg caagaagatc     1020 tttggctccc tggcctttct gcccgagagc ttcgatggcg accctgcctc taataccgcc    1080
cctctgcagc cagagcagct ccaggtgttc gagacactgg aagagatcac cggctacctg    1140
tacatcagcg cctggcccga cagcctgccc gatctgagcg tgttccagaa tctgcaggtc    1200
atcagaggcc ggatcctgca caacggcgcc tacagcctga cactgcaggg cctgggaatc    1260
agctggctgg gcctgagatc tctgagagag ctgggcagcg cctggctct gatccaccac     1320 aacacccacc tgtgcttcgt gcacaccgtg ccctgggacc agctgtttag aaaccctcac    1380
caggcactgc tgcacaccgc caacagaccc gaggatgagt gtgtgggcga aggcctggct    1440
tgccatcagc tgtgcgctag aggccactgt tggggccctg acctaccca gtgcgtgaac     1500 tgctcccagt cctgcggggg ccaggaatgc gtggaagagt gcagagtgct gcagggactg    1560
ccccgcgagt acgtgaacgc cagacactgc ctgccttgcc accctgagtg ccagcctcag    1620
aatggcagcg tgacctgctt cggccctgag gccgatcagt gtgtggcctg cgcccactac    1680
aaggaccccc cattctgcgt ggccagatgc cctagcggcg tgaagcccga cctgagctac    1740
atgcccatct ggaagttccc cgacgaggaa ggcgcctgcc agccttgtcc catcaactgc    1800
```

```
acccacagct gcgtggacct ggacgacaag ggctgtcctg ccgagcagag agccagcccc      1860
ctgacctcta tcatctccgc cgtggaaggc atcctgctgg tggtggtgct gggcgtggtg      1920
ttcggcatcc tgatcaagcg gcggcagcag aagatccgga agtacaccat gcggcggctg      1980
ctgcaggaaa ccgagctggt cgagcctctg acaccaagcg cgccatgcc taaccaggcc       2040 cagatgcgga tcctgaaaga gacagagctg cggaaagtga aggtgctggg atccggcgcc      2100
ttcggcacag tgtacaaggg aatctggatc cccgacggcg agaacgtgaa gatccccgtg      2160
gccatcaagg tgctgagaga gaacaccagc cccaaggcca caaagagat cctggacgag       2220 gcctacgtga tggccggcgt gggcagccct tatgtgtcca gactgctggg catctgcctg      2280
accagcaccg tgcagctggt cactcagctg atgccttacg gctgcctgct ggaccacgtg      2340
cgcgagaata gaggcagact gggcagccag gacctgctga actggtgcat gcagatcgcc      2400
aagggcatga gctacctcga ggacgtgcgg ctggtgcaca gagatctggc cgccagaaac      2460
gtgctcgtga agtcccccaa ccacgtgaaa atcaccgact tcggactggc ccggctgctg      2520
gacatcgacg agacagagta tcacgccgac ggcggcaagg tgcccatcaa gtggatggcc      2580
ctggaatcca tcctgcggcg gaggttcacc caccagagcg acgtgtggtc ttacggcgtg      2640
accgtgtggg agctgatgac attcggagcc aagccctacg acggcatccc cgccagagag      2700
atccccgatc tgctggaaaa gggcgagaga ctgccccagc cccccatctg caccatcgac      2760
gtgtacatga ttatggtcaa gtgctggatg atcgacagcg agtgccggcc cagattccgc      2820
gagctggtgt ccgagttctc cagaatggcc cgggaccccc agagattcgt ggtcatccag      2880
aacgaggacc tgggccctgc ctcccccctg gactccacct tttaccggtc cctgctggaa      2940
gatgacgaca tgggcgacct ggtggacgcc gaggaatacc tggtgcccca gcagggcttc      3000
ttctgccctg atcctgctcc tggcgctggc ggcatggtgc atcacagaca cagaagctcc      3060
agcaccagaa gcggaggcgg cgatctgacc ctgggactgg aaccttctga ggaagaggcc      3120
cctagaagcc ccctggcccc tagtgaaggg gcaggatctg atgtgttcga cggggacctg      3180
ggaatgggcg ctgccaaagg actgcagagt ctgcccaccc acgacccag cccactgcag       3240 aggtacagcg aggatcctac cgtgcctctg cccagcgaga cagatggcta cgtggccct        3300 ctgacctgta gcccccagcc cgagtatgtg aaccagcccg atgtgcggcc tcagcctcct      3360
agccctagag aaggacctct gcctgccgct agacctgccg cgctacccct ggaaagaccc      3420
aagacactga gccccggcaa gaacggcgtg gtcaaggacg tgttcgcctt tggcggagcc      3480
gtggaaaacc ccgagtacct gacacctcag ggcggagcag cacctcagcc acccctcca       3540 ccagccttca gccccgcctt cgacaacctg tactactggg atcaggaccc tcccgagaga      3600
ggcgccccac ctagcacctt taagggcacc cctaccgccg agaatcctga gtacctgggg      3660
ctggacgtgc ccgtctaa                                                    3678
```

<210> SEQ ID NO 40
<211> LENGTH: 1572
<212> TYPE: DNA
<213> ORGANISM: Mus musculis

<400> SEQUENCE: 40

```
atggactaca agacgatga cgacaagctt gcggccgcga attcaagctt agccaccatg        60
gactacaaag acgatgacga taaagcaagg ctcgaatcgg tacctaagga tcccgggcag      120
cagccgccgc ctcaaccggc cccccagggc caagggcagc cgccttcgca gccccgcag       180
```

-continued

```
gggcagggcc cgccgtccgg acccgggcaa ccggcacccg cggcgaccca ggcggcgccg      240
caggcacccc ccgccgggca tcagatcgtg cacgtccgcg gggactcgga gaccgacctg      300
gaggcgctct tcaacgccgt catgaacccc aagacggcca acgtgcccca gaccgtgccc      360
atgaggctcc ggaagctgcc cgactccttc ttcaagccgc cggagcccaa atcccactcc      420
cgacaggcca gtactgatgc aggcactgca ggagccctga ctccacagca tgttcgagct      480
catgcctctc cagcttctct gcagttggga gctgtttctc ctgggacact gaccecccact      540 ggagtagtct ctggcccagc agctacaccc acagctcagc atcttcgaca gtcttctttt      600
gagatacctg atgatgtacc tctgccagca ggttgggaga tggcaaagac atcttctggt      660
cagagatact tcttaaatca catcgatcag acaacaacat ggcaggaccc caggaaggcc      720
atgctgtccc agatgaacgt cacagccccc accagtccac cagtgcagca gaatatgatg      780
aactcggctt caggtcctct tcctgatgga tgggaacaag ccatgactca ggatggagaa      840
atttactata taaaccataa gaacaagacc acctcttggc tagacccaag gcttgaccct      900
cgttttgcca tgaaccagag aatcagtcag agtgctccag tgaaacagcc accaccctg      960 gctccccaga gcccacaggg aggcgtcatg ggtggcagca actccaacca gcagcaacag     1020
atgcgactgc agcaactgca gatggagaag gagaggctgc ggctgaaaca gcaagaactg     1080
cttcggcagg agttagccct gcgtagccag ttaccaacac tggagcagga tggtgggact     1140
caaaatccag tgtcttctcc cgggatgtct caggaattga gaacaatgac gaccaatagc     1200
tcagatcctt tccttaacag tggcacctat cactctcgag atgagagtac agacagtgga     1260
ctaagcatga gcagctacag tgtccctcga accccagatg acttcctgaa cagtgtggat     1320
gagatggata caggtgatac tatcaaccaa gcaccctgc cctcacagca gaaccgtttc     1380
ccagactacc ttgaagccat tcctgggaca aatgtggacc ttggaacact ggaaggagat     1440
ggaatgaaca tagaaggaga ggagctgatg ccaagtctgc aggaagcttt gagttctgac     1500
atccttaatg acatggagtc tgttttggct gccaccaagc tagataaaga aagctttctt     1560
acatggttat ag                                                        1572
```

```
<210> SEQ ID NO 41
<211> LENGTH: 888
<212> TYPE: DNA
<213> ORGANISM: Mus musculis

<400> SEQUENCE: 41
```

```
atggaacacc agctcctgtg ctgcgaagtg gagaccatcc gccgcgcgta ccctgacacc       60
aatctcctca cgaccgggt gctgcgagcc atgctcaaga cggaggagac ctgtgcgccc      120
tccgtatctt acttcaagtg cgtgcagaag gagattgtgc catccatgcg gaaaatcgtg      180
gccacctgga tgctggaggt ctgtgaggag cagaagtgcg aagaggaggt cttcccgctg      240
gccatgaact acctggaccg cttcctgtcc ctggagccct tgaagaagag ccgcctgcag      300
ctgctggggg ccacctgcat gttcgtggcc tctaagatga aggagaccat tcccttgact      360
gccgagaagt tgtgcatcta cactgacaac tctatccggc ccgaggagct gctgcaaatg      420
gaactgcttc tggtgaacaa gctcaagtgg aacctggccg ccatgactcc ccacgatttc      480
atcgaacact tcctctccaa aatgccagag gcggatgaga acaagcagac catccgcaag      540
catgcacaga cctttgtggc cctctgtgcc acagatgtga agttcatttc caacccaccc      600
tccatggtag ctgctgggag cgtggtggct gcgatgcaag gcctgaacct gggcagcccc      660
aacaacttcc tctcctgcta ccgcacaacg cactttcttt ccagagtcat caagtgtgac      720
```

```
ccggactgcc tccgtgcctg ccaggaacag attgaagccc ttctggagtc aagcctgcgc      780
caggcccagc agaacgtcga ccccaaggcc actgaggagg aggggggaagt ggaggaagag      840 gctggtctgg cctgcacgcc caccgacgtg cgagatgtgg acatctga                   888

<210> SEQ ID NO 42
<211> LENGTH: 1320
<212> TYPE: DNA
<213> ORGANISM: Mus musculis

<400> SEQUENCE: 42
atgccgctga acgtgagctt taccaaccgc aactatgatc tggattatga tagcgtgcag       60
ccgtattttt attgcgatga agaagaaaac ttttatcagc agcagcagca gagcgaactg      120
cagccgccgg cgccgagcga agatatttgg aaaaaatttg aactgctgcc gacccgccg       180 ctgagcccga ccgccgcag cggcctgtgc agcccgagct atgtggcggt gaccccgttt      240
agcctgcgcg cgataacga tggcggcggc ggcagcttta gcaccgcgga tcagctggaa      300
atggtgaccg aactgctggg cggcgatatg gtgaaccaga gctttatttg cgatccggat      360
gatgaaacct ttattaaaaa cattattatt caggattgca tgtggagcgg ctttagcgcg      420
gcggcgaaac tggtgagcga aaaactggcg agctatcagg cggcgcgcaa agatagcggc      480
agcccgaacc cggcgcgcgg ccatagcgtg tgcagcacca gcagcctgta tctgcaggat      540
ctgagcgcgg cggcgagcga atgcattgat ccgagcgtgg tgtttccgta tccgctgaac      600
gatagcagca gcccgaaaag ctgcgcgagc caggatagca gcgcgtttag cccgagcagc      660
gatagcctgc tgagcagcac cgaaagcagc ccgcagggca gcccggaacc gctggtgctg      720
catgaagaaa ccccgccgac caccagcagc gatagcgaag aagaacagga agatgaagaa      780
gaaattgatg tggtgagcgt ggaaaaaacgc caggcgccgg gcaaacgcag cgaaagcggc      840
agcccgagcg cgggcggcca tagcaaaccg ccgcatagcc cgctggtgct gaaacgctgc      900
catgtgagca cccatcagca taactatgcg gcgccgccga gcacccgcaa agattatccg      960
gcggcgaaac gcgtgaaact ggatagcgtg cgcgtgctgc gccagattag caacaaccgc     1020
aaatgcacca gcccgcgcag cagcgatacc gaagaaaacg tgaaacgccg cacccataac     1080
gtgctggaac gccagcgccg caacgaactg aaacgcagct tttttgcgct gcgcgatcag     1140
attccggaac tggaaaacaa cgaaaaagcg ccgaaagtgg tgattctgaa aaaagcgacc     1200
gcgtatattc tgagcgtgca ggcggaagaa cagaaactga ttagcgaaga agatctgctg     1260
cgcaaacgcc gcgaacagct gaaacataaa ctggaacagc tgcgcaacag ctgcgcgtaa     1320

<210> SEQ ID NO 43
<211> LENGTH: 630
<212> TYPE: DNA
<213> ORGANISM: Homo sapiens

<400> SEQUENCE: 43
atgggctccg tgtccaacca gcagtttgca ggtggctgcg ccaaggcggc agaagaggcg       60
cccgaggagg cgccggagga cgcggcccgg gcggcggacg agcctcagct gctgcacggt      120
gcgggcatct gtaagtggtt caacgtgcgc atggggttcg gcttcctgtc catgaccgcc      180
cgcgccgggg tcgcgctcga cccccccagtg gatgtctttg tgcaccagag taagctgcac      240
atggaagggt tccggagctt gaaggagggt gaggcagtgg agttcacctt taagaagtca      300
gccaagggtc tggaatccat ccgtgtcacc ggacctggtg gagtattctg tattgggagt      360
```

-continued

```
gagaggcggc caaaaggaaa gagcatgcag aagcgcagat caaaaggaga caggtgctac        420
aactgtggag gtctagatca tcatgccaag gaatgcaagc tgccacccca gcccaagaag        480
tgccacttct gccagagcat cagccatatg gtagcctcat gtccgctgaa ggcccagcag        540
ggccctagtg cacagggaaa gccaacctac tttcgagagg aagaagaaga aatccacagc        600
cctaccctgc tcccggaggc acagaattga                                         630

<210> SEQ ID NO 44
<211> LENGTH: 1818
<212> TYPE: DNA
<213> ORGANISM: Homo Sapiens

<400> SEQUENCE: 44
atgcagtgga gctcagagag aggagaacgg ctcctcacgc ctgggggcctg ctcttcagaa         60 gtccccagcg ccgttccttc cagatcaggc ggctctccag ggcacaccgt attcagctct        120
gagcggtctt tgctagtgag gccaaggagc caccctgagc caaaaggggga gcattatgtc       180 accggaagcc caaccccaga gaaccaaagg acctcagcgc ccatgtcgaa gccccatagt        240
gaagccggga ctgccttcat tcagaccccag cagctgcacg cagccatggc tgacacattc       300
ctggagcaca tgtgccgcct ggacattgat tcaccaccca tcacagcccg gaacactggc        360
atcatctgta ccattggccc agcttcccga tcagtggaga cgttgaagga gatgattaag        420
tctggaatga atgtggctcg tctgaacttc tctcatggaa ctcatgagta ccatgcggag        480
accatcaaga atgtgcgcac agccacggaa agctttgctt ctgaccccat cctctaccgg        540
cccgttgctg tggctctaga cactaaagga cctgagatcc gaactgggct catcaagggc        600
agcggcactg cagaggtgga gctgaagaag ggagccactc tcaaaatcac gctggataac        660
gcctacatgg aaaagtgtga cgagaacatc ctgtggctgg actacaagaa catctgcaag        720
gtggtggaag tgggcagcaa gatctacgtg gatgatgggc ttatttctct ccaggtgaag        780
cagaaaggtg ccgacttcct ggtgacggag gtggaaaatg gtggctcctt gggcagcaag        840
aagggtgtga accttcctgg ggctgctgtg gacttgcctg ctgtgtcgga gaaggacatc        900
caggatctga gtttgggggt cgagcaggat gttgatatgt gtttgcgtc attcatccgc         960 aaggcatctg atgtccatga agttaggaag gtcctgggag agaagggaaa gaacatcaag       1020
attatcagca aaatcgagaa tcatgagggg gttcggaggt ttgatgaaat cctggaggcc       1080
agtgatggga tcatggtggc tcgtggtgat ctaggcattg agattcctgc agagaaggtc       1140
ttccttgctc agaagatgat gattggacgg tgcaaccgag ctgggaagcc tgtcatctgt       1200
gctactcaga tgctggagag catgatcaag aagcccgcc ccactcgggc tgaaggcagt       1260
gatgtggcca atgcagtcct ggatggagcc gactgcatca tgctgtctgg agaaacagcc       1320
aaaggggact atcctctgga ggctgtgcgc atgcagcacc tgatagctcg tgaggctgag       1380
gcagccatgt tccaccgcaa gctgtttgaa gaacttgtgc gagcctcaag tcactccaca       1440
gacctcatgg aagccatggc catgggcagc gtggaggctt cttataagtg tttagcagca       1500
gctttgatag ttctgacgga gtctggcagg tctgctcacc aggtggccag ataccgccca       1560
cgtgccccca tcattgctgt gacccggaat ccccagacag ctcgtcaggc ccacctgtac       1620
cgtggcatct tccctgtgct gtgcaaggac ccagtccagg aggcctgggc tgaggacgtg       1680
gacctccggg tgaactttgc catgaatgtt ggcaaggccc gaggcttctt caagaaggga       1740
gatgtggtca ttgtgctgac cggatggcgc cctggctccg gcttcaccaa caccatgcgt       1800
gttgttcctg tgccgtga                                                     1818
```

-continued

```
<210> SEQ ID NO 45
<211> LENGTH: 2346
<212> TYPE: DNA
<213> ORGANISM: Homo sapiens

<400> SEQUENCE: 45
atggctactc aagctgattt gatggagttg gacatggcca tggaaccaga cagaaaagcg        60
gctgttagtc actggcagca acagtcttac ctggactctg gaatccattc tggtgccact       120
accacagctc cttctctgag tggtaaaggc aatcctgagg aagaggatgt ggatacctcc       180
caagtcctgt atgagtggga acagggattt tctcagtcct tcactcaaga acaagtagct       240
gatattgatg gacagtatgc aatgactcga gctcagaggg tacgagctgc tatgttccct       300
gagacattag atgagggcat gcagatccca tctacacagt ttgatgctgc tcatcccact       360
aatgtccagc gtttggctga accatcacag atgctgaaac atgcagttgt aaacttgatt       420
aactatcaag atgatgcaga acttgccaca cgtgcaatcc ctgaactgac aaaactgcta       480
aatgacgagg accaggtggt ggttaataag gctgcagtta tggtccatca gctttctaaa       540
aaggaagctt ccagacacgc tatcatgcgt tctcctcaga tggtgtctgc tattgtacgt       600
accatgcaga atacaaatga tgtagaaaca gctcgttgta ccgctgggac cttgcataac       660
ctttcccatc atcgtgaggg cttactggcc atctttaagt ctggaggcat tcctgccctg       720
gtgaaaatgc ttggttcacc agtggattct gtgttgtttt atgccattac aactctccac       780 aacctttttat tacatcaaga aggagctaaa atggcagtgc gtttagctgg tgggctgcag       840
aaaatggttg ccttgctcaa caaaacaaat gttaaattct tggctattac gacagactgc       900
cttcaaattt tagcttatgg caaccaagaa agcaagctca tcatactggc tagtggtgga       960
ccccaagctt tagtaaatat aatgaggacc tatacttacg aaaaactact gtggaccaca      1020
agcagagtgc tgaaggtgct atctgtctgc tctagtaata agccggctat tgtagaagct      1080
ggtggaatgc aagctttagg acttcacctg acagatccaa gtcaacgtct tgttcagaac      1140
tgtctttgga ctctcaggaa tctttcagat gctgcaacta acaggaagg gatggaaggt      1200 ctccttggga ctcttgttca gcttctgggt tcagatgata taaatgtggt cacctgtgca      1260
gctggaattc tttctaacct cacttgcaat aattataaga acaagatgat ggtctgccaa      1320
gtgggtggta tagaggctct tgtgcgtact gtccttcggg ctggtgacag ggaagacatc      1380
actgagcctg ccatctgtgc tcttcgtcat ctgaccagcc gacaccaaga agcagagatg      1440
gcccagaatg cagttcgcct tcactatgga ctaccagttg tggttaagct cttacaccca      1500
ccatcccact ggcctctgat aaaggctact gttggattga ttcgaaatct tgccctttgt      1560
cccgcaaatc atgcaccttt gcgtgagcag ggtgccattc cacgactagt tcagttgctt      1620
gttcgtgcac atcaggatac ccagcgccgt acgtccatgg gtgggacaca gcagcaattt      1680
gtggaggggg tccgcatgga agaaatagtt gaaggttgta ccggagccct tcacatccta      1740
gctcgggatg ttcacaaccg aattgttatc agaggactaa ataccattcc attgtttgtg      1800
cagctgcttt attctcccat tgaaaacatc caaagagtag ctgcagggt cctctgtgaa       1860 cttgctcagg acaggaagc tgcagaagct attgaagctg agggagccac agctcctctg       1920
acagagttac ttcactctag gaatgaaggt gtggcgacat atgcagctgc tgttttgttc       1980
cgaatgtctg aggacaagcc acaagattac aagaaacggc tttcagttga gctgaccagc       2040
tctctcttca gaacagagcc aatggcttgg aatgagactg ctgatcttgg acttgatatt      2100
```

-continued

```
ggtgcccagg gagaacccct tggatatcgc caggatgatc ctagctatcg ttcttttcac   2160
tctggtggat atggccagga tgccttgggt atggacccca tgatggaaca tgagatgggt   2220
ggccaccacc ctggtgctga ctatccagtt gatgggctgc cagatctggg gcatgcccag   2280
gacctcatgg atgggctgcc tccaggtgac agcaatcagc tggcctggtt tgatactgac   2340
ctgtaa                                                              2346

<210> SEQ ID NO 46
<211> LENGTH: 1401
<212> TYPE: DNA
<213> ORGANISM: Homo sapiens

<400> SEQUENCE: 46
atggatcccg ggcagcagcc gccgcctcaa ccggccccc aggggccaagg gcagccgcct     60 tcgcagcccc cgcaggggca gggcccgccg tccggacccg ggcaaccggc acccgcggcg    120
acccaggcgg cgccgcaggc acccccgcc gggcatcaga tcgtgcacgt ccgcggggac     180
tcggagaccg acctggaggc gctcttcaac gccgtcatga accccaagac ggccaacgtg    240
ccccagaccg tgcccatgag gctccggaag ctgcccgact ccttcttcaa gccgccggag    300
cccaaatccc actcccgaca ggccagtact gatgcaggca ctgcaggagc cctgactcca    360
cagcatgttc gagctcattc ctctccagct tctctgcagt tgggagctgt ttctcctggg    420
acactgaccc ccactggagt agtctctggc ccagcagcta cacccacagc tcagcatctt    480
cgacagtctt cttttgagat acctgatgat gtacctctgc cagcaggttg ggagatggca    540
aagacatctt ctggtcagag atacttctta aatcacatcg atcagacaac aacatggcag    600
gaccccagga aggccatgct gtcccagatg aacgtcacag cccccaccag tccaccagtg    660
cagcagaata tgatgaactc ggcttcagcc atgaaccaga gaatcagtca gagtgctcca    720
gtgaaacagc caccacccct ggctccccag agcccacagg gaggcgtcat gggtggcagc    780
aactccaacc agcagcaaca gatgcgactc agcaactgc agatggagaa ggagaggctg    840
cggctgaaac agcaagaact gcttcggcag gcaatgcgga atatcaatcc cagcacagca    900
aattctccaa aatgtcagga gttagccctg cgtagccagt taccaacact ggagcaggat    960
ggtgggactc aaaatccagt gtcttctccc gggatgtctc aggaattgag aacaatgacg   1020
accaatagct cagatccttt ccttaacagt ggcacctatc actctcgaga tgagagtaca   1080
gacagtggac taagcatgag cagctacagt gtccctcgaa ccccagatga cttcctgaac   1140
agtgtggatg agatggatac aggtgatact atcaaccaaa gcaccctgcc ctcacagcag   1200
aaccgtttcc cagactacct tgaagccatt cctgggacaa atgtggacct tggaacactg   1260
gaaggagatg gaatgaacat agaaggagag gagctgatgc caagtctgca ggaagctttg   1320
agttctgaca tccttaatga catggagtct gttttggctg ccaccaagct agataaagaa   1380
agctttctta catggttata g                                            1401

<210> SEQ ID NO 47
<211> LENGTH: 888
<212> TYPE: DNA
<213> ORGANISM: Homo sapiens

<400> SEQUENCE: 47
atggaacacc agctcctgtg ctgcgaagtg gaaaccatcc gccgcgcgta ccccgatgcc     60
aacctcctca cgaccgggt gctgcggggcc atgctgaagg cggaggagac ctgcgcgccc    120
tcggtgtcct acttcaaatg tgtgcagaag gaggtcctgc cgtccatgcg gaagatcgtc    180
```

-continued

```
gccacctgga tgctggaggt ctgcgaggaa cagaagtgcg aggaggaggt cttcccgctg      240
gccatgaact acctggaccg cttcctgtcg ctggagcccg tgaaaaagag ccgcctgcag      300
ctgctggggg ccacttgcat gttcgtggcc tctaagatga aggagaccat cccctgacg       360 gccgagaagc tgtgcatcta caccgacaac tccatccggc ccgaggagct gctgcaaatg      420
gagctgctcc tggtgaacaa gctcaagtgg aacctggccg caatgacccc gcacgatttc      480
attgaacact tcctctccaa aatgccagag gcggaggaga caaacagat  catccgcaaa      540 cacgcgcaga ccttcgttgc cctctgtgcc acagatgtga agttcatttc caatccgccc      600
tccatggtgg cagcggggag cgtggtggcc gcagtgcaag gcctgaacct gaggagcccc      660
aacaacttcc tgtcctacta ccgcctcaca cgcttcctct ccagagtgat caagtgtgac      720
ccagactgcc tccgggcctg ccaggagcag atcgaagccc tgctggagtc aagcctgcgc      780
caggcccagc agaacatgga ccccaaggcc gccgaggagg aggaagagga ggaggaggag      840
gtggacctgg cttgcacacc caccgacgtg cgggacgtgg acatctga                  888
```

<210> SEQ ID NO 48
<211> LENGTH: 1362
<212> TYPE: DNA
<213> ORGANISM: Homo sapiens

<400> SEQUENCE: 48

```
ctggattttt ttcgggtagt ggaaaaccag cctcccgcga cgatgcccct caacgttagc       60
ttcaccaaca ggaactatga cctcgactac gactcggtgc agccgtattt ctactgcgac      120
gaggaggaga acttctacca gcagcagcag cagagcgagc tgcagccccc ggcgcccagc      180
gaggatatct ggaagaaatt cgagctgctg cccacccgc  ccctgtcccc tagccgccgc      240
tccgggctct gctcgccctc ctacgttgcg gtcacaccct tctcccttcg gggagacaac      300
gacggcggtg cgggagctt  ctccacggcc gaccagctgg agatggtgac cgagctgctg      360
ggaggagaca tggtgaacca gagtttcatc tgcgacccgg acgacgagac cttcatcaaa      420
aacatcatca tccaggactg tatgtggagc ggcttctcgg ccgccgccaa gctcgtctca      480
gagaagctgg cctcctacca ggctgcgcgc aaagacagcg gcagcccgaa ccccgcccgc      540
ggccacagcg tctgctccac ctccagcttg tacctgcagg atctgagcgc cgccgcctca      600
gagtgcatcg acccctcggt ggtcttcccc taccctctca cgacagcag  ctcgcccaag      660 tcctgcgcct cgcaagactc cagcgccttc tctccgtcct cggattctct gctctcctcg      720
acggagtcct ccccgcaggg cagccccgag cccctggtgc tccatgagga cacaccgccc      780
accaccagca gcgactctga ggaggaacaa gaagatgagg aagaaatcga tgttgtttct      840
gtggaaaaga ggcaggctcc tggcaaaagg tcagagtctg gatcaccttc tgctggaggc      900
cacagcaaac tcctcacag  cccactggtc ctcaagaggt gccacgtctc cacacatcag      960
cacaactacg cagcgcctcc ctccactcgg aaggactatc ctgctgccaa gagggtcaag     1020
ttggacagtg tcagagtcct gagacagatc agcaacaacc gaaaatgcac cagccccagg     1080
tcctcggaca ccgaggagaa tgtcaagagg cgaacacaca acgtcttgga gcgccagagg     1140
aggaacgagc taaaacggag cttttttgcc ctgcgtgacc agatcccgga gttggaaaac     1200
aatgaaaagg cccccaaggt agttatcctt aaaaaagcca cagcatacat cctgtccgtc     1260
caagcagagg agcaaaagct catttctgaa gaggacttgt tgcggaaacg acgagaacag     1320
ttgaaacaca aacttgaaca gctacggaac tcttgtgcgt aa                       1362
```

-continued

```
<210> SEQ ID NO 49
<211> LENGTH: 752
<212> TYPE: DNA
<213> ORGANISM: Artificial Sequence
<220> FEATURE:
<223> OTHER INFORMATION: CopGFP

<400> SEQUENCE: 49
agagcgacga gagcggcctg cccgccatgg agatcgagtg ccgcatcacc ggcaccctga      60
acggcgtgga gttcgagctg gtgggcggcg gagagggcac ccccaagcag ggccgcatga     120
ccaacaagat gaagagcacc aaaggcgccc tgaccttcag cccctacctg ctgagccacg     180
tgatgggcta cggcttctac cacttcggca cctaccccag cggctacgag aacccccttcc    240 tgcacgccat caacaacggc ggctacacca cacccgcat cgagaagtac gaggacggcg      300
gcgtgctgca cgtgagcttc agctaccgct acgaggccgg ccgcgtgatc ggcgacttca     360
aggtggtggg caccggcttc cccgaggaca gcgtgatctt caccgacaag atcatccgca     420
gcaacgccac cgtggagcac ctgcacccca tgggcgataa cgtgctggtg ggcagcttcg     480
cccgcacctt cagcctgcgc gacggcggct actacagctt cgtggtggac agccacatgc     540
acttcaagag cgccatccac cccagcatcc tgcagaacgg gggccccatg ttcgccttcc     600
gccgcgtgga ggagctgcac agcaacaccg agctgggcat cgtggagtac cagcacgcct     660
tcaagacccc catcgccttc gccagatccc gcgctcagtc gtccaattct gccgtggacg     720
gcaccgccgg acccggctcc accggatctc gc                                   752

<210> SEQ ID NO 50
<211> LENGTH: 717
<212> TYPE: DNA
<213> ORGANISM: Artificial Sequence
<220> FEATURE:
<223> OTHER INFORMATION: eGFP

<400> SEQUENCE: 50
atggtgagca agggcgagga gctgttcacc ggggtggtgc ccatcctggt cgagctggac      60
ggcgacgtaa acggccacaa gttcagcgtg tccggcgagg gcgagggcga tgccaccttac    120 ggcaagctga ccctgaagtt catctgcacc accggcaagc tgcccgtgcc ctggcccacc     180
ctcgtgacca ccctgaccta cggcgtgcag tgcttcagcc gctacccccga ccacatgaag    240 cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaag       717

<210> SEQ ID NO 51
<211> LENGTH: 720
<212> TYPE: DNA
<213> ORGANISM: Artificial Sequence
<220> FEATURE:
<223> OTHER INFORMATION: YFP

<400> SEQUENCE: 51
```

-continued

```
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccttcggcta cggcctgcag tgcttcgccc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagct accagtccgc cctgagcaaa gaccccaacg agaagcgcga tcacatggtc       660
ctgctggagt tcgtgaccgc cgccgggatc actctcggca tggacgagct gtacaagtaa       720
```

<210> SEQ ID NO 52
<211> LENGTH: 711
<212> TYPE: DNA
<213> ORGANISM: Artificial Sequence
<220> FEATURE:
<223> OTHER INFORMATION: mCherry

<400> SEQUENCE: 52

```
atggtgagca agggcgagga ggataacatg gccatcatca aggagttcat gcgcttcaag        60
gtgcacatgg agggctccgt gaacggccac gagttcgaga tcgagggcga gggcgagggc       120
cgcccctacg agggcaccca gaccgccaag ctgaaggtga ccaagggtgg ccccctgccc       180
ttcgcctggg acatcctgtc ccctcagttc atgtacggct ccaaggccta cgtgaagcac       240
cccgccgaca tccccgacta cttgaagctg tccttccccg agggcttcaa gtgggagcgc       300
gtgatgaact tcgaggacgg cggcgtggtg accgtgaccc aggactcctc cctgcaggac       360
ggcgagttca tctacaaggt gaagctgcgc ggcaccaact cccctccga cggccccgta        420 atgcagaaga agaccatggg ctgggaggcc tcctccgagc ggatgtaccc cgaggacggc       480
gccctgaagg gcgagatcaa gcagaggctg aagctgaagg acggcggcca ctacgacgct       540
gaggtcaaga ccacctacaa ggccaagaag cccgtgcagc tgcccggcgc ctacaacgtc       600
aacatcaagt tggacatcac ctcccacaac gaggactaca ccatcgtgga acagtacgaa       660
cgcgccgagg gccgccactc caccggcggc atggacgagc tgtacaagta a                711
```

<210> SEQ ID NO 53
<211> LENGTH: 1653
<212> TYPE: DNA
<213> ORGANISM: Artificial Sequence
<220> FEATURE:
<223> OTHER INFORMATION: Luciferase

<400> SEQUENCE: 53

```
atggccgatg ctaagaacat taagaagggc cctgctccct tctaccctct ggaggatggc        60
accgctggcg agcagctgca caaggccatg aagaggtatg ccctggtgcc tggcaccatt       120
gccttcaccg atgcccacat tgaggtggac atcacctatg ccgagtactt cgagatgtct       180
gtgcgcctgg ccgaggccat gaagaggtac ggcctgaaca ccaaccaccg catcgtggtg       240
tgctctgaga actctctgca gttcttcatg ccagtgctgg gcgccctgtt catcggagtg       300
```

-continued

```
gccgtggccc ctgctaacga catttacaac gagcgcgagc tgctgaacag catgggcatt      360
tctcagccta ccgtggtgtt cgtgtctaag aagggcctgc agaagatcct gaacgtgcag      420
aagaagctgc ctatcatcca gaagatcatc atcatggact ctaagaccga ctaccagggc      480
ttccagagca tgtacacatt cgtgacatct catctgcctc ctggcttcaa cgagtacgac      540
ttcgtgccag agtctttcga cagggacaaa accattgccc tgatcatgaa cagctctggg      600
tctaccggcc tgcctaaggg cgtggccctg cctcatcgca ccgcctgtgt gcgcttctct      660
cacgcccgcg accctatttt cggcaaccag atcatccccg acaccgctat tctgagcgtg      720
gtgccattcc accacggctt cggcatgttc accaccctgg ctacctgat ttgcggcttt      780 cgggtggtgc tgatgtaccg cttcgaggag gagctgttcc tgcgcagcct gcaagactac      840
aaaattcagt ctgccctgct ggtgccaacc ctgttcagct tcttcgctaa gagcaccctg      900
atcgacaagt acgacctgtc taacctgcac gagattgcct ctggcggcgc cccactgtct      960
aaggaggtgg gcgaagccgt ggccaagcgc tttcatctgc caggcatccg ccagggctac     1020
ggcctgaccg agacaaccag cgccattctg attaccccag agggcgacga caagcctggc     1080
gccgtgggca aggtggtgcc attcttcgag gccaaggtgg tggacctgga caccggcaag     1140
accctgggag tgaaccagcg cggcgagctg tgtgtgcgcg ccctatgat tatgtccggc     1200 tacgtgaata accctgaggc cacaaacgcc ctgatcgaca aggacggctg gctgcactct     1260
ggcgacattg cctactggga cgaggacgag cacttcttca tcgtggaccg cctgaagtct     1320
ctgatcaagt acaagggcta ccaggtggcc ccagccgagc tggagtctat cctgctgcag     1380
caccctaaca ttttcgacgc cggagtggcc ggcctgcccg acgacgatgc cggcgagctg     1440
cctgccgccg tcgtcgtgct ggaacacggc aagaccatga ccgagaagga gatcgtggac     1500
tatgtggcca gccaggtgac aaccgccaag aagctgcgcg cggagtggt gttcgtggac     1560 gaggtgccca agggcctgac cggcaagctg gacgcccgca agatccgcga gatcctgatc     1620
aaggctaaga aaggcggcaa gatcgccgtg taa                                  1653
```

<210> SEQ ID NO 54
<211> LENGTH: 84
<212> TYPE: DNA
<213> ORGANISM: Mus musculis

<400> SEQUENCE: 54

```
gctagggcgg gatgggacgg ccggttactt aaaggttggg gcgaccaagg gtccgcggcc       60
gcagcctggg tcctcaccgt cgcc                                              84
```

<210> SEQ ID NO 55
<211> LENGTH: 56
<212> TYPE: DNA
<213> ORGANISM: Mus musculis

<400> SEQUENCE: 55

```
caaggatcag agttcggggg ctgagggctc agacgttctt ctctgccctc tccacc          56
```

<210> SEQ ID NO 56
<211> LENGTH: 97
<212> TYPE: DNA
<213> ORGANISM: Mus musculis

<400> SEQUENCE: 56

```
atatcccct tggctcccac tgcttaaata cagactagga cagggctctg tctcctcagc        60
ctcggtcacc acccagctct gggacagcaa gctgaaa                                97
```

-continued

```
<210> SEQ ID NO 57
<211> LENGTH: 36
<212> TYPE: DNA
<213> ORGANISM: Mus musculis

<400> SEQUENCE: 57
tgcgtcacct gaccgcattc tgcacctcaa ctctcc                                    36
```